(12) United States Patent
Moriuchi et al.

(10) Patent No.: US 7,651,524 B2
(45) Date of Patent: *Jan. 26, 2010

(54) FLEXIBLE STENT

(75) Inventors: Yousuke Moriuchi, Shizuoka-ken (JP); Hideaki Yamashita, Shizuoka-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 7 days.

This patent is subject to a terminal disclaimer.

(21) Appl. No.: 11/905,289

(22) Filed: Sep. 28, 2007

(65) Prior Publication Data

US 2008/0097587 A1    Apr. 24, 2008

Related U.S. Application Data

(63) Continuation-in-part of application No. 11/392,490, filed on Mar. 30, 2006.

(30) Foreign Application Priority Data

| Mar. 30, 2005 | (JP) | ............................. | 2005-100194 |
| Nov. 4, 2005 | (JP) | ............................. | 2005-320362 |
| Sep. 29, 2006 | (JP) | ............................. | 2006-269202 |

(51) Int. Cl.
- *A61F 2/06* (2006.01)
- *A61F 2/84* (2006.01)
- *A61F 2/86* (2006.01)
- *A61F 2/88* (2006.01)
- *A61F 2/90* (2006.01)
- *A61F 2/92* (2006.01)
- *A61F 2/94* (2006.01)

(52) U.S. Cl. ...................... 623/1.15; 623/1.1; 623/1.17; 623/1.34

(58) Field of Classification Search ....... 623/1.12–1.18, 623/1.2, 1.22

See application file for complete search history.

(56) References Cited

U.S. PATENT DOCUMENTS 5,810,872 A * 9/1998 Kanesaka et al. .......... 623/1.15

(Continued)

FOREIGN PATENT DOCUMENTS

| EP | 1 415 616 A1 | 5/2004 |
| WO | WO 96/26689 A1 | 9/1996 |

(Continued)

OTHER PUBLICATIONS

European Search Report.

*Primary Examiner*—Thomas J Sweet
*Assistant Examiner*—Yashita Sharma
(74) *Attorney, Agent, or Firm*—Buchanan Ingersoll & Rooney PC

(57) ABSTRACT

A stent to be implanted in an organism includes a plurality of wavy annular members arranged in an axial direction thereof. Each of the wavy annular members has a plurality of one-end side bent portions each having an apex at a one-end side of the stent in the axial direction thereof and a plurality of other-end side bent portions each having an apex at an other-end side of the stent in the axial direction thereof. In the wavy annular members disposed adjacently to each other in the axial direction of the stent the wavy annular members disposed at the one-end side of the stent in the axial direction thereof has a sharing linear portion having a start point at the apex of one of the other-end side bent portions thereof or in the vicinity of the apex and a termination point between the apex of the other-end side bent portion thereof and the apex of one of the one-end side bent portions thereof. The sharing linear portion integrates the adjacent wavy annular members with each other.

35 Claims, 35 Drawing Sheets

U.S. PATENT DOCUMENTS

| | | |
|---|---|---|
| 5,843,117 A * | 12/1998 | Alt et al. .................... 623/1.15 |
| 6,013,854 A | 1/2000 | Moriuchi |
| 6,506,211 B1 | 1/2003 | Skubitz et al. |
| 6,579,310 B1 * | 6/2003 | Cox et al. .................. 623/1.16 |
| 6,620,201 B1 | 9/2003 | Nadal et al. |
| 2003/0105513 A1 * | 6/2003 | Moriuchi et al. ........... 623/1.15 |
| 2003/0144729 A1 | 7/2003 | Bicck et al. |
| 2004/0093073 A1 * | 5/2004 | Lowe et al. ................. 623/1.15 |
| 2004/0199242 A1 * | 10/2004 | Hong et al. ................ 623/1.16 |
| 2004/0243216 A1 | 12/2004 | Gregorich |
| 2006/0100690 A1 * | 5/2006 | Venturelli .................. 623/1.15 |

FOREIGN PATENT DOCUMENTS

| | | |
|---|---|---|
| WO | WO 97/32546 A1 | 9/1997 |
| WO | WO 98/30173 A1 | 7/1998 |
| WO | WO 99/65421 A2 | 12/1999 |
| WO | WO 03/082154 A2 | 10/2003 |

* cited by examiner

FLEXIBLE STENT

BACKGROUND OF THE INVENTION

The present invention relates to a stent that is implanted in lumens of an organism such as a blood vessel, the bile duct the trachea, the esophagus, the ureter, and the like to cure a stenosed portion or a closed portion generated in the lumens.

To cure various diseases that are caused when blood vessels or lumens are stenosed or closed, the stent which is a tubular medical appliance is implanted at the stenosed portion or the closed portion to expand them and secure the lumen thereof. When the stent is inserted into the body from the outside, it has a small diameter. The stent is expanded (or restored to its original state) to make its diameter large at the stenosed portion or the dosed portion to keep the expanded state of the lumen thereof. The stent is classified into a self-expandable stent and a balloon expandable stent in dependence on the function thereof and an expansion mode. The balloon expandable stent itself has no expanding function. After it is inserted into a desired portion inside the organism, it is secured at the desired portion. Then, a balloon disposed in the stent is inflated to expand (plastically deform) the stent by an expansive force of the balloon so that the stent is brought into dose contact with the inner surface of the desired lumen.

It is necessary to perform an operation of expanding the stent of this type in implanting it to the desired portion of the organism. The self-expandable stent is made of an elastic material. The final size of the self-expandable stent is set when it is expanded. In introducing the self-expandable stent into the human body, it is folded into a small size and put into a member (plastic tube in most cases) restricting its configuration. Then the member, namely, the tube is introduced into the human body. The self-expandable stent is discharged from the tube at the desired portion. The self-expandable stent dilates itself owing to its elasticity.

The recent self-expandable stents are mostly composed of annular members formed by connecting a plurality of columnar portions to each other with a plurality of loops so that the annular members have an approximately zigzag pattern. The annular members are connected to each other with connection portions to form the self-expandable stent substantially cylindrically.

In the stent disclosed in WO96/26689, the wavy annular members are connected to each other by connectors obliquely formed.

Another type of stent is known in which adjacent snaking elements or apexes of adjacent zigzag elements penetrate into the adjacent snaking elements or the zigzag elements. This type of the stent is disclosed in WO97/32546. The stent disclosed in WO99/65421, apexes of the above-described zigzag elements are connected to each other with connectors parallel with the axis of the stent.

Still another type of stent is known in which the snaking elements or the zigzag elements form not a straight loop (loops) but a spiral (spirals). The stent of this type is composed of one or a plurality of spirals from its distal end to its proximal end. For example, the stent disclosed in WO98/30173, to keep the configuration of the stent, the zigzag elements are connected to each other by connectors parallel with the axis of the stent. The stent disclosed in U.S. Pat. No. 6,013,854 is composed not of wavy annular members but of a plurality of spirals.

The connector is used in all of the above-described conventional stents to connect the elements to each other. The connector is used to connect the elements to each other, but does not contribute to the generation of an expansive force of the stent.

As a result of energetic researches of the present inventors, they have found that a construction which is composed of an element contributing to the generation of the expansive force and which has the operation of the connector allows the stent to keep an expansive force constant or more than a required degree and a favorable coverage.

It is an object of the present invention to provide a stent which does not substantially display an expansive force, does not have a connection portion having a possibility of adversely affecting the performance of the stent when the stent is curved, and has a sufficient and uniform expansive force.

SUMMARY OF THE INVENTION

The object described above is attained by the following a stent.

A stent comprises a plurality of wavy annular members arranged in an axial direction thereof, wherein each of said wavy annular members has a plurality of one-end side bent portions each having an apex at a one-end side of said stent in said axial direction thereof and a plurality of other-end side bent portions each having an apex at an other-end side of said stent in said axial direction thereof, and in said wavy annular members disposed adjacently to each other in said axial direction of said stent, said wavy annular member disposed at said one-end side of said stent in said axial direction thereof has a sharing linear portion having a start point at said apex of one of said other-end side bent portions thereof or in the vicinity of said apex and a termination point between said apex of said other-end side bent portion thereof and said apex of one of said one-end side bent portions thereof; and said sharing linear portion integrates said adjacent wavy annular members with each other.

DETAILED DESCRIPTION OF THE PREFERRED EMBODIMENTS

The embodiments of the stent of the present invention will be described below with reference to FIGS. 1 through 4.

Figure 1:
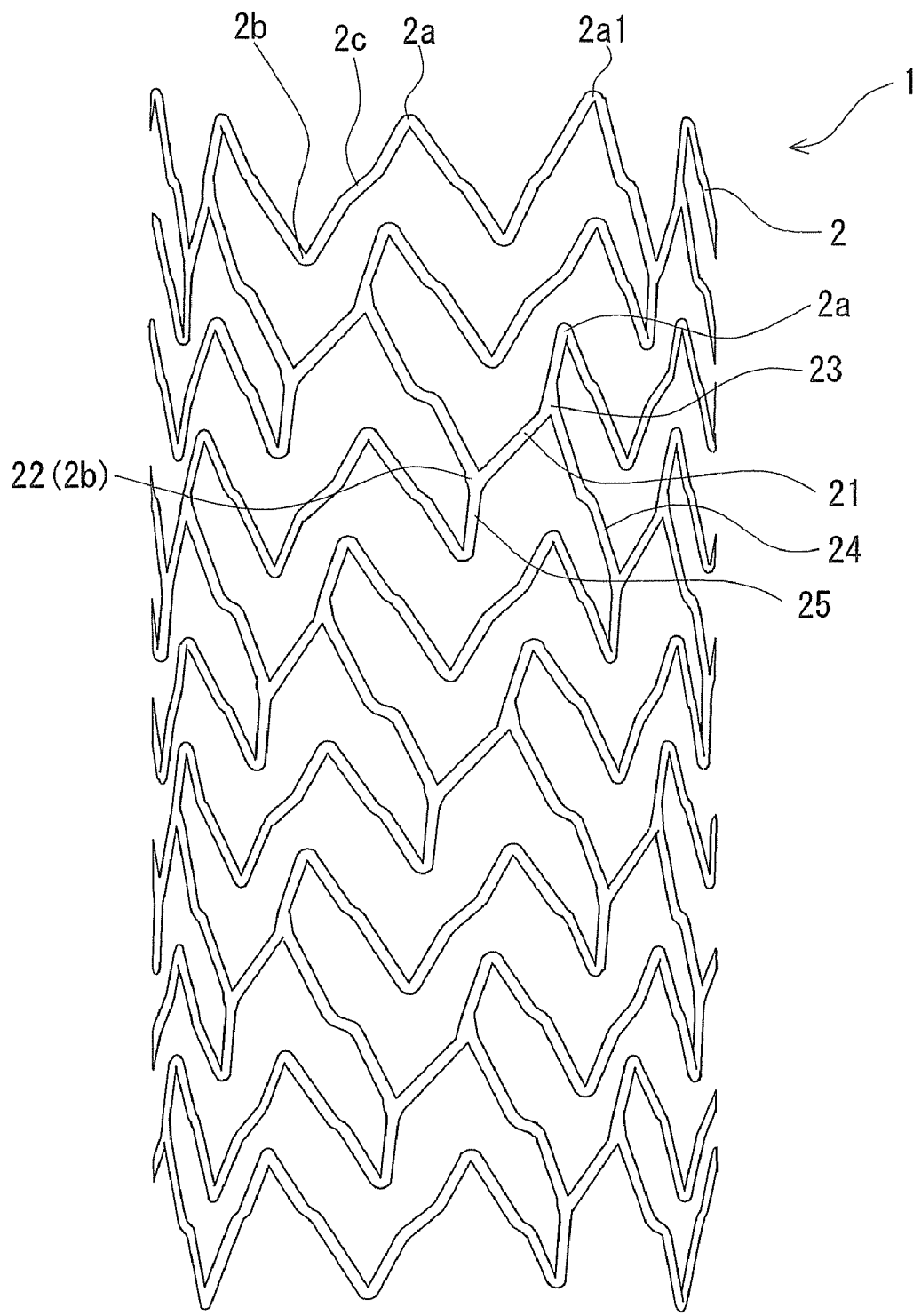
FIG. 1 is a front view showing a stent of one embodiment of the present invention.
Figure 2:
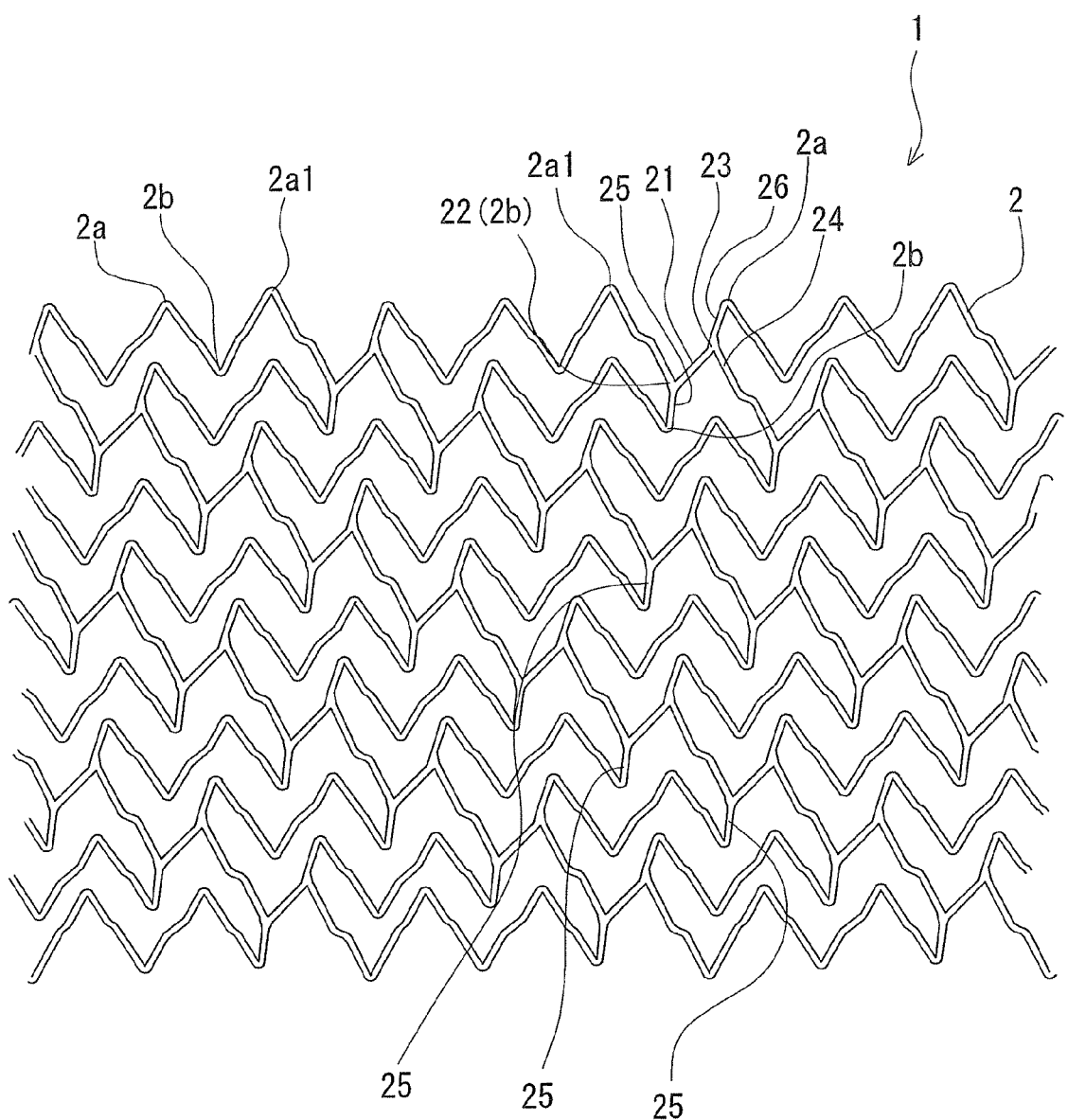
FIG. 2 is a development view showing the stent shown in FIG. 1.
Figure 3:
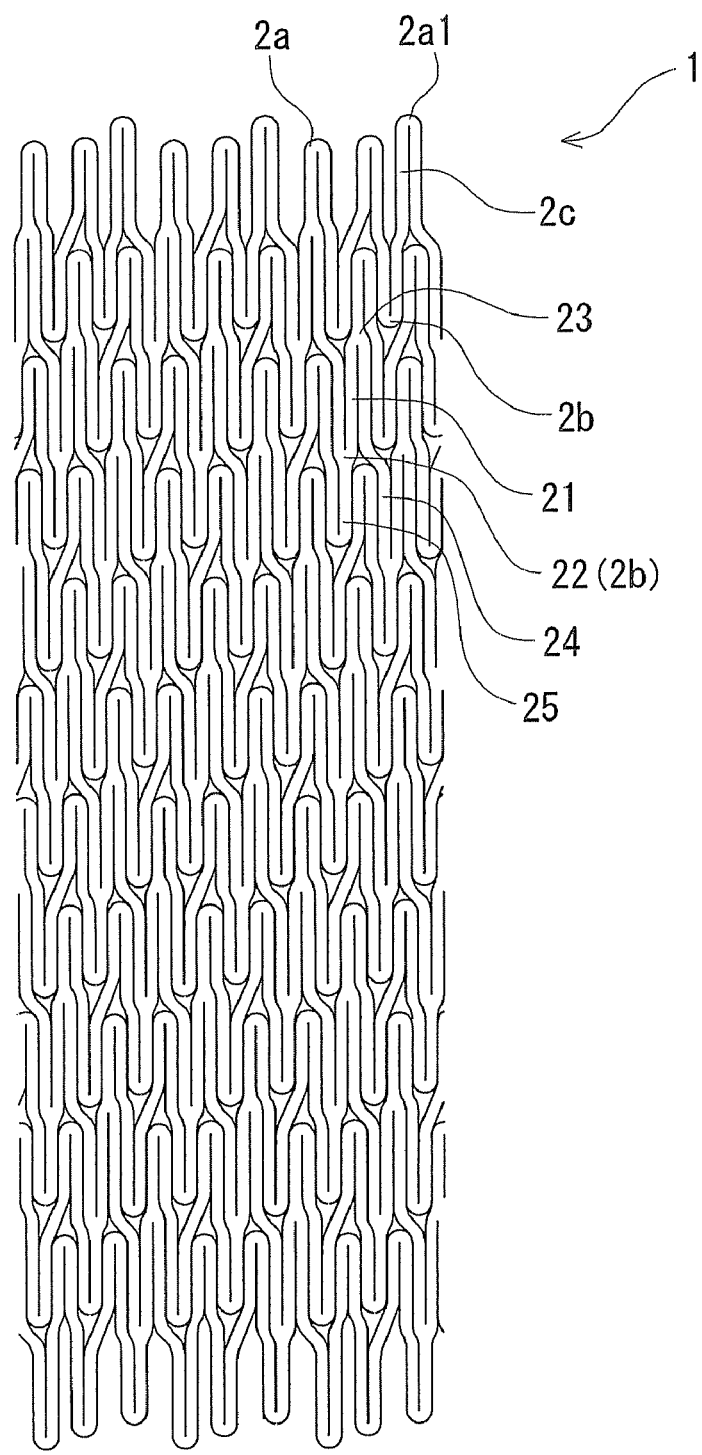
FIG. 3 is a development view showing the stent, shown in FIG. 1, when the stent is contracted.
Figure 4:
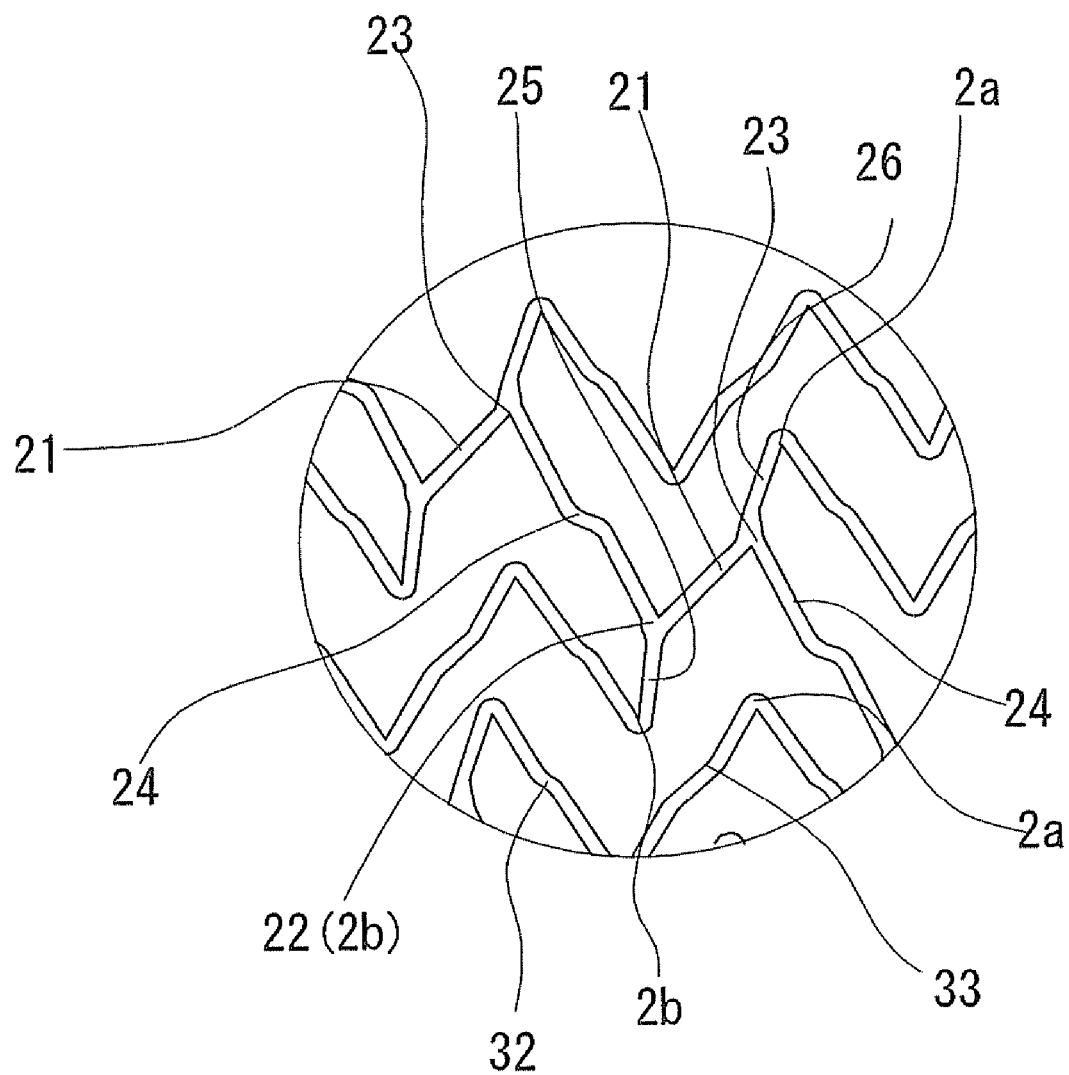
FIG. 4 is a partly enlarged view showing the stent shown in FIG. 1.

FIG. 1 is a front view showing a stent of an embodiment of the present invention. FIG. 2 is a development view showing the stent shown in FIG. 1. FIG. 3 is a development view showing the stent, shown in FIG. 1, whose diameter is decreased. FIG. 4 is a partly enlarged view showing the stent shown in FIG. 1.

A stent 1 of the present invention to be implanted in an organism has a plurality of wavy annular members 2 arranged in an axial direction thereof. Each of the wavy annular members 2 has a plurality of one-end side bent portions each having an apex 2a at a one-end side of the stent 1 in the axial direction thereof and a plurality of other-end side bent portions each having an apex 2b at an other-end side of the stent 1 in the axial direction thereof. In the wavy annular members disposed adjacently to each other in the axial direction of the stent the wavy annular member disposed at the one-end side of the stent in the axial direction thereof has a sharing linear portion 21 having a start point 22 at the apex 2b of one of the other-end side bent portions thereof or in the vicinity of the apex 2b and a termination point 23 between the apex 2b of the other-end side bent portion thereof and the apex 2a of one of the one-end side bent portions thereof. The sharing linear portion 21 integrates the adjacent wavy annular members with each other.

The stent of the present invention has the partial sharing portions which integrate adjacent wavy annular members with each other respectively. That is, the stent does not have a portion serving as only a connection portion of connecting the adjacent wavy annular members with each other, but is composed of portions each displaying an expansive force.

The stent 1 is the so-called self-expandable stent which is formed substantially cylindrically, decreased in its diameter when it is inserted into the organism, and is capable of returning to a configuration before its diameter is decreased, when it is implanted in the organism. FIG. 1 shows the outlook of the stent 1 when it is expanded.

The number of the wavy annular members 2 forming the stent 1 shown in FIG. 1 is set to 11. The number of the wavy annular members 2 is favorably in the range of 2 to 150 and more favorably in the range of 5 to 100, although the number thereof is different in dependence on the length of the stent.

Each of the wavy annular members 2 has a plurality of the one-end side bent portions each having the apex at one-end side of the stent 1 in the axial direction thereof and a plurality of the other-end side bent portions each having the apex at the other-end side of the stent 1 in the axial direction thereof. In addition, each of the wavy annular members 2 is composed of a large number of endless wavy line elements. The one-end side bent portions and the other-end side bent portions of each of the wavy annular members 2 are formed alternately. The number of the one-end side bent portions and that of the other-end side bent portions are equal to each other. The number of the one-end side bent portions (other-end side bent portions) of each of the wavy annular members 2 shown in FIG. 1 is set to nine. The number of the one-end side bent portions (other-end side bent portions) thereof is favorably in the range of 4 to 20 and more favorably in the range of 6 to 12. The wavy line element composing the wavy annular member 2 of the stent 1 of this embodiment curves and has a few straight portions. The wavy line element forming the annular member 2 has a sufficiently large length, thus display a high expansive force when the stent 1 expands. The axial length of the wavy annular member 2 is favorably in the range of 1 to 10 mm and more favorably in the range of 1.5 to 5 mm.

As shown in FIGS. 1, 2, 3, and 4, in the stent of this embodiment, each of the wavy annular members 2 has a big wavy portion forming a projected one-end side apex 2a1 projected closer to the one-end of the stent 1 than the apexes 2a of other one-end side bent portions and a projected other-end side apex (in this embodiment, coincident with start point) 22 projected closer to the other-end of the stent 1 than the apexes 2b of other other-end side bent portions. In this embodiment, the wavy annular member 2 has a plurality of big wavy portions. In the stent 1, one wavy annular member 2 has nine one-end side bent portions and three big wavy portions. The three big wavy portions are substantially equiangularly formed with respect to the axis of the stent 1.

The one-end side wavy annular members 2 adjacent to the other-end side wavy annular member 2 in the axial direction of the stent 1 has a sharing linear portion 21 having the start point 22 at the apex 2b of one of the other-end side bent portions thereof or in the vicinity of the apex 2b and the termination point 23 between the apex 2b of the other-end side bent portion thereof and the apex 2a of one of the one-end side bent portions thereof. The sharing linear portion 21 integrates the adjacent wavy annular members with each other.

More specifically, the sharing linear portion 21 has its start point 22 at the apex 2b of one of the other-end side bent portions of the wavy annular members 2 disposed at the one-end side of the stent 1 in the axial direction thereof. The start point 22 is coincident with the apex 2b. The sharing linear portion 21 has its termination point 23 between the above-described apex 2b and the apex 2a of one of the one-end side bent portions thereof continuous with the apex 2b (coincident with start point 22). In this embodiment the sharing linear portion 21 has its termination point in the vicinity of approximately the midpoint between the apex 2b (coincident with start point 22) of the other end-side bent portion and the apex 2a of the one-end side bent portion continuous with the apex 2b. It is preferable to dispose the termination point 23 at the midpoint between the apexes 2b and 2a. But the termination point 23 may be shifted to the side of the apex 2a or to the side of the apex 2b with respect to the midpoint by 1/100 to 49/100 of the whole length between the apex 2b (or start point 22) and the apex 2a of the one-end side bent portion continuous with the apex 2b. But in this case, it is preferable that the termination point 23 is shifted to the side of the apex 2a with respect to the midpoint.

Because the stent 1 has the above-described construction, the stent 1 has a bifurcating portion (in other words, start point bifurcating portion) formed by a start point of the sharing linear portion 21 and a bifurcating portion (in other words, termination point bifurcating portion) formed by a termination point of the sharing linear portion 21. More specifically, the start point bifurcating portion bifurcates toward the one-end of the stent 1 from the start point 22 serving as a bifurcation point. The termination point bifurcating portion bifurcates toward the other-end of the stent 1 from the termination point 23 serving as a bifurcation point.

In the stent 1 of this embodiment the linear portion disposed between the projected one-end side apex 2a1 of the big wavy portion and the projected other-end side apex (coincident with start point 22) thereof form a long linear portion longer than linear portions connecting adjacent apexes to each other respectively. As described above, the other end of the long linear portion is coincident with the sharing linear portion 21. In this embodiment the sharing linear portion 21 is formed as a portion of the big wavy portion.

As shown in FIG. 2, in the stent 1 of this embodiment, each wavy annular member 2 has a short linear portion 26 connecting the termination point 23 of the sharing linear portion 21 thereof and the apex 2a of the one-end side bent portion thereof to each other. As shown in FIG. 2, the wavy annular member 2 integrated with the adjacent wavy annular member 2 having the short linear portion 26 by means of the sharing linear portion 21 has a short linear portion 25 connecting the start point 22 of the sharing linear portion 21 and the apex 2b of the other-end side bent portion thereof to each other and a long linear portion 24 connecting the termination point 23 of the sharing linear portion 21 and the other apex 2b of the other-end side bent portion thereof to each other. Thus the long linear portion 24 is composed of the linear portion between the projected one-end side apex (coincident with termination point 23) of the big wavy portion and the projected other-end side apex (coincident with start point 22 of sharing linear portions of wavy annular member adjacently disposed at other-end side of stent). That is, when the sharing linear portions 21 of the stent 1 adjacent to each other in the axial direction thereof are viewed from the one end of the axial direction thereof, the long linear portion 24 connects the termination point 23 of one sharing linear portion 21 and the start point 22 of the adjacent sharing linear portion 21 to each other. Therefore a zigzag composed of repetition of the unit of the long linear portion 24 and the sharing linear portion 21 form a spiral in a direction from the one end of the stent toward the other end thereof.

The stent 1 does not have any connection portions. Thus the stent does not have interruptions of curvature or deterioration in the expansive force caused by the formation of the connection portion. Thereby the stent displays a uniform expanded state retention force.

The stent 1 of this embodiment has a plurality of sharing linear portions 21 between the wavy annular members 2 adjacent to each other in the axial direction thereof. More specifically, three sharing linear portions 21 are formed between the adjacent wavy annular members 2. The three sharing linear portions 21 are substantially equiangularly formed with respect to the axis of the stent 1.

In the stent 1, the short linear portions 25 each connecting the start point 22 of the sharing linear portion 21 and the apex 2b of the other-end side bent portion to each other are formed not continuously in the axial direction of the stent 1, but a line connecting the short linear portions 25 to each other is substantially straight. As shown in FIG. 4, in the stent 1, each linear portion has a curved portion 32 in the vicinity of a middle position thereof gong linear portion and other linear portions) except the short linear portions 25, 26. The curved portion 32 makes the progress directions of linear portions almost parallel with each other and shifts the progress directions thereof to some extent in the axial direction of the stent. The curved portion 32 allows the linear portions to be long and the stent to have a high expansive force.

The length of the long linear portion 24 (length between termination point 23 of one sharing linear portion 21 and start point 22 of adjacent sharing linear portion 21) is a little larger than the length of the sum of the length of the sharing linear portion 21 and that of the short linear portion 25 (length between termination point 23 of one sharing linear portion 21 and apex 2b across start point 22). Thereby it is possible to prevent the apex 2b from excessively approaching a linear portion 33 (linear portion which connects the apex 2a and 2b to each other and does not form sharing linear portion nor has branch portion) of the adjacent wavy annular member and decrease the degree of nonuniformity of the axial length of a dosed space (as shown in FIG. 2, in this embodiment dosed space is formed by letter V connected with letter M) formed by wavy annular members. Thereby the stent displays a high expanded state retention force.

As shown in FIG. 2, the apex 2a of each of the one-end side bent portions of each wavy annular member 2 penetrates into a space formed between the apexes 2b of the adjacent other-end side bent portions of one of the adjacent wavy annular members 2. The apex 2b of each of the other-end side bent portions of each wavy annular member 2 penetrates into a space formed between the apexes 2a of the adjacent one-end side bent portions 21 of the other of the adjacent wavy annular members 2. Thereby it is possible to form the long wavy annular member constituting the stent and decrease the area of the closed space (as shown in FIG. 2, in this embodiment dosed space is formed by letter V connected with letter M) formed by the wavy annular member. Thereby the stent displays a high expanded state retention force.

When the stent 1 of this embodiment contracts, as shown in FIG. 3, wavy line elements are arranged, with gaps very little present in the circumferential direction of the stent 1. Therefore the stent 1 has a high coverage.

Figure 5:
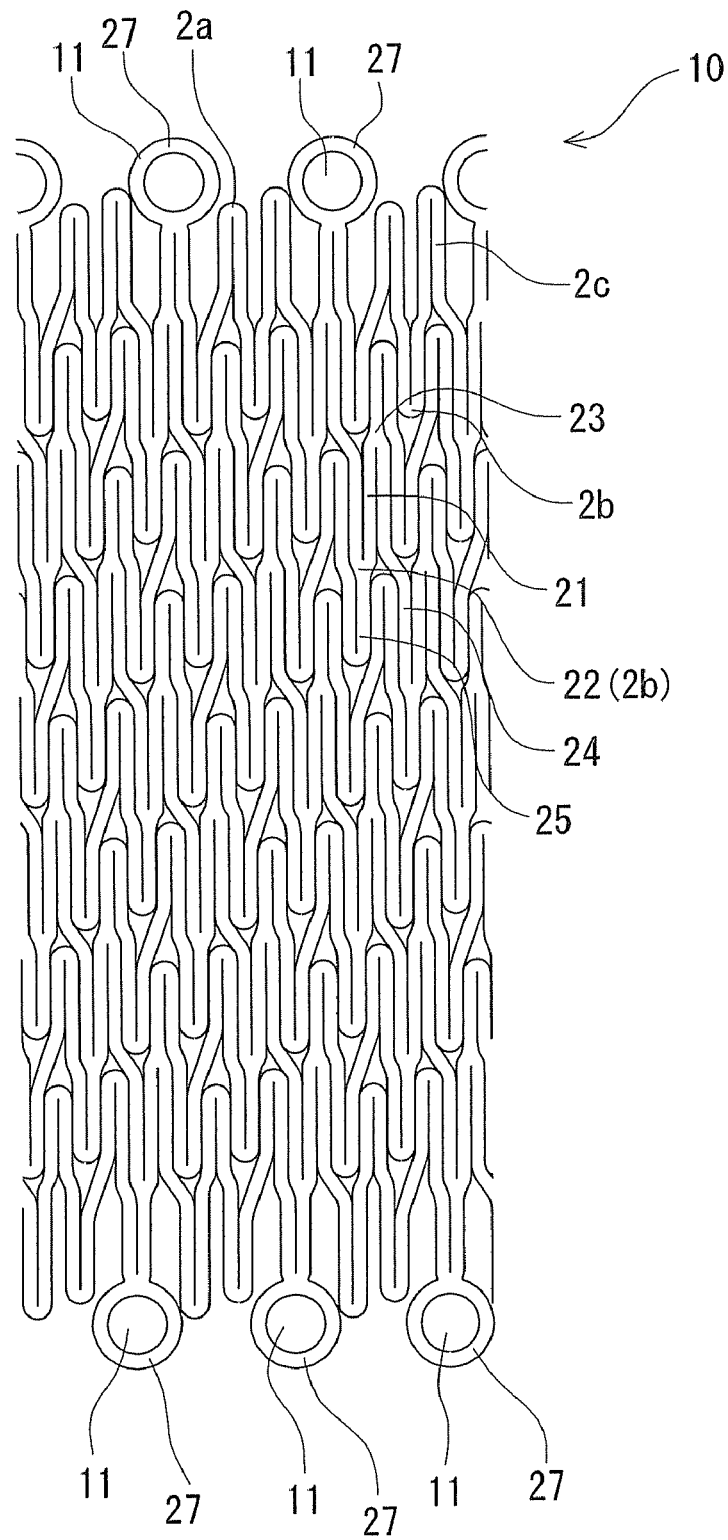
FIG. 5 is a development view showing another embodiment of the stent of the present invention, when the stent is contracted.

It is preferable to provide the stent 10 shown in FIG. 5 with a marker 11. It is favorable to dispose the marker 11 at an end of the stent 10. It is more favorable to dispose the marker 11 at both ends of the stent. More specifically, as shown in FIG. 5, it is preferable to dispose a plurality of the markers 11 at both ends of the stent.

The stent 10 of this embodiment has an opening 27 formed at an apex disposed at one end of the stent. The marker 11 is fixed to the stent to close the opening 27.

It is preferable to mount the marker 11 on a small opening formed on the stent by pressing a disk-shaped member disposed on a small opening. The disk-shaped member is made of an X-ray contrast material having a portion a little smaller than the small opening and a portion a little larger than the small opening. Thereafter the disk-shaped member is pressed in a direction from both surfaces thereof to caulk it to the small opening like a rivet.

It is possible to use an X-ray contrast marker, an ultrasonic wave contrast marker, and the like. The marker is made of contrast substances such as an X-ray contrast substance, an ultrasonic wave contrast substance, and the like. As materials of the marker, it is preferable to use gold, platinum, tungsten tantalum, iridium, palladium, alloys of these metals, a gold-palladium alloy, a platinum-iridium alloy, NiTiPd, and NiTiAu.

Figure 6:
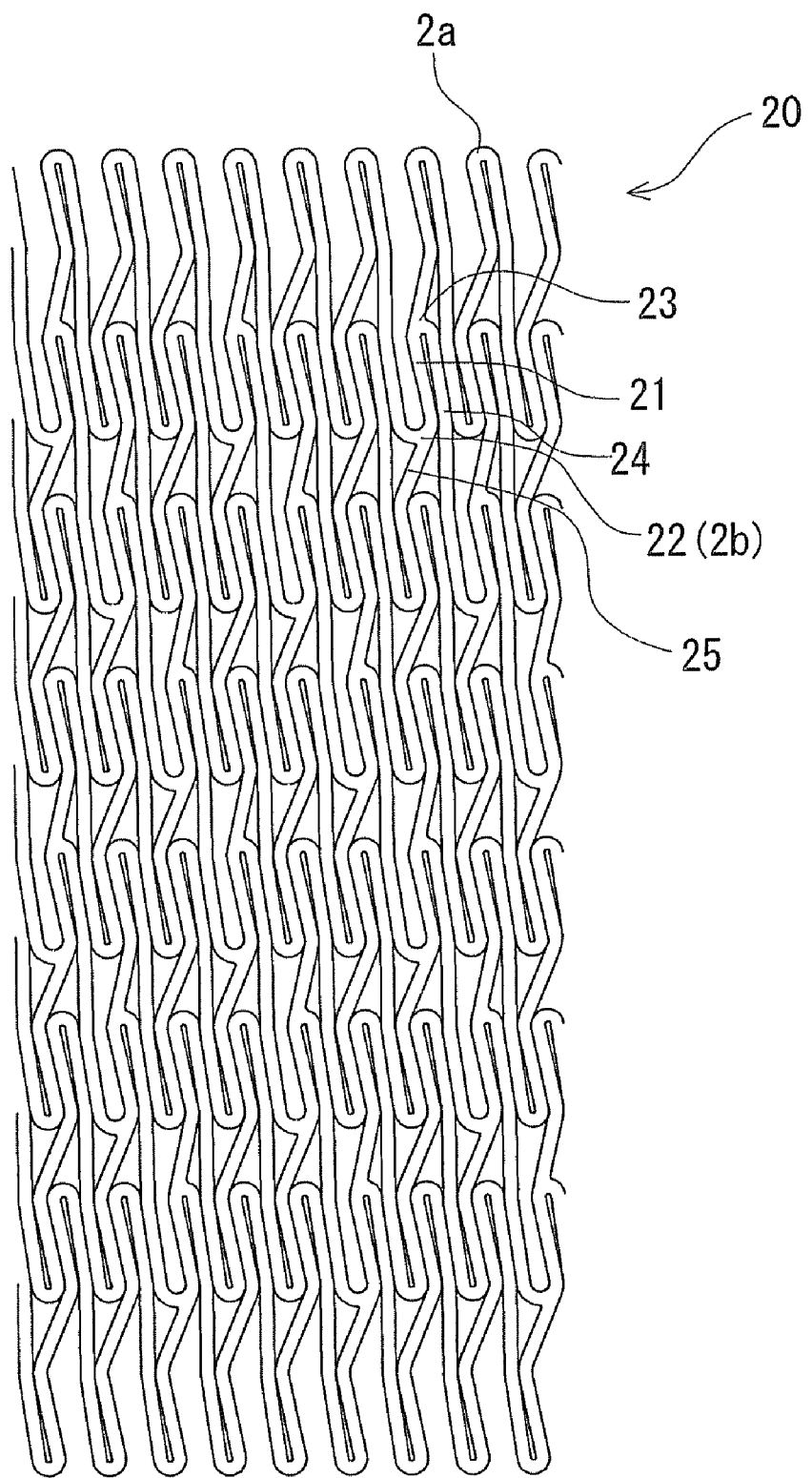
FIG. 6 is a development view showing still another embodiment of the stent of the present invention, when the stent is contracted.

The stent of the present invention may be formed as a stent 20 having a construction as shown in FIG. 6. FIG. 6 is a development view showing still another embodiment of the stent of the present invention.

The stent 20 has the same construction as that of the stent 1 except that the big wavy portion is not formed in each wavy annular member 2 thereof and that each wave has approximately the same size. Another difference is that in the stent 20, a gap is formed beside a portion forming the sharing linear portion 21.

Figure 7:
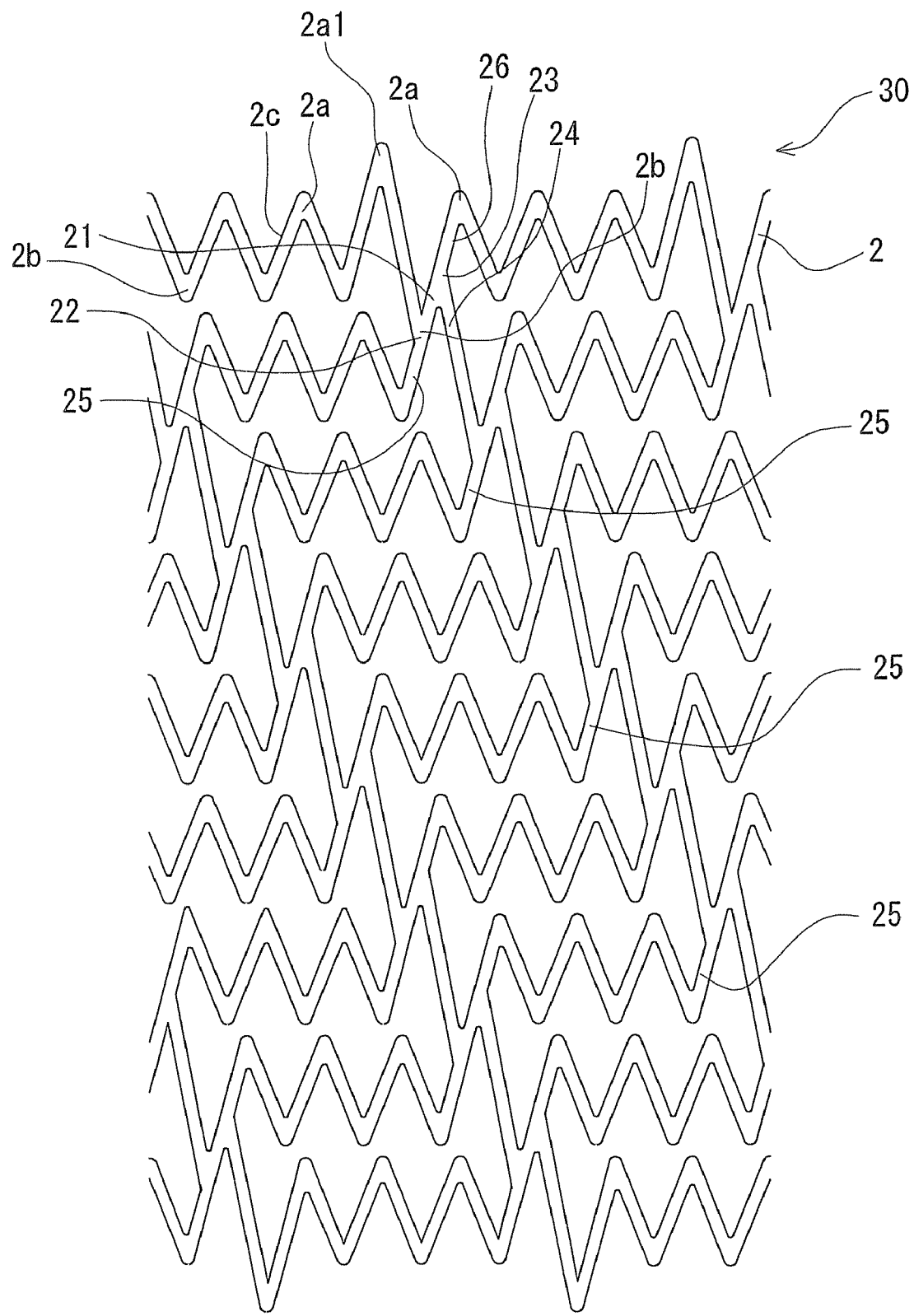
FIG. 7 is an explanatory view for explaining a pattern of still another embodiment of the stent of the present invention.

The stent of the present invention may be formed as a stent 30 having a construction as shown in FIG. 7. FIG. 7 is an explanatory view for explaining a pattern of still another embodiment of the stent of the present invention.

The stent 30 has the same construction as that of the stent 1 except the number of the one-end side bent portions of one wavy annular member 2, that of the other-end side bent portions thereof, and that of the sharing linear portions 21 integrating the adjacent wavy annular members with each other. The number of the one-end side bent portions and the other-end side bent portions of one wavy annular member 2 of the stent 30 is smaller than that of one wavy annular member 2 of the stent 1. More specifically, the number of the one-end side bent portions and the other-end side bent portions of one wavy annular member 2 of the stent 30 are eight respectively. One wavy annular member 2 has two big wavy portions opposed to each other with respect to the axis of the stent 30. The adjacent two wavy annular members are integrated with each other by two sharing linear portions 21. The two sharing linear portions 21 are opposed to each other with respect to the axis of the stent 30.

Figure 8:
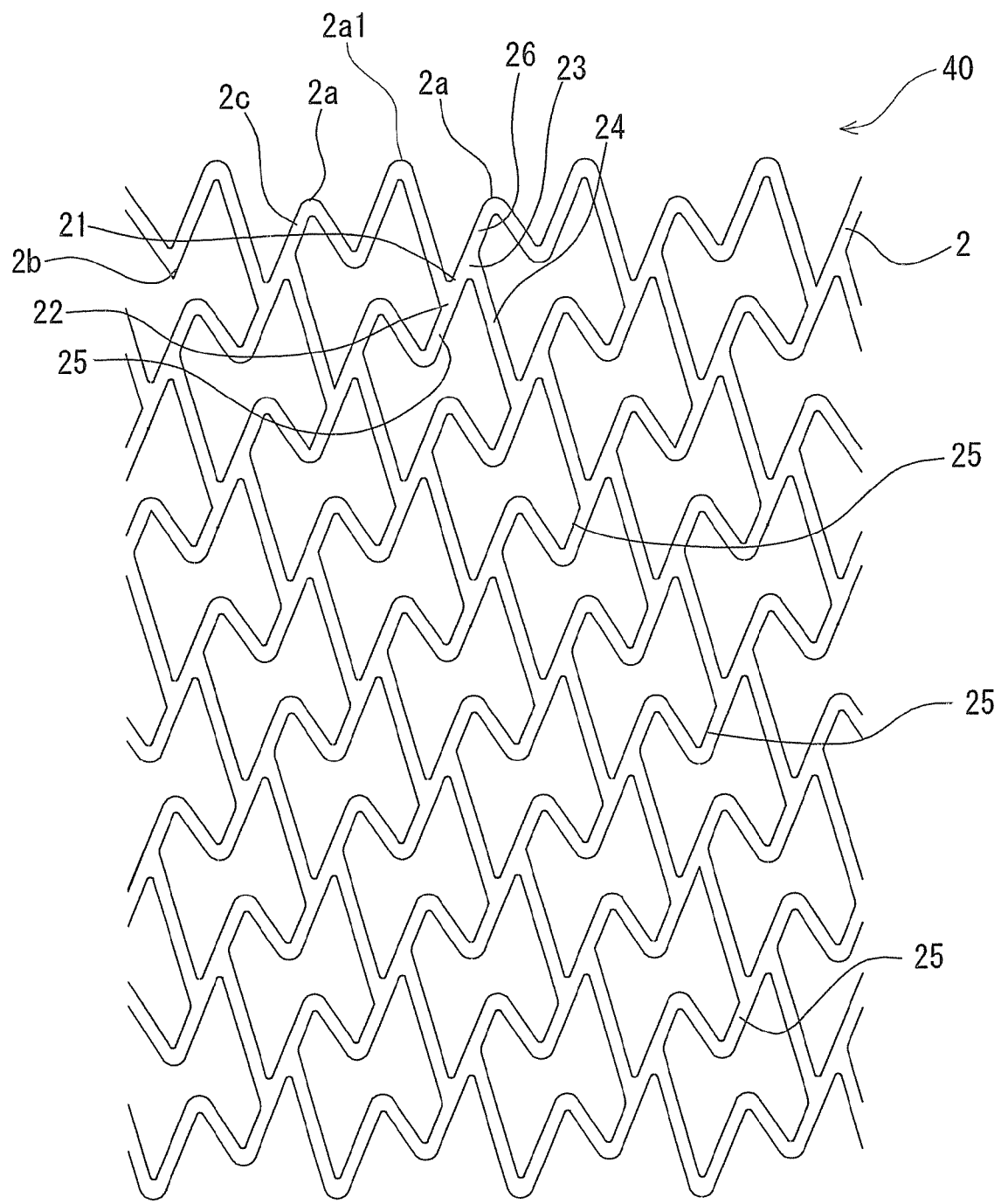
FIG. 8 is an explanatory view for explaining a pattern of still another embodiment of the stent of the present invention.

The stent of the present invention may be formed as a stent 40 having a construction as shown in FIG. 8. FIG. 8 is an explanatory view for explaining a pattern of still another embodiment of the stent of the present invention.

The stent 40 has the same construction as that of the stent 1 except the number of the one-end side bent portions of one wavy annular member 2, that of the other-end side bent portions thereof, and that of the sharing linear portions 21 integrating the adjacent wavy annular members with each other. In the stent 40, the number of the one-end side bent portions and the other-end side bent portions of one wavy annular member 2 of the stent 40 is smaller than that of one wavy annular member 2 of the stent 1. More specifically, the number of the one-end side bent portions and the other-end side bent portions of one wavy annular member 2 of the stent 40 are eight respectively. One wavy annular member 2 has four big wavy portions substantially equiangularly formed with respect to the axis of the stent 40. The adjacent two wavy annular members are integrated with each other by four sharing linear portions 21. The four sharing linear portions 21 are substantially equiangularly formed with respect to the axis of the stent 40.

The diameter of each of the stent of the above-described embodiment decreases when a load is applied radially inward from the entire peripheral surface thereof.

Figure 9:
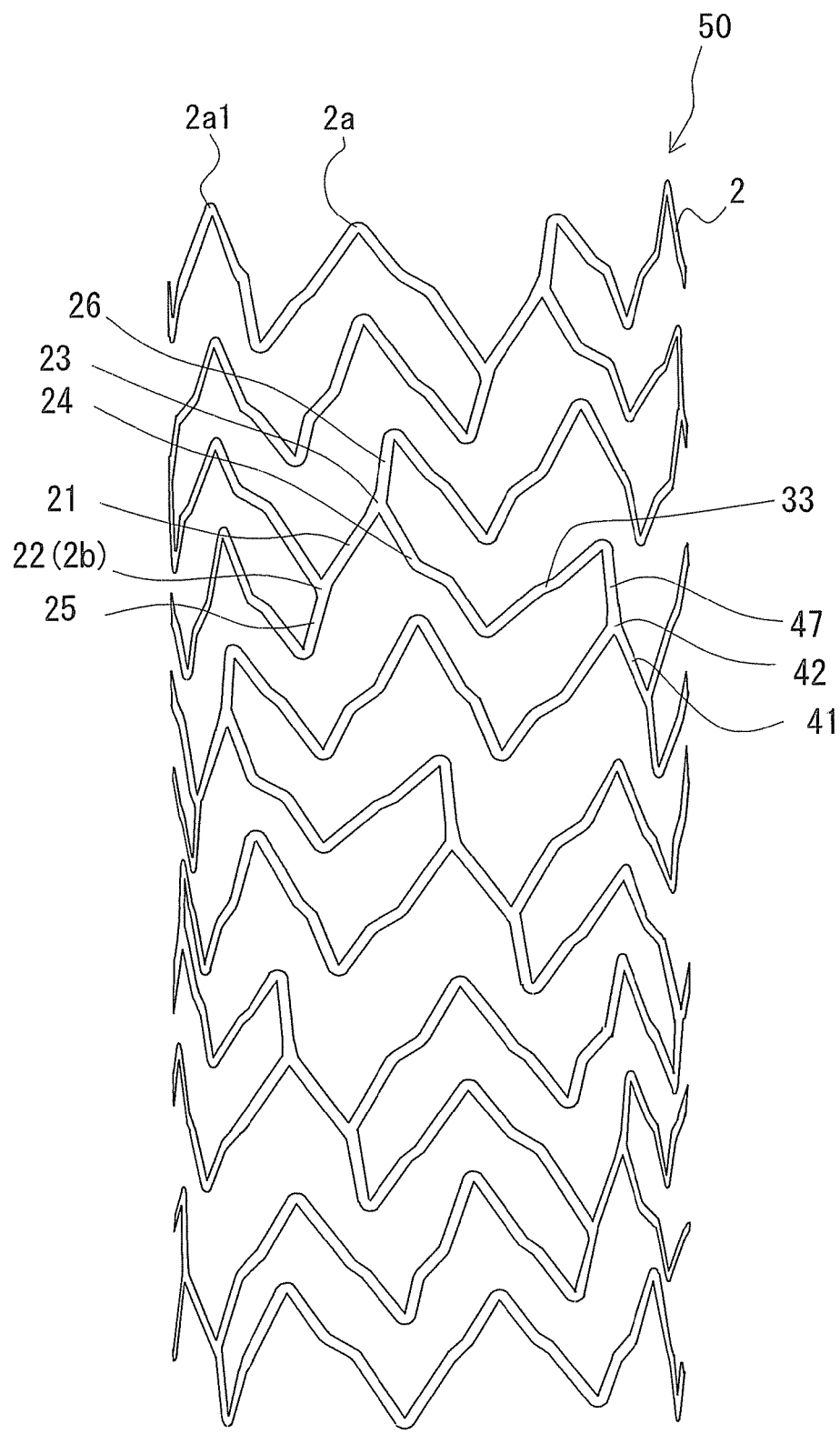
FIG. 9 is a front view showing still another embodiment of the stent of the present invention.
Figure 10:
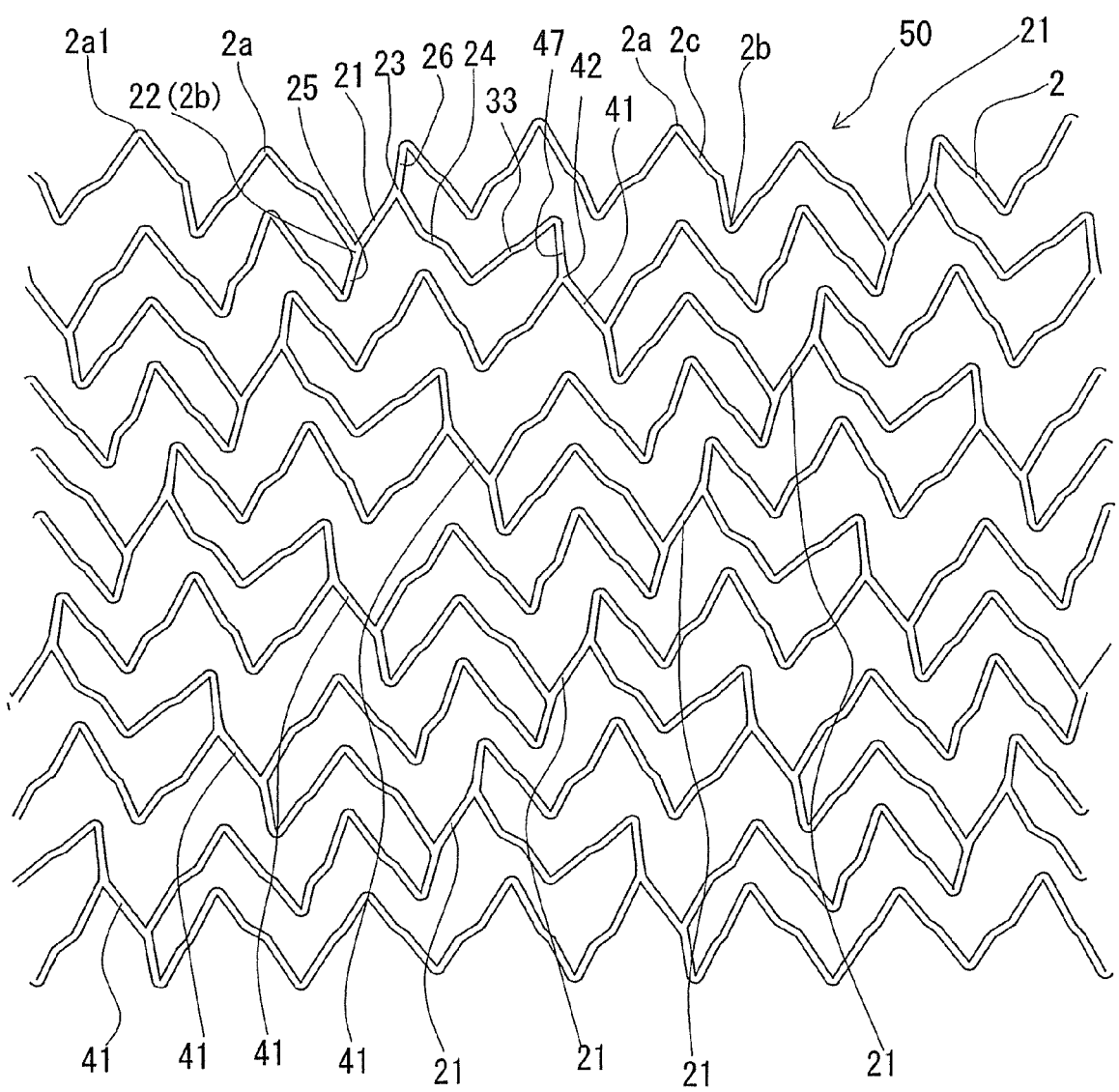
FIG. 10 is a development view showing the stent shown in FIG. 9.
Figure 11:
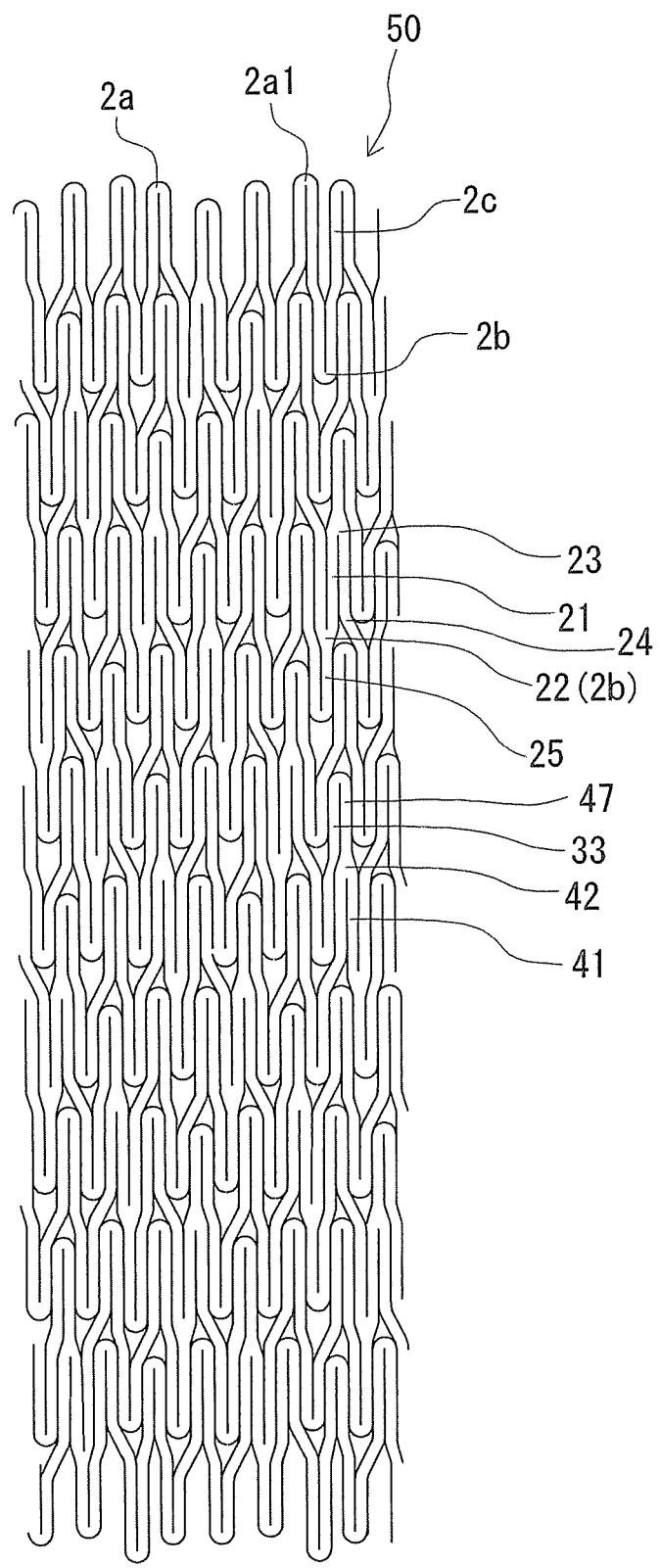
FIG. 11 is a development view showing the stent, shown in FIG. 9, when the stent is contracted.

The stent of the present invention may be formed as a stent 50 having a construction as shown in FIGS. 9 through 11. FIG. 9 is a front view showing still another embodiment of the stent of the present invention. FIG. 10 is a development view showing the stent shown in FIG. 9. FIG. 11 is a development view showing the stent shown in FIG. 9, whose diameter is decreased.

The stent 50 has the same construction as that of the stent 1 except the number of the one-end side bent portions of one wavy annular member 2 the number of the other-end side bent portions, the number of the sharing linear portions 21 integrating the adjacent wavy annular members with each other, the arrangement form of the sharing linear portions, and the orientation thereof.

The number of the one-end side bent portions of one wavy annular member 2 of the stent 50 and that of the other-end side bent portions thereof are smaller than that of one wavy annular member 2 of the stent 1. More specifically, the number of the one-end side bent portions of one wavy annular member 2 of the stent 50 and that of the other-end side bent portions of one wavy annular member 2 thereof are eight respectively. Eleven wavy annular members 2 are disposed in the axial direction of the stent 50. The adjacent two wavy annular members 2 are integrated with each other by two sharing linear portions 21 (first pattern sharing linear portion 21) or two sharing linear portions 41 (second pattern sharing linear portion 41). The two sharing linear portions 21 are opposed to each other with respect to the axis of the stent 50. Similarly the two sharing linear portions 41 are opposed to each other with respect to the axis of the stent 50.

In the stent 50, the first pattern sharing linear portion 21 and the second pattern sharing linear portion 41 are disposed alternately with respect to the axial direction thereof. Further, the first pattern sharing linear portion 21 and the second pattern sharing linear portion 41 are disposed uncontinuously with each other in the axial direction of the stent 50. More specifically, the second pattern sharing linear portion 41 is shifted from the first pattern sharing linear portion 21 in the circumferential direction of the stent 50.

In the stent 50, the first pattern sharing linear portion 21 and the second pattern sharing linear portion 41 extend obliquely with respect to the axial direction of the stent and are different from each other in the orientation thereof.

More specifically, in the stent 50, one annular member 2 has two big wavy portions formed at positions opposed to each other with respect to the axis thereof. The adjacent two wavy annular members 2 are integrated with each other by two sharing linear portions. In the stent 50, the termination point of the first pattern sharing linear portion 21 of one wavy annular member 2 is connected to the other-end side bent portion thereof by a linear portion 24. Similarly the termination point of the second pattern sharing linear portion 41 of one wavy annular member 2 is connected to the other-end side bent portion thereof by the linear portion 24. That is, in the stent 1, the long linear portion 24 connects two sharing linear portions (exactly, termination point of sharing linear portion of one wavy annular member and start point of sharing linear portion of adjacent wavy annular member are connected to each other) adjacent to each other in the axial direction of the stent 1 to each other. On the other hand, in the stent 50, the linear portion 24 does not connect the sharing linear portions to each other. The linear portion 24 connected with the sharing linear portion is not formed as clearly as the long linear portion 24 of the stent 1. The linear portion 24 of the stent 50 is a little longer than other linear portions but may be formed as a long linear portion.

In the stent 50, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent are substantially equiangularly disposed with respect to the axis of the stent 50. Similarly two second pattern sharing linear portions 41 adjacent to each other in the axial direction thereof are also substantially equiangularly disposed with respect to the axis thereof. Thereby the stent 50 is capable of entirely displaying a substantially uniform expansive force.

As shown in FIG. 10, in the stent 50, the first pattern sharing linear portions 21 are spirally disposed in the axial direction thereof. Similarly the second pattern sharing linear portions 41 are spirally disposed in the axial direction thereof.

As shown in FIG. 10, the stent 50 has 11 wavy annular members arranged in the axial direction thereof. The first pattern sharing linear portions 21 are spirally disposed in the axial direction thereof. Similarly the second pattern sharing linear portions 41 are spirally disposed in the axial direction thereof. More specifically, the adjacent wavy annular members are connected with each other by two first pattern sharing linear portions 21. The first pattern sharing linear portions 21 are spirally disposed in the axial direction of the stent 50 to form two spirals. Each of the two spirals is composed of five first pattern sharing linear portions 21. Similarly the adjacent wavy annular members (not connected by first pattern sharing linear portion 21) are connected with each other by two second pattern sharing linear portions 41. The second pattern sharing linear portions 41 are spirally disposed in the axial direction of the stent 50 to form two spirals. Each of the two spirals is constructed of five second pattern sharing linear portions 41.

As described above, the first pattern sharing linear portions 21 and the second pattern sharing linear portions 41 extend obliquely with respect to the axial direction of the stent 50 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 50 is capable of entirely displaying a substantially uniform expansive force.

As shown in FIG. 10, one wavy annular member 2 of the stent 50 has a short linear portion 26 connecting the termination point 23 of the first pattern sharing linear portion 21 thereof and the apex 2a of the one-end side bent portion thereof to each other. The wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 42 of the second pattern sharing linear portion 41 thereof and the apex of the one-end side bent portion thereof to each other.

The construction of the stent 50 of this embodiment is different from that of the stent 1. The construction of the stent 50 makes a resistance to an axial expansion and contraction of the wavy annular member smaller than the resistance thereto in the stent 1. Thereby the stent 50 has more favorable follow-up performance for deformation of blood vessels.

Figure 12:
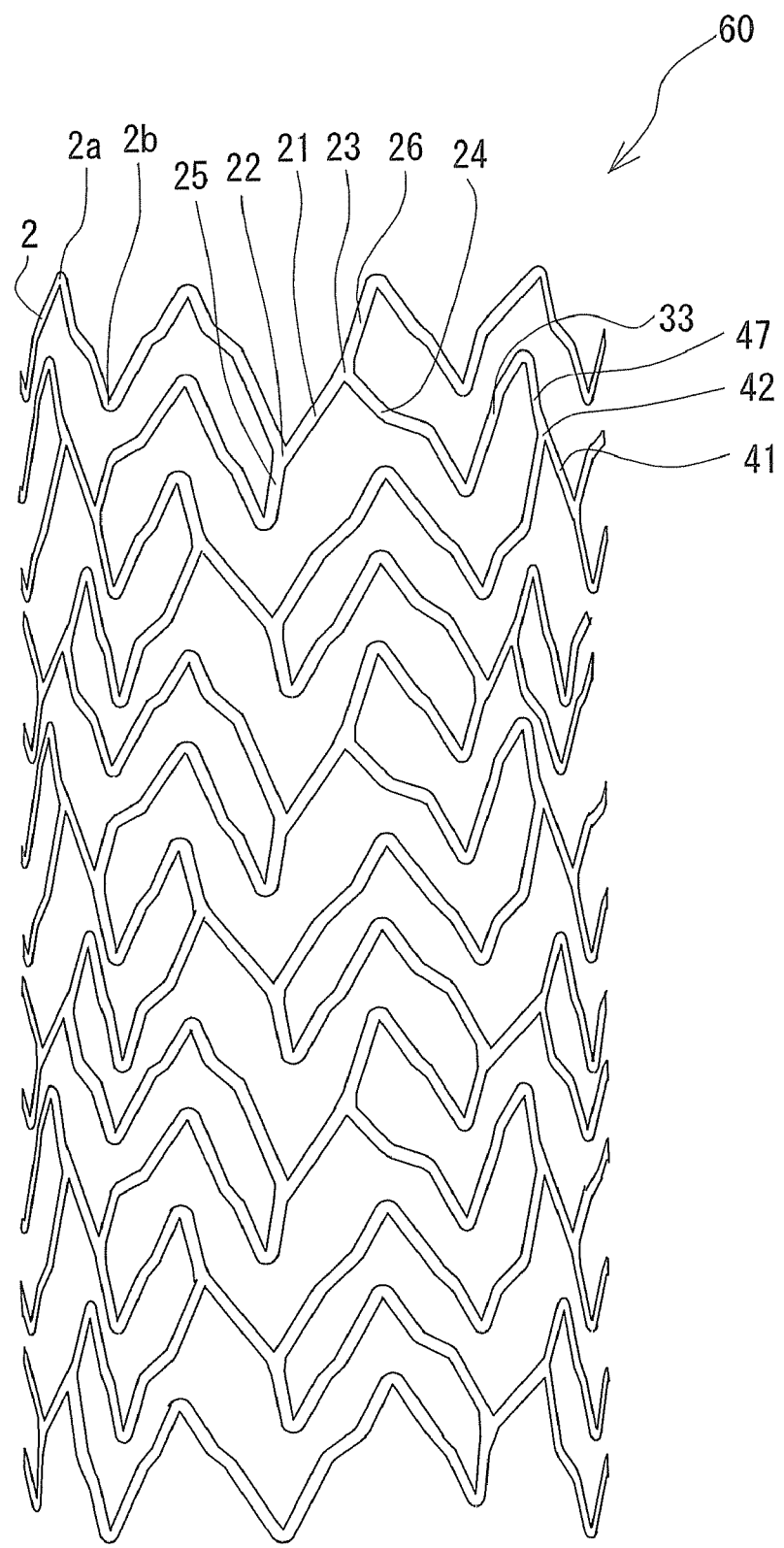
FIG. 12 is a front view showing still another embodiment of the stent of the present invention.
Figure 13:
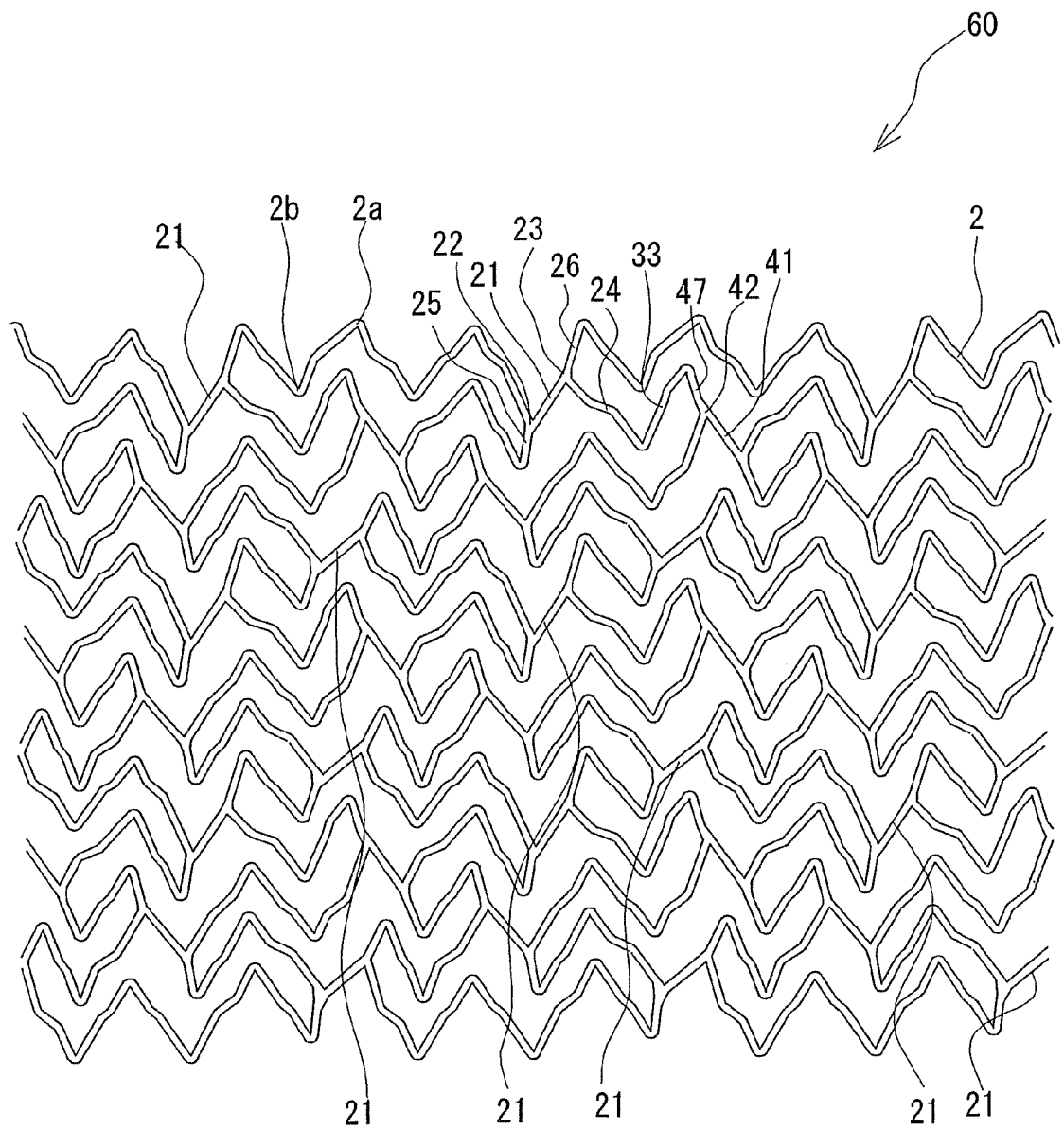
FIG. 13 is a development view showing the stent shown in FIG. 12.
Figure 14:
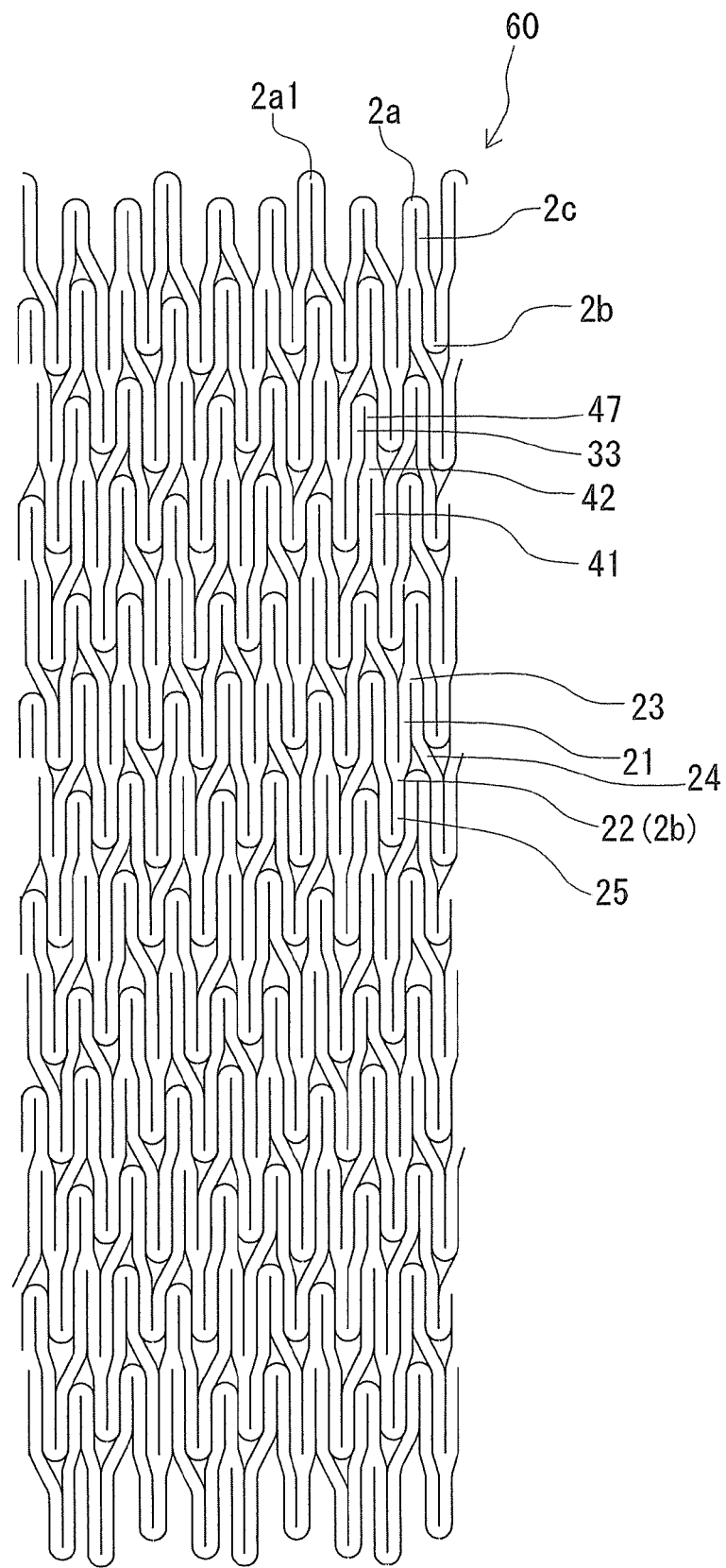
FIG. 14 is a development view showing the stent shown in FIG. 12, when the stent is contracted.

The stent of the present invention may be formed as a stent 60 having a construction as shown in FIGS. 12 through 14. FIG. 12 is a front view showing still another embodiment of the stent of the present invention FIG. 13 is a development view showing the stent shown in FIG. 12. FIG. 14 is a development view showing the stent, shown in FIG. 12, whose diameter is decreased.

The stent 60 has the same construction as that of the stent 1 except the arrangement form of the sharing linear portion and the orientation thereof. In the stent 60, the sharing linear portions (first pattern sharing linear portion) 21 and the sharing linear portions (second pattern sharing linear portion) 41 are formed substantially straight respectively in the axial direction of the stent 60.

In the stent 60, the number of the one-end side bent portions of one wavy annular member 2 thereof and that of the other-end side bent portions thereof are equal to that of the wavy annular member 2 of the stent 1. More specifically, the number of the one-end side bent portions of the wavy annular member 2 and that of the other-end side bent portions are nine respectively. Thirteen wavy annular members 2 are arranged in the axial direction of the stent 60. The adjacent two wavy annular members 2 are integrated with each other by three sharing linear portions 21 (first pattern sharing linear portion 21) or by three sharing linear portions 41 (second pattern sharing linear portion 41). The three sharing linear portions 21 are substantially equiangularly disposed in the axial direction of the stent 60. Similarly the three sharing linear portions 41 are substantially equiangularly disposed in the axial direction of the stent 60.

The sharing linear portions (first pattern sharing linear portion) 21 and the sharing linear portions (second pattern sharing linear portion 41) extend obliquely with respect to the axial direction of the stent 60 and are different from each other in the orientation thereof.

More specifically, in the stent 60, the termination point of the first pattern sharing linear portion 21 of one wavy annular member 2 is connected to the other-end side bent portion thereof by the linear portion 24. Similarly the termination point of the second pattern sharing linear portion 41 of one wavy annular member 2 is connected to the other-end side bent portion thereof by the linear portion 24. That is, in the stent 1, the linear portion 24 connects two sharing linear portions (exactly, termination point of sharing linear portion of one wavy annular member and start point of sharing linear portion of adjacent wavy annular member are connected to each other) adjacent to each other in the axial direction of the stent 1. On the other hand, in the stent 60, the linear portion 24 does not connect the sharing linear portions to each other. The linear portion 24 connected with the sharing linear portion is not formed as clearly as the long linear portion 24 of the stent 1. The linear portion 24 of the stent 60 is a little longer than other linear portions but may be formed as a long linear portion.

In the stent 60, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent are substantially equiangularly disposed with respect to the axis of the stent 60. Similarly two second pattern sharing linear portions 41 adjacent to each other in the axial direction of the stent are also substantially equiangularly disposed with respect to the axis of the stent 60. Therefore the stent 60 is capable of entirely displaying a substantially uniform expansive force.

As shown in FIG. 13, the stent 60 has 13 wavy annular members arranged in the axial direction thereof. The first pattern sharing linear portions 21 are spirally disposed in the axial direction thereof. Similarly the second pattern sharing linear portions 41 are spirally disposed in the axial direction thereof. More specifically, the adjacent wavy annular members are connected with each other by three first pattern sharing linear portions 21 or three second pattern sharing linear portions 41 alternating with the three first pattern sharing linear portions 21 in the axial direction of the stent 60. The first pattern sharing linear portion 21 are spirally disposed in the axial direction of the stent 60 to form three spirals. Each of the three spirals is composed of six first pattern sharing linear portions 21. Similarly the second pattern sharing linear portions 41 are spirally disposed in the axial direction of the stent 60 to form three spirals. Each of the three spirals is composed of six second pattern sharing linear portions 41.

As described above, the first pattern sharing linear portions 21 and the second pattern sharing linear portions 41 extend obliquely with respect to the axial direction of the stent 60 and are different from each other in the orientation thereof. It is preferable that the orientation of the first pattern sharing linear portion 21 and that of the second pattern sharing linear portion 41 are substantially symmetrical to each other with respect to the axis of the stent 60. Thereby the stent 60 is capable of entirely displaying a substantially uniform expansive force.

Describing the arrangement manner of the sharing linear portions in the axial direction of the stent 60, three first pattern sharing linear portions 21 are formed at uniform intervals in the circumferential direction of the stent. Three second pattern sharing linear portions 41 are formed adjacently to the first pattern sharing linear portions 21 at uniform intervals in the circumferential direction of the stent. Three second pattern sharing linear portions 41 are formed adjacently to the above-described second pattern sharing linear portions 41 at uniform intervals in the circumferential direction of the stent.

Three first pattern sharing linear portions 21 are formed adjacently to the above-described second pattern sharing linear portions 41 at uniform intervals in the circumferential direction of the stent. In this manner, the first pattern sharing linear portion 21 and the second pattern sharing linear portion 41 are arranged in the order of 21, 41, 41, 21, 21, 41, 41 . . . .

The construction of the stent 60 makes a resistance to an axial expansion and contraction of the wavy annular member smaller than the resistance thereto in the stent 1. Thereby the stent 60 has more favorable follow-up performance for deformation of blood vessels.

Figure 15:
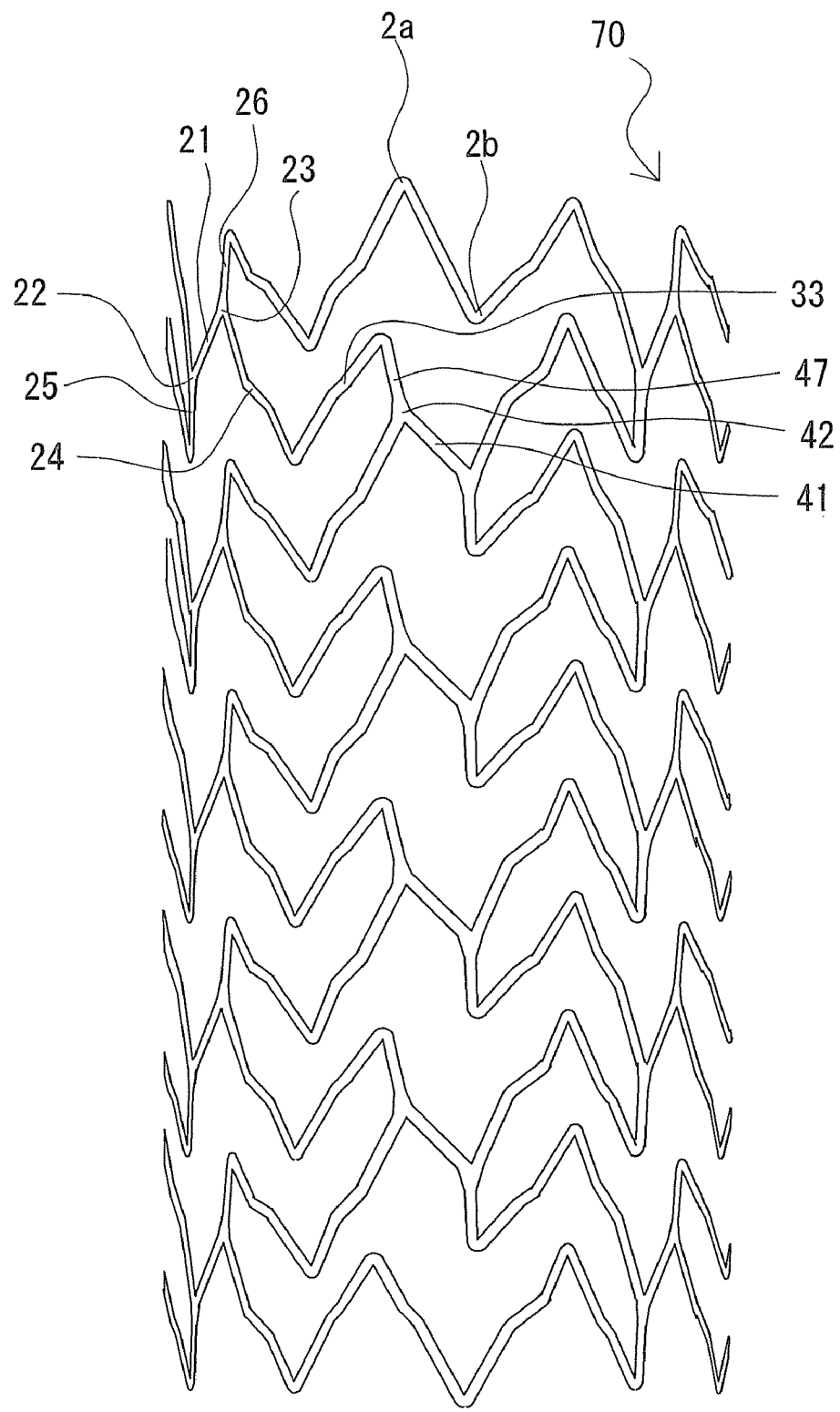
FIG. 15 is a front view showing still another embodiment of the stent of the present invention.
Figure 16:
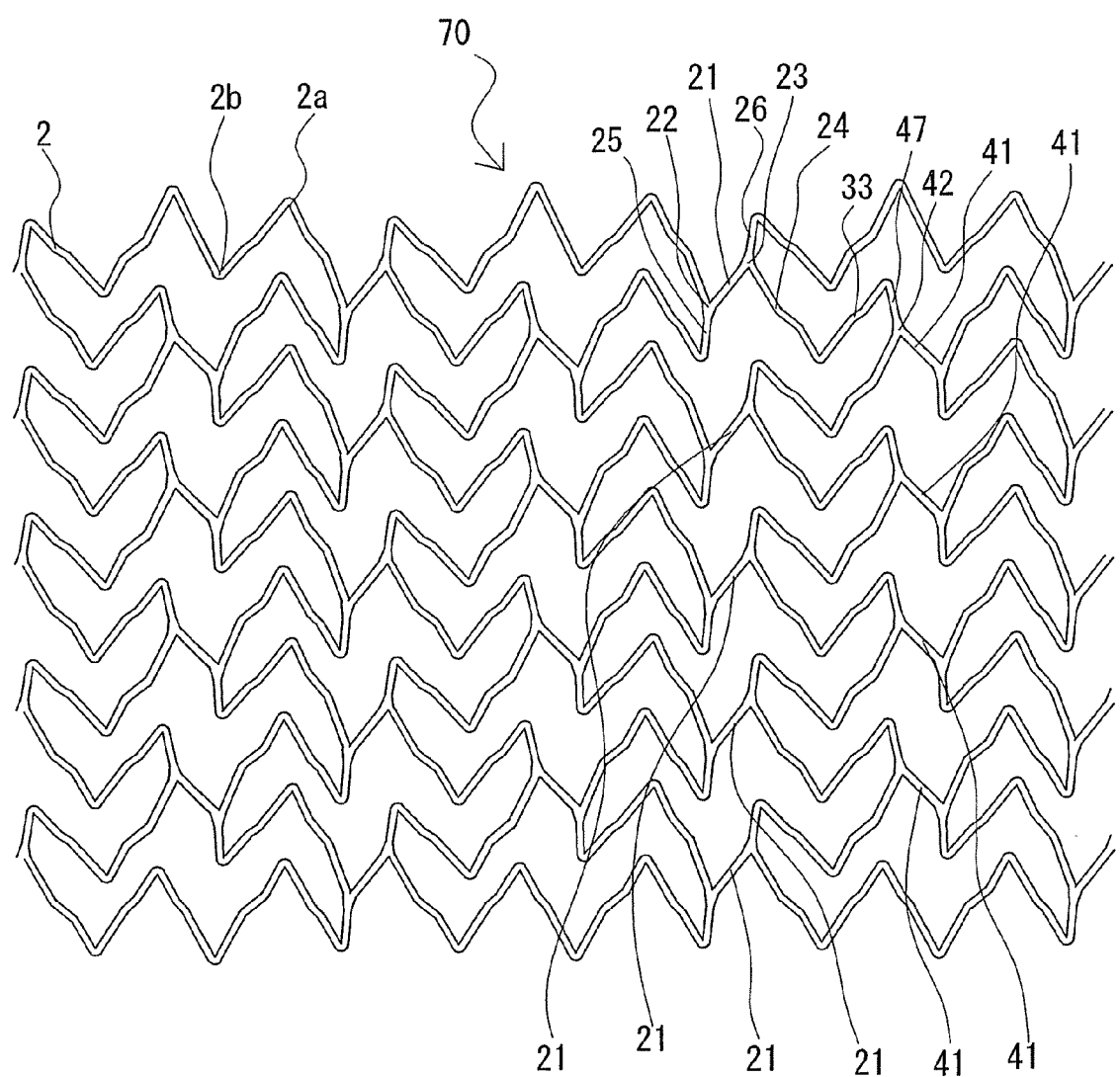
FIG. 16 is a development view showing the stent shown in FIG. 15.
Figure 17:
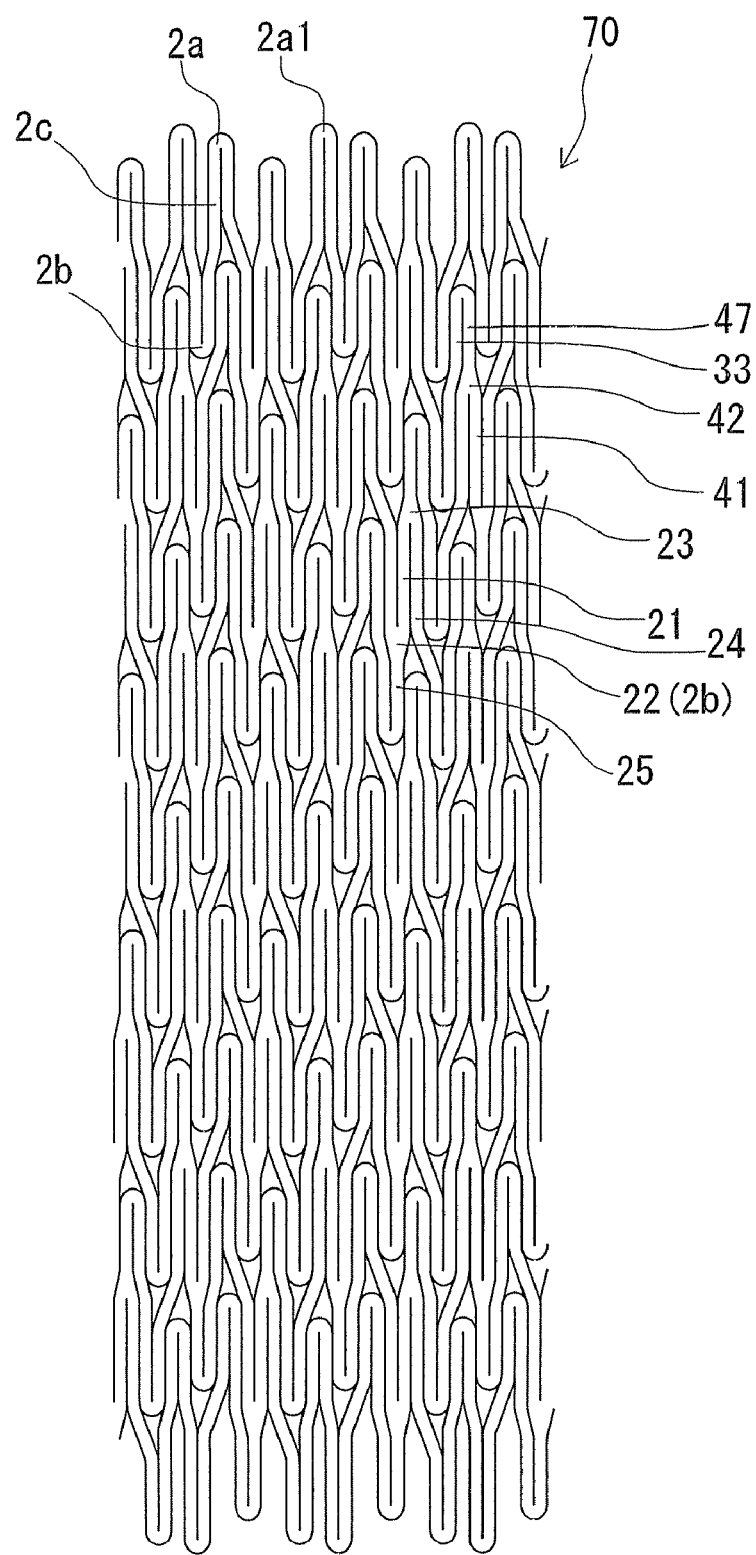
FIG. 17 is a development view showing the stent, shown in FIG. 15, when the stent is contracted.

The stent of the present invention may be formed as a stent 70 having a construction as shown in FIGS. 15 through 17. FIG. 15 is a front view showing still another embodiment of the stent of the present invention. FIG. 16 is a development view showing the stent shown in FIG. 15. FIG. 17 is a development view showing the stent, shown in FIG. 15, whose diameter is decreased.

The stent 70 has the same construction as that of the stent 1 except the arrangement form of the sharing linear portion and the orientation thereof.

In the stent 70, the number of the one-end side bent portions of one wavy annular member 2 and that of the other-end side bent portions thereof are equal to than that of the wavy annular member 2 of the stent 1. More specifically, the number of the one-end side bent portions of the wavy annular member 2 and that of the other-end side bent portions thereof are nine respectively. Ten wavy annular members 2 are disposed in the axial direction of the stent 70. The adjacent two wavy annular members 2 are integrated with each other by three sharing linear portions 21 (first pattern sharing linear portion 21) or three sharing linear portions 41 (second pattern sharing linear portion 41). The three sharing linear portions 21 are substantially equiangularly disposed in the axial direction of the stent 70. Similarly the three sharing linear portions 41 are substantially equiangularly disposed in the axial direction thereof.

In the stent 70, the sharing linear portions (first pattern sharing linear portion) 21 and the sharing linear portions (second pattern sharing linear portion) 41 are disposed alternately in the axial direction of the stent 70. Further, the first pattern sharing linear portions (first pattern sharing linear portion) 21 and the sharing linear portions (second pattern sharing linear portion) 41 are disposed uncontinuously with each other in the axial direction of the stent 70. More specifically, the sharing linear portion (second pattern sharing linear portion) 41 is shifted from the sharing linear portion (first pattern sharing linear portion) 21 in the circumferential direction of the stent 70. The sharing linear portions (first pattern sharing linear portion) 21 are formed substantially straight in the axial direction of the stent 70. Similarly the sharing linear portions (second pattern sharing linear portion) 41 are formed substantially straight in the axial direction of the stent 70.

In the stent 70, the first pattern sharing linear portion 21 and the second pattern sharing linear portion 41 extend obliquely with respect to the axial direction of the stent and are different from each other in the orientation thereof.

More specifically, in the stent 70, the termination point of the first pattern sharing linear portion 21 of one wavy annular member 2 is connected to the other-end side bent portion thereof by the linear portion 24. Similarly the termination point of the second pattern sharing linear portion 41 of one wavy annular member 2 is connected to the other-end side bent portion thereof by the linear portion 24. That is, in the stent 1, the long linear portion 24 connects two sharing linear portions (exactly, termination point of sharing linear portion of one wavy annular member and start point of sharing linear portion of adjacent wavy annular member are connected to each other) adjacent to each other in the axial direction of the stent 1. On the other hand, in the stent 70, the linear portion 24 does not connect the sharing linear portions to each other. The linear portion 24 connected with the sharing linear portion is not formed as clearly as the long linear portion 24 of the stent 1. The linear portion 24 of the stent 70 is a little longer than other linear portions but may be formed as a long linear portion.

In the stent 70, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent are substantially equiangularly disposed with respect to the axis of the stent 70. Similarly two second pattern sharing linear portions 41 adjacent to each other in the axial direction of the stent are also substantially equiangularly disposed with respect to the axis of the stent 70. Therefore the stent 70 is capable of entirely displaying a substantially uniform expansive force.

As described above, the first pattern sharing linear portions 21 and the second pattern sharing linear portions 41 extend obliquely with respect to the axial direction of the stent 70 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 70 is capable of entirely displaying a substantially uniform expansive force. Describing the arrangement manner of the sharing linear portions in the axial direction of the stent three first pattern sharing linear portions 21 are formed at uniform intervals in the circumferential direction of the stent. Three second pattern sharing linear portions 41 are formed adjacently to the first pattern sharing linear portions 21 at uniform intervals in the circumferential direction of the stent. Three first pattern sharing linear portions 21 are formed adjacently to the above-described second pattern sharing linear portions 41 at uniform intervals in the circumferential direction of the stent.

Three second pattern sharing linear portions 41 are formed adjacently to the above-described first pattern sharing linear portions 21 at uniform intervals in the circumferential direction of the stent. In this manner, the first pattern sharing linear portion 21 and the second pattern sharing linear portion 41 are arranged in the order of 21, 41, 21, 41, 21, 41, 21 . . . .

The construction of the stent 70 makes a resistance to an axial expansion and contraction of the wavy annular member smaller than the resistance thereto in the stent 1. Thereby the stent 70 has more favorable follow-up performance for deformation of blood vessels.

As shown in FIG. 16, the wavy annular member 2 of the stent 70 has a short linear portion 26 connecting the termination point 23 of the first pattern sharing linear portion 21 thereof and the apex 2a of the one-end side bent portion thereof to each other. As shown in FIG. 15, the wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 42 of the second pattern sharing linear portion 41 thereof and the apex of the one-end side bent portion thereof to each other.

Figure 18:
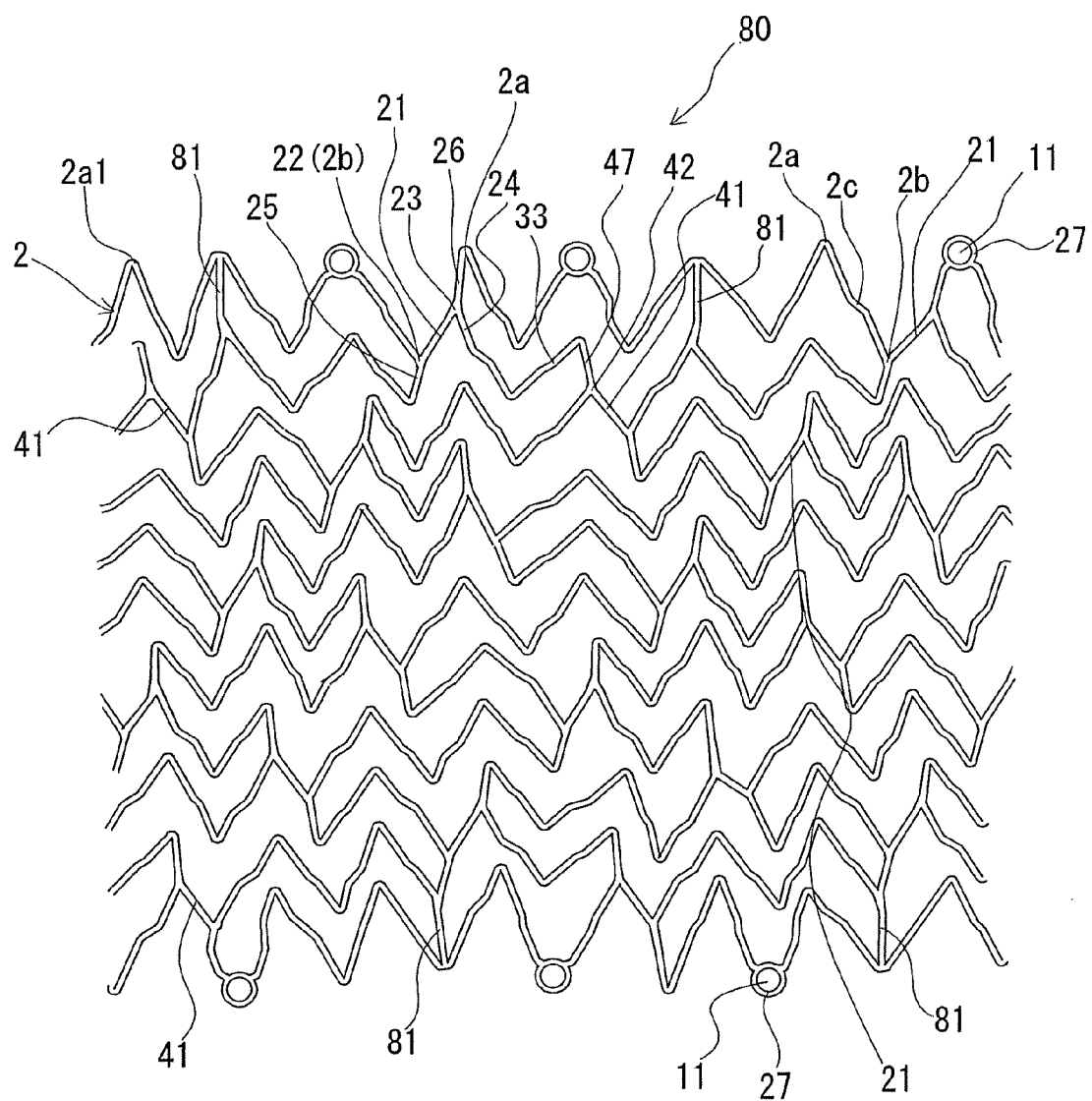
FIG. 18 is a development view showing still another embodiment of the stent of the present invention.
Figure 19:
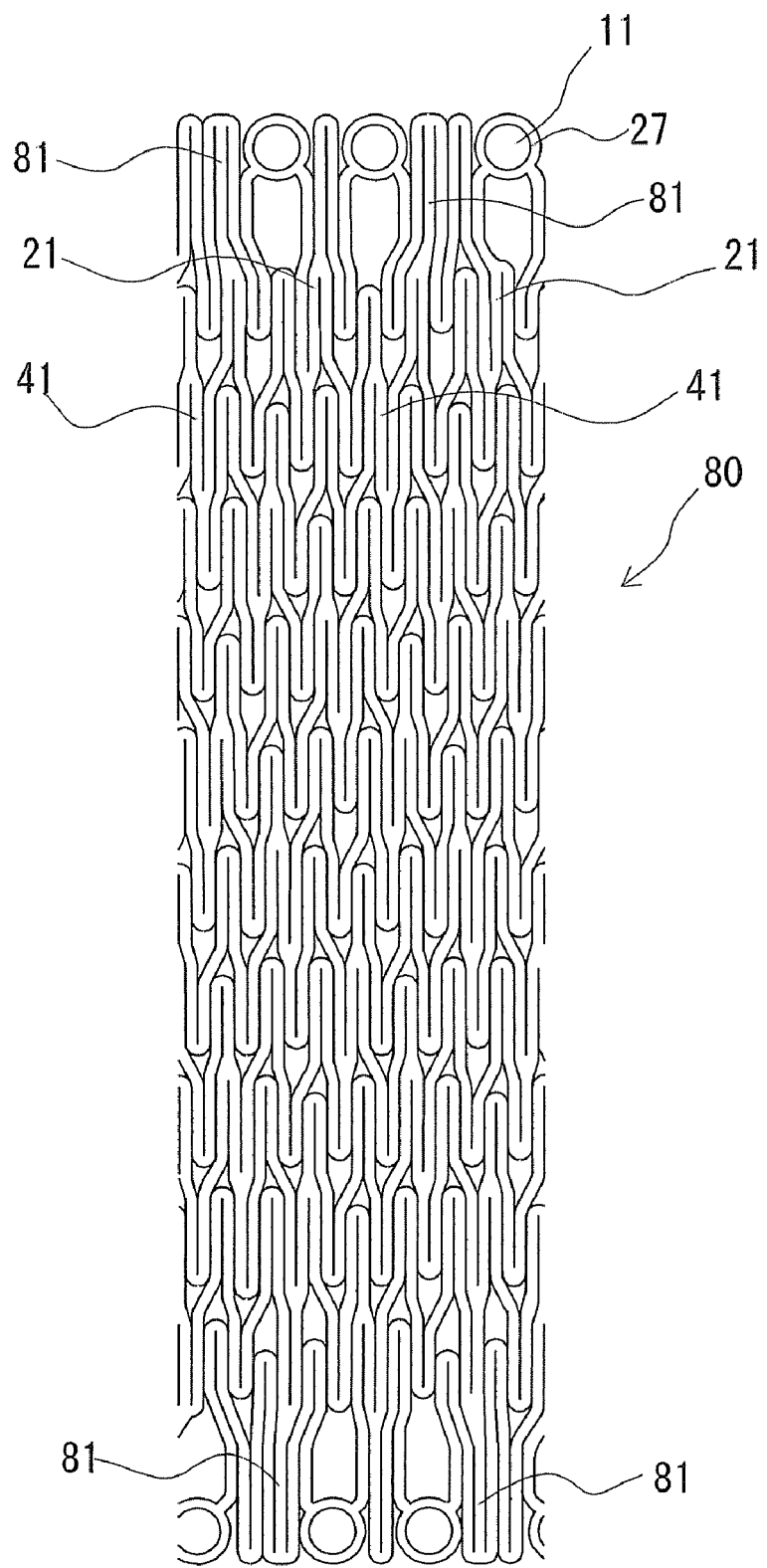
FIG. 19 is a development view showing the stent, shown in FIG. 18, when the stent is contracted.

The stent of the present invention may be formed as a stent 80 having a construction as shown in FIGS. 18 and 19. FIG. 18 is a front view showing still another embodiment of the stent of the present invention. FIG. 19 is a development view showing the stent shown in FIG. 18, when the stent contracted.

The stent 80 has the same construction as that of the stent 1 except the number of the one-end side bent portions of one wavy annular member, the number of the other-end side bent portions thereof, the number of the sharing linear portions integrating the adjacent wavy annular members with each other, the arrangement form of the sharing linear portions, the orientation thereof, the marker disposed at both ends of the stent and a coupling portion formed on the wavy annular member disposed at both ends of the stent.

The basic construction of the stent 80 is the same as that of the above-described stent 50.

The number of the one-end side bent portions of one wavy annular member 2 of the stent 50 and that of the other-end side bent portions thereof are smaller than that of one wavy annular member 2 of the stent 1. More specifically, the number of the one-end side bent portions of one wavy annular member 2 of the stent 80 and that of the other-end side bent portions of one wavy annular member 2 thereof are eight respectively. Eleven wavy annular members 2 are disposed in the anal direction of the stent 80. The adjacent two wavy annular members 2 are integrated with each other by two sharing linear portions 41 (first pattern sharing linear portion 21) or two sharing linear portions 41 (second pattern sharing linear portion 41). The two sharing linear portions 21 are opposed to each other with respect to the axis of the stent 80. Similarly the two sharing linear portions 41 are opposed to each other with respect to the axis of the stent 80.

In the stent 80, the first pattern sharing linear portion 21 and the second pattern sharing linear portion 41 are disposed alternately with respect to the axial direction thereof. Further, the first pattern sharing linear portion 21 and the second pattern sharing linear portion 41 are disposed uncontinuously with each other in the axial direction of the stent 80. More specifically, the second pattern sharing linear portion 41 is shifted from the first pattern sharing linear portion 21 in the circumferential direction of the stent 80.

In the stent 80, the first pattern sharing linear portion 21 and the second pattern sharing linear portion 41 extend obliquely with respect to the axial direction of the stent and are different from each other in the orientation thereof.

In the stent 80, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent and the two second pattern sharing linear portions 41 adjacent to each other in the axial direction thereof are substantially equiangularly disposed with respect to the axis thereof. Thereby the stent 80 is capable of entirely displaying a substantially uniform expansive force.

As shown in FIG. 18, in the stent 80, the first pattern sharing linear portions 21 are spirally disposed in the axial direction thereof. Similarly the second pattern sharing linear portions 41 are spirally disposed in the axial direction thereof.

As shown in FIG. 18, the stent 80 has 11 wavy annular members arranged in the axial direction thereof. The first pattern sharing linear portions 21 are spirally disposed in the axial direction thereof. Similarly the second pattern sharing linear portions 41 are spirally disposed in the axial direction thereof. More specifically, the adjacent wavy annular numbers are connected with each other by two first pattern sharing linear portions 21. The first pattern sharing linear portions 21 are spirally disposed in the axial direction of the stent 80 to form two spirals. Each of the two spirals is composed of five first pattern sharing linear portions 21. Similarly the adjacent wavy annular members (not connected by first pattern sharing linear portion 21) are connected with each other by two second pattern sharing linear portions 41. The second pattern sharing linear portions 41 are spirally disposed in the axial direction of the stent 80 to form two spirals. Each of the two spirals is constructed of five second pattern sharing linear portions 41.

As described above, the first pattern sharing linear portions 21 and the second pattern sharing linear portions 41 extend obliquely with respect to the axial direction of the stent 80 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 80 is capable of entirely displaying a substantially uniform expansive force.

As shown in FIG. 18, one wavy annular member 2 of the stent 80 has a short linear portion 26 connecting the termination point 23 of the first pattern sharing linear portion 21 thereof and the apex 2a of the one-end side bent portion thereof to each other. The wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 42 of the second pattern sharing linear portion 41 thereof and the apex of the one-end side bent portion thereof to each other.

Similarly to the stent shown in FIGS. 18 and 19, the stent 80 has a contrast marker 11. It is favorable to dispose the contrast marker 11 at an end of the stent 80. It is more favorable to dispose the contrast marker 11 at both ends of the stent. More specifically, as shown in FIGS. 18 and 19, it is preferable to dispose a plurality of the markers 11 at both ends of the stent. The stent 80 of this embodiment has an opening 27 formed at an apex disposed at both ends thereof. The marker 11 dosing the opening 27 is fixed to the ends of the stent. The contrast marker is the same as that of the above-described stent 10.

As shown in FIGS. 18 and 19, an outer edge of the opening 27 is coincident with outer edges of other apexes disposed at the end (upper and lower ends) of the stent in the axial direction thereof. That is, in the stent 80, the outer edge of the opening 27 to which the marker is fixed is not projected outward from the outer edges of the other apexes disposed at the end of the stent. By making the outer edges of the stent coincident with one another in the axial direction of the stent, the stent can be securely pressed out, even though the stent is curved. In the stent 80, the opening 27 is formed at an apex disposed at one end of the stent. The opening 27 has two leg portions extending toward other end of the stent. The two leg portions are spaced from each other and substantially parallel. In the stent 80, two leg portions are extended inward from a position located inward from an inner side of each opening 27 disposed at a bent portion, with the two leg portions spaced from each other at a predetermined interval. The two leg portions extended from the opening 27 are spaced from each other. That is, in the stent 80, the two leg portions extended from the opening 27 are not proximate to each other, unlike the leg portion of the stent 10 shown in FIG. 5. By spacing the two leg portions from each other at the predetermined interval, the configuration of the region in the vicinity of the marker-formed portion (opening 27) is stable. Therefore even though a strong force is applied to the region in the vicinity of the marker-formed portion (opening 27), the stent is prevented from deforming and can be reliably pressed out.

As shown in FIGS. 18 and 19, in the stent 80, the wavy annular member 2 disposed at both ends (upper and lower ends) of the stent is provided with a coupling portion 81 for coupling the wavy annular member 2 and the adjacent wavy annular member 2 to each other. In the stent 80, two coupling portions 81 are provided between the wavy annular member 2 disposed at both ends (upper and lower ends) of the stent and the adjacent wavy annular member 2. In the stent 80, coupling portion 81 is provided only between two wavy annular members 2 disposed at both ends (upper and lower ends) of the stent and the adjacent wavy annular member 2. The two coupling portions 81 are formed at positions opposed to each other with respect to the axis of the stent. As shown in FIGS. 18 and 19, at one end portion (upper end portion) of the stent 80, the two sharing linear portions 21 and the above-described two coupling portions 81 are disposed substantially equiangularly with respect to the axis of the stent. Similarly at the other end portion power end portion) of the stent 80, the two sharing linear portions 41 and the above-described two coupling portions 81 are disposed substantially equiangularly with respect to the axis of the stent.

Because the stent 80 has the sharing linear portions and the coupling portions at both end portions thereof, the form or the configuration of both end portions of the stent is stable after the stent expands. The above-described stent has two coupling portions at both end portions thereof. But the stent may have one or three coupling portions at both end portions thereof.

Because the stent 80 of this embodiment has a construction different from that of the stent 1, it has a comparatively low resistance to axial expansion and contraction thereof. Thereby the stent 80 has favorable follow-up performance for deformation of blood vessels.

Figure 20:
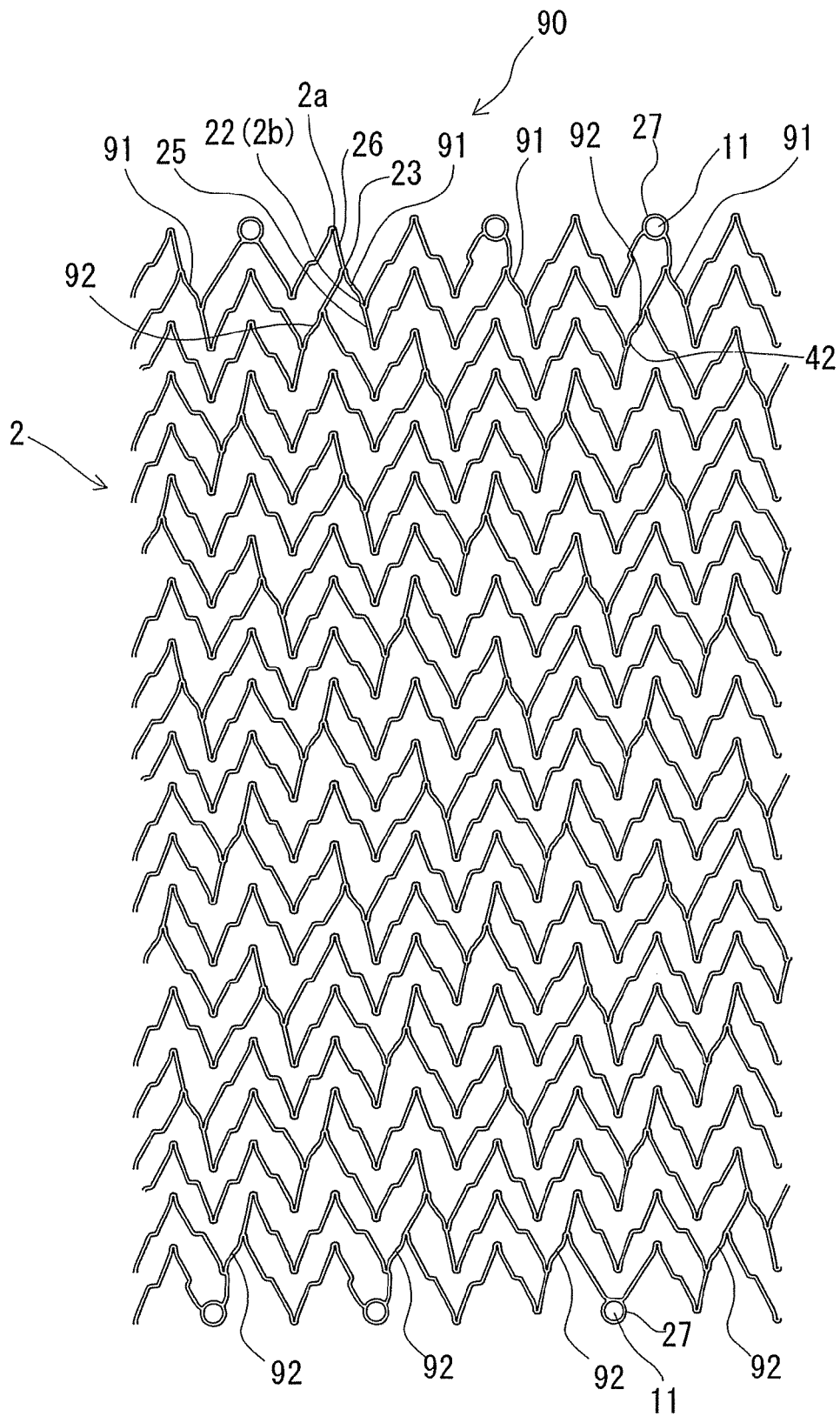
FIG. 20 is a development view showing still another embodiment of the stent of the present invention.
Figure 21:
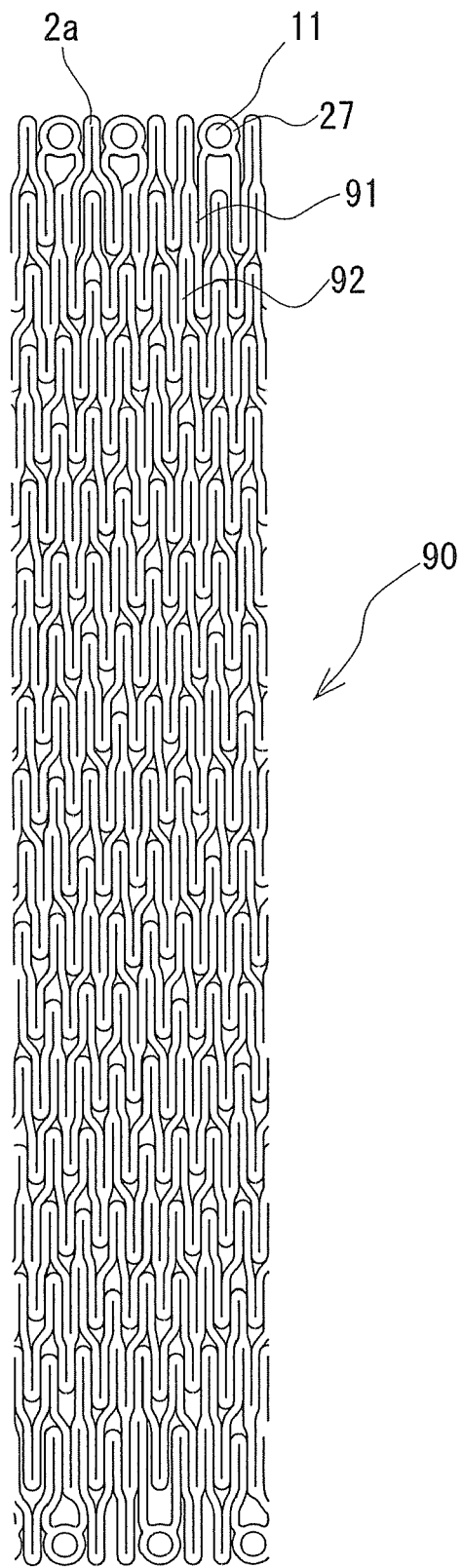
FIG. 21 is a development view showing the stent, shown in FIG. 20, when the stent is contracted.

The stent of the present invention may be formed as a stent 90 having a pattern as shown in FIGS. 20 and 21. FIG. 20 is a development view showing still another embodiment of the stent of the present invention. FIG. 21 is a development view showing the stent shown in FIG. 20, when the stent contracted.

The stent 90 has the same construction as that of the stent 1 except the number of the one-end side bent portions of one wavy annular member, the number of the other-end side bent portions thereof, the number of the sharing linear portions integrating the adjacent wavy annular members with each other, the arrangement form of the sharing linear portions, the orientation thereof, and the marker disposed at both ends of the stent.

The form of the stent 90 is similar to that of the above-described stent 50.

The number of the one-end side bent portions of one wavy annular member 2 of the stent 90 and that of the other-end side bent portions thereof are smaller than that of one wavy annular member 2 of the stent 1. More specifically, the number of the one-end side bent portions of one wavy annular member 2 of the stent 90 and that of the other-end side bent portions of one wavy annular member 2 thereof are eight respectively. In the axial direction of the stent 90, twenty-one wavy annular members 2 are disposed. In the stent 90, the adjacent two wavy annular members 2 are integrated with each other by two sharing linear portions 91 (first pattern sharing linear portion) or two sharing linear portions 92 (second pattern sharing linear portion). In the stent 90, the adjacent two wavy annular members 2 are integrated with each other by at least two sharing linear portions. The two sharing linear portions 91 are opposed to each other with respect to the axis of the stent 90. Similarly the two sharing linear portions 91 are opposed to each other with respect to the axis of the stent 90.

As shown in FIGS. 20 and 21, in the stent 90, the wavy annular member 2 disposed at both ends (upper and lower ends) of the stent and the adjacent wavy annular member 2 are integrated with each other with four sharing linear portions. At one end portion (upper end portion) of the stent 90, the above-described four sharing linear portions 91 are disposed substantially equiangularly with respect to the axis of the stent. Similarly, at the other end portion (lower end portion) of the stent 90, the above-described four sharing linear portions 92 are disposed substantially equiangularly with respect to the axis of the stent.

Because in the stent 90, a larger number of sharing linear portions are formed at both end portions of the stent than at other portions, the form or the configuration of both end portions of the stent is stable after the stent expands.

In the stent 90, the first pattern sharing linear portion 91 and the second pattern sharing linear portion 92 are disposed alternately with respect to the axial direction thereof. Further, the first pattern sharing linear portion 91 and the second pattern sharing linear portion 92 are disposed uncontinuously with each other in the axial direction of the stent 90. More specifically, the second pattern sharing linear portion 92 is shifted from the first pattern sharing linear portion 91 in the circumferential direction of the stent 90.

In the stent 90, the first pattern sharing linear portion 91 and the second pattern sharing linear portion 92 extend obliquely with respect to the axial direction of the stent and are different from each other in the orientation thereof.

In the stent 90, except both end portions thereof, one one-end side bent portion and one other-end side bent portion are disposed between the first pattern sharing linear portion 91 and the second pattern sharing linear portion 92 adjacent to the first pattern sharing linear portion 91 in the axial direction thereof. Two first pattern sharing linear portions 91 adjacent to each other in the axial direction of the stent and two second pattern sharing linear portions 92 adjacent to each other in the axial direction thereof are substantially equiangularly disposed with respect to the axis thereof. Thereby the stent 50 is capable of entirely displaying a substantially uniform expansive force.

As shown in FIG. 20, in the stent 90, the first pattern sharing linear portions 91 are spirally disposed in the axial direction thereof. Similarly the second pattern sharing linear portions 91 are spirally disposed in the axial direction thereof.

As shown in FIG. 20, the stent 90 has twenty-one wavy annular members arranged in the axial direction thereof. The first pattern sharing linear portions 91 are spirally disposed in the axial direction thereof. Similarly the second pattern sharing linear portions 92 are spirally disposed in the axial direction thereof. More specifically, the adjacent wavy annular members are connected with each other by two first pattern sharing linear portions 91. The first pattern sharing linear portions 91 are spirally disposed in the axial direction of the stent 90 to for, two spirals. Each of the two spirals is composed of first pattern sharing linear portions 91. Similarly the adjacent wavy annular members (not connected by first pattern sharing linear portion 91) are connected with each other by two second pattern sharing linear portions 92. The second pattern sharing linear portions 92 are spirally disposed in the axial direction of the stent 90 to form two spirals. Each of the two spirals is constructed of five second pattern sharing linear portions 92.

As described above, the first pattern sharing linear portions 91 and the second pattern sharing linear portions 91 extend obliquely with respect to the axial direction of the stent 90 and are different from each other in the orientation thereof. It is preferable that the orientation of the first pattern sharing linear portion 91 and that of the second pattern sharing linear portion 92 are substantially symmetrical to each other with respect to the axis of the stent. Thereby the stent 90 is capable of entirely displaying a substantially uniform expansive force.

As shown in FIG. 20, one wavy annular member 2 of the stent 90 has a short linear portion 26 connecting the termination point 23 of the first pattern sharing linear portion 91 thereof and the apex 2a of the one-end side bent portion thereof to each other. The wavy annular member adjacent to the wavy annular member 2 having the short linear portion 26 has a short linear portion 25 connecting the start point 22 of the first pattern sharing linear portion 91 thereof and the apex 2b of the other-end side bent portion thereof to each other and a short linear portion connecting a termination point of the second pattern sharing linear portion 41 thereof and the apex of the one-end side bent portion thereof to each other.

As shown in FIGS. 20 and 21, the stent 90 has a contrast marker 11. It is favorable to dispose the contrast marker 11 at an end of the stent 80. It is more favorable to dispose the contrast marker 11 at both ends of the stent. More specifically, as shown in FIGS. 20 and 21, it is preferable to dispose a plurality of the markers 11 at both ends of the stent. The stent 90 of this embodiment has an opening 27 formed at an apex disposed at both ends of the stent. The marker 11 closing the opening 27 is fixed to the ends of the stent. The contrast marker is the same as that of the above-described stent 10.

As shown in FIGS. 20 and 21, an outer edge of the opening 27 is coincident with outer edges of other apexes disposed at the end (upper and lower ends) of the stent in the axial direction thereof. That is, in the stent 90, the outer edge of the opening 27 to which the marker is fixed is not projected outward from the outer edges of the other apexes disposed at the end of the stent. By making the outer edges of the stent coincident with one another in the axial direction of the stent the stent can be securely pressed out even though the stent is curved. In the stent 90, two leg portions are extended inward from a position located inward from an inner side of each opening 27 disposed at a bent portion, with the two leg portions spaced from each other at a predetermined interval. The two leg portions extended from the opening 27 are spaced from each other. That is, in the stent 90, the two leg portions extended from the opening 27 are not proximate to each other, unlike the leg portion of the stent 10 shown in FIG. 5. By spacing the two leg portions from each other at the predetermined interval, the configuration of the region in the vicinity of the marker-formed portion (opening 27) is stable. Therefore when a strong force is applied to the region in the vicinity of the marker-formed portion (opening 27), the stent is prevented from deforming and can be reliably pressed out.

The outer diameter, thickness, and length of the stent are different respectively in dependence on a portion where the stent is implanted. When the stent is expanded (when it is not contracted in its diameter and when it is restored to its original state), the outer diameter thereof is favorably in the range of 2.0 to 30 mm and more favorably in the range of 2.5 to 20 mm; the thickness thereof is favorably in the range of 0.04 to 1.0 mm and more favorably in the range of 0.06 to 0.5 mm; and the length thereof is favorably in the range of 10-150 mm and more favorably in the range of 15 to 100 mm. In the case of the stent to be implanted in the blood vessel, the outer diameter thereof is favorably in the range of 2.0 to 14 mm and more favorably in the range of 2.5 to 12 mm; the thickness thereof is favorably in the range of 0.04 to 0.3 mm and more favorably in the range of 0.06 to 0.22 mm; and the length thereof is favorably in the range of 5-100 mm and more favorably in the range of 10 to 80 mm.

The stent is integrally and cylindrically made of the super-elastic alloy showing super-elasticity before and after the stent is inserted into the organism.

The super-elastic alloy can be preferably used as the super-elastic metal. Herein the super-elastic alloy means a so-called shape memory alloy that shows super-elasticity essentially at the temperature (in the vicinity of 37□) of the organism. The following super elastic metals can be favorably used: A Ti—Ni alloy of 49-54 atomic percent of Ni, a Cu—Zn alloy of 38.5-41.5 wt % of Zn, a Cu—Zn—X alloy of 1-10 wt % of X (X═Be, Si, Sri, Al, Ga), and a Ni—Al alloy of 36-38 atomic percent of Al. The Ti—Ni alloy is most favorable. The mechanical characteristic of the Ti—Ni alloy can be appropriately changed by replacing a part of the Ti—Ni alloy with 0.01-10.0% of X to obtain a Ti—Ni—X alloy (X═Co, Fe, Mn, Cr, V, Al, Nb, W, B, Au, and Pd) or by replacing a part of the Ti—Ni alloy with 0.01-30.0 atomic percent of X to obtain a Ti—Ni—X alloy (X=Cu, Pb, Zr). Further the mechanical characteristic of the super-elastic alloy can be appropriately changed by selectively adopting a cold working ratio or/and the condition of final heat treatment.

In the case where the Ti—Ni—X alloy is used, it is also possible to change the mechanical characteristic of the super-elastic alloy appropriately by selectively adopting the cold working ratio or/and the condition of the final heat treatment The buckling strength (yield stress when load is applied to stent) of the super-elastic alloy to be used is favorably in the range of 5-200 kg/mm$^2$ (22° C.) and more favorably in the range of 8-150 kg/mm$^2$. The restoring stress (yield stress when load is eliminated from stent) of the superelastic alloy is favorably in the range of 3-180 kg/mm$^2$ (22° C. and more favorably in the range of 5-130 kg/mm$^2$. The super-elasticity means that when a metal is deformed (bent stretched, compressed) to a region in which it deforms plastically at a service temperature, it returns to its original configuration substantially without heating it after an applied load is eliminated.

The stent is formed by removing (for example, cutting, dissolving) a part of a pipe made of the super-elastic metal, not constituting the stent. Thereby the stent is obtained as an integral product. The pipe made of the super elastic metal to be used to form the stent of the present invention can be produced by dissolving the super-elastic alloy such as the Ti—Ni alloy in an inactive gas atmosphere or a vacuum atmosphere to form an ingot thereof, polishing the ingot mechanically, forming a pipe having a large diameter by hot press and extrusion, repeating a drawing step and a heat treatment step to adjust the diameter and thickness of the pipe to a predetermined thickness and reduced diameter, and finally polishing the surface of the pipe chemically or physically. The pipe made of the super-elastic metal can be processed into the base material for the stent by a cutting work such as laser processing (for example, YAG laser), electrical discharge machining, chemical etching, cutting processing or in combination thereof.

The stent of the present invention may be coated with a material suitable for the organism on its inner surface, outer surface or inner and outer surfaces. As the material suitable for the organism, synthetic resin and metal suitable for the organism can be used. The following inactive metals are used to coat the surface of the stent gold by an electroplating method, stainless steel by an evaporation method, silicon carbide by a sputtering method, diamond-like carbon, plated titanium nitride, and plated gold. As the synthetic resin, the following thermoplastic resins or thermosetting resins can be used: polyolefin (for example, polyethylene, polypropylene, ethylene-propylene copolymer), polyvinyl chloride, ethylene-vinyl acetate copolymer, polyamide elastomer, polyurethane, polyester, fluorocarbon resin, silicone resin. It is preferable to use polyolefin, polyamide elastomer, polyester, polyurethane, silicone resin. A resin decomposable in the organism (polylactic acid, polyglycolic acid, polylactic acid-polyglycolic acid copolymer) is also favorable. It is preferable that a film of the synthetic resin is soft such an extent as not to prevent a frame constituting the stent from being curved. The thickness of the film of the synthetic resin is favorably in the range of 3 to 300 μm and more favorably in the range of 5 to 100 μm.

As the method of thinly coating the surface of the stent with the synthetic resin, it is possible to use a method of inserting the stent into the melted synthetic resin or into the synthetic resin dissolved in a solution. It is also possible to use a chemical evaporation method of polymerizing a monomer over the surface of the pipe made of the super-elastic metal. In the case where the surface of the stent is coated very thinly with the synthetic resin, the use of a dilute solution or the chemical evaporation method is preferable. To improve the quality of the material suitable for the organism to a higher extent the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, a copolymer of hydroxyethyl methacrylate and styrene (for example, HEMA-St-HEMA block copolymer) can be preferably used.

The stents of the above-described embodiments are formed as a tube, have a diameter whose dimension is so set that it can be inserted into the lumen of the predetermined portion inside the organism, and can be expanded when a force spreading radially outwardly from the inside of the tube is applied thereto. That is, the stent may be the balloon expandable stent.

It is preferable that the material of the balloon expandable stent has a certain degree of compatibility with the organism. For example, it is possible to use stainless steel tantalum or tantalum alloys, platinum or platinum alloys, gold or gold alloys, cobalt based alloys, a cobalt-chrome alloy, a titanium alloy, and a niobium alloy.

It is preferable to plate the stent with a noble metal such as gold and platinum after the stent is fabricated into a final shape. As the stainless steel, SUS 316L most corrosion-resistant can be preferably used.

It is preferable to anneal the stent after it is fabricated into the final shape. Annealing improves the flexibility and plasticity of the entire stent. Thereby the stent can be favorably implanted at a curved portion of a blood vessel. As compared with a non-annealed stent the annealed stent has a lower force of restoring to an original state after it is expanded, and especially has a lower force of restoring to an original linear state when it is expanded at the curved portion of the blood vessel. This minimizes physical stimulation to the inner wall of the curved portion of the blood vessel, thus reducing the cause of a recurrence of stenosis. It is preferable to anneal the stent by heating it to 900 to 1200° C. in an inert gas atmosphere (e.g., a mixture gas of nitrogen and hydrogen) so that no oxide film is formed on the surface of the stent and then slowly cooling it.

The stent has a diameter favorably 0.8 to 1.8 mm and more favorably 0.9 to 1.6 mm in an unexpanded state. The stent has a length favorably 8 to 40 mm in an unexpanded state. It is preferable that each wavy annular members has a length of 8 to 25 mm. It is preferable that the length of each connection portion 3 is 20-100 mm.

The stent is shaped by removing portions other than a frame structure from a tube (more specifically, metal pipe). More specifically, the stent is formed by removing unnecessary portions from the metal pipe by an etching process, known as photo-fabrication, using masks and chemicals; cutting processing (for example, mechanical polishing laser cutting processing), electric discharge machining, and in addition, by using the above-described methods in combination.

It is preferable to provide the stents of the above-described embodiments with a marker 11 as in the case of the stent 10 shown in FIG. 5. It is favorable to dispose the marker 11 at an end of each stent It is more favorable to dispose the marker 11 at both ends of the stent. More specifically, as shown in FIG. 5, it is preferable to dispose a plurality of the markers 11 at both ends of the stent. The marker is as described above.

EXAMPLES

The examples of the stent of the present invention are described below.

Example 1

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 3 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 3.

As the laser machining condition for the metal pipe, an average output and a drive speed were set to 5.5 W and 180 mm/minute respectively, The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 1 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm. The length of the long linear portion was about 3.4 mm.

The stent had a sufficient expansive force. Further a strain did not concentrate on a connection portion.

Example 2

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 11 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 11.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 9 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm.

The stent had a sufficient expansive force. Further a strain did not concentrate on a connection portion.

Example 3

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super elastic metal pipe was set on a jig, provided with a rotary motor, which had a fastening mechanism for preventing the metal pipe from being off-entered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 14 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 14.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 12 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.22 mm. The width of the linear portion of each wavy linear member was about 0.11 mm. The axial length of the wavy annular member was about 3 mm. The length of the sharing linear portion was about 1.6 mm.

The stent had a sufficient expansive force. Further a strain did not concentrate on a connection portion.

Example 4

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 17 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 17.

As the laser machining condition for the metal pipe, an average output and a drive speed were set to 5.5W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 15 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm.

The stent had a sufficient expansive force. Further a strain did not concentrate on a connection portion.

Experiment

The stent is implanted at various portions of lumens of an organism. Thus functions of the stent are different from one another in dependence on portions of the lumens. It is preferable that the stent has a comparatively high resistance to axial expansion and contraction thereof and is strong when the stent is implanted in the carotid artery and the renal artery. This is because these blood vessels expand and contract to a low extent for a movement of the organism. Therefore it is preferable to use the stent which expands and contracts to a low extent and holds the blood vessels firmly.

The superficial femoral artery and the popliteal artery expand and contract to a high extent for a movement of the organism. Further in many cases, because a lesion in the lower limbs is long, it is necessary to implant a long stent in these blood vessels. In this case, the stent is demanded to have a comparatively low resistance to axial expansion and contraction thereof and be axially flexible. As a result of energetic researches of the present inventors, they have developed stents having approximately the same constructions but different resistances (flexibilities) to the axial expansion and contraction thereof.

The resistance of each of the stents of the examples 1 through 4 to the axial expansion and contraction thereof was measured. More specifically, the resistance of each stent having an outer diameter of 8 mm and a length of 45 mm was measured when it was contracted by 20% of the remaining length of 30 mm, namely, by 6 mm, with each stent held at a position thereof spaced at 7.5 mm from both ends thereof.

TABLE 1

| Stent | Example 1 | Example 2 | Example 3 | Example 4 |
|---|---|---|---|---|
| Resistance | 43.5 gf | 11.5 gf | 18.3 gf | 17.2 Rf |

The results indicate that the stent of the example 1 had a comparatively high resistance to the axial expansion and contraction thereof and held blood vessels firmly. Thus the stent of the example 1 is suitable for being implanted in the carotid artery, the renal artery, and the like. The reason the resistance of the stent of the example 1 to the axial expansion and contraction thereof is comparatively high is because the long linear portion 24 is spirally continuous through two bent portions, namely, through the start point 22 and the termination point 23.

The stent of the examples 2 through 4 had a resistance not more than the half of that of the stent of the example 1 to the axial expansion and contraction thereof. Thus these stents are suitable for being implanted in the arteries of the lower limbs such as the superficial femoral artery, the popliteal artery, and the like. The reason the resistance of these stents to the axial expansion and contraction thereof is comparatively low is because they do not have a clear long linear portion and because the sharing linear portions are uncontinuous. The stent of the example 2 has only two sharing linear portions spaced by 180 degrees (opposed to each other with respect to the axis of the stent). Therefore the stent of the example 2 showed the lowest resistance.

The stent of the present invention to be implanted in the organism includes a plurality of the wavy annular members arranged in the axial direction thereof. In this construction, each of the wavy annular members has a plurality of the one-end side bent portions each having the apex at the one-end side of the stent in the axial direction thereof and a plurality of other-end side bent portions each having the apex at the other-end side of the stent in the axial direction thereof. In the wavy annular members disposed adjacently to each other in the axial direction of the stent the wavy annular member disposed at the one-end side of the stent in the axial direction thereof has the sharing linear portion having the start point at the apex of one of the other-end side bent portions thereof or in the vicinity of the apex and the termination point between the apex of the other-end side bent portion thereof and the apex of one of the one-end side bent portions thereof. The sharing linear portion integrates the adjacent wavy annular members with each other. The stent does not substantially display an expansive force or a connection portion having a possibility of adversely affecting the performance of the stent when the stent is curved. Further the adjacent wavy linear members are integrated with each other with the sharing linear portion. Therefore the stent has a sufficient and uniform expansive force.

Figure 22:
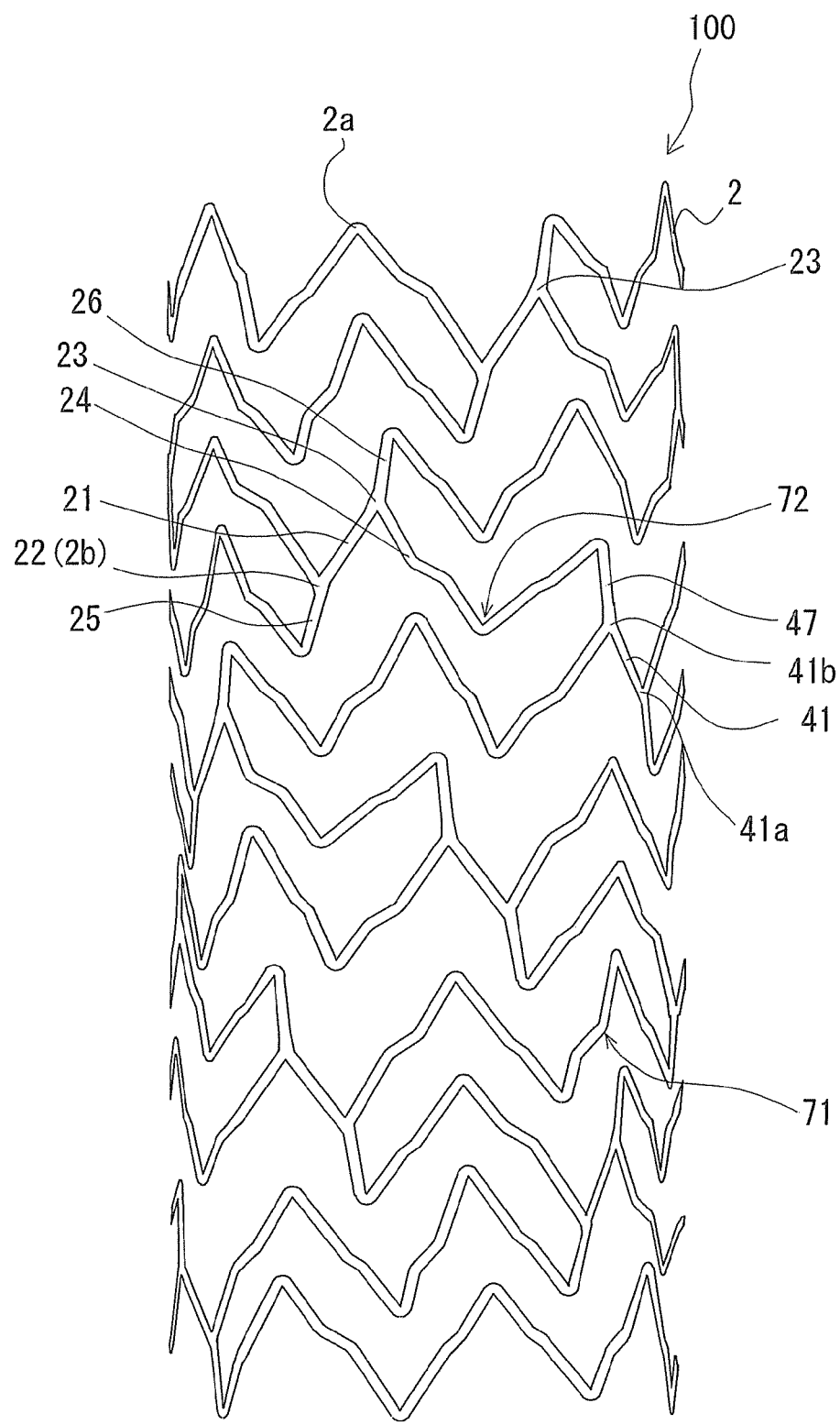
FIG. 22 is a front view showing a stent of another embodiment of the present invention.
Figure 23:
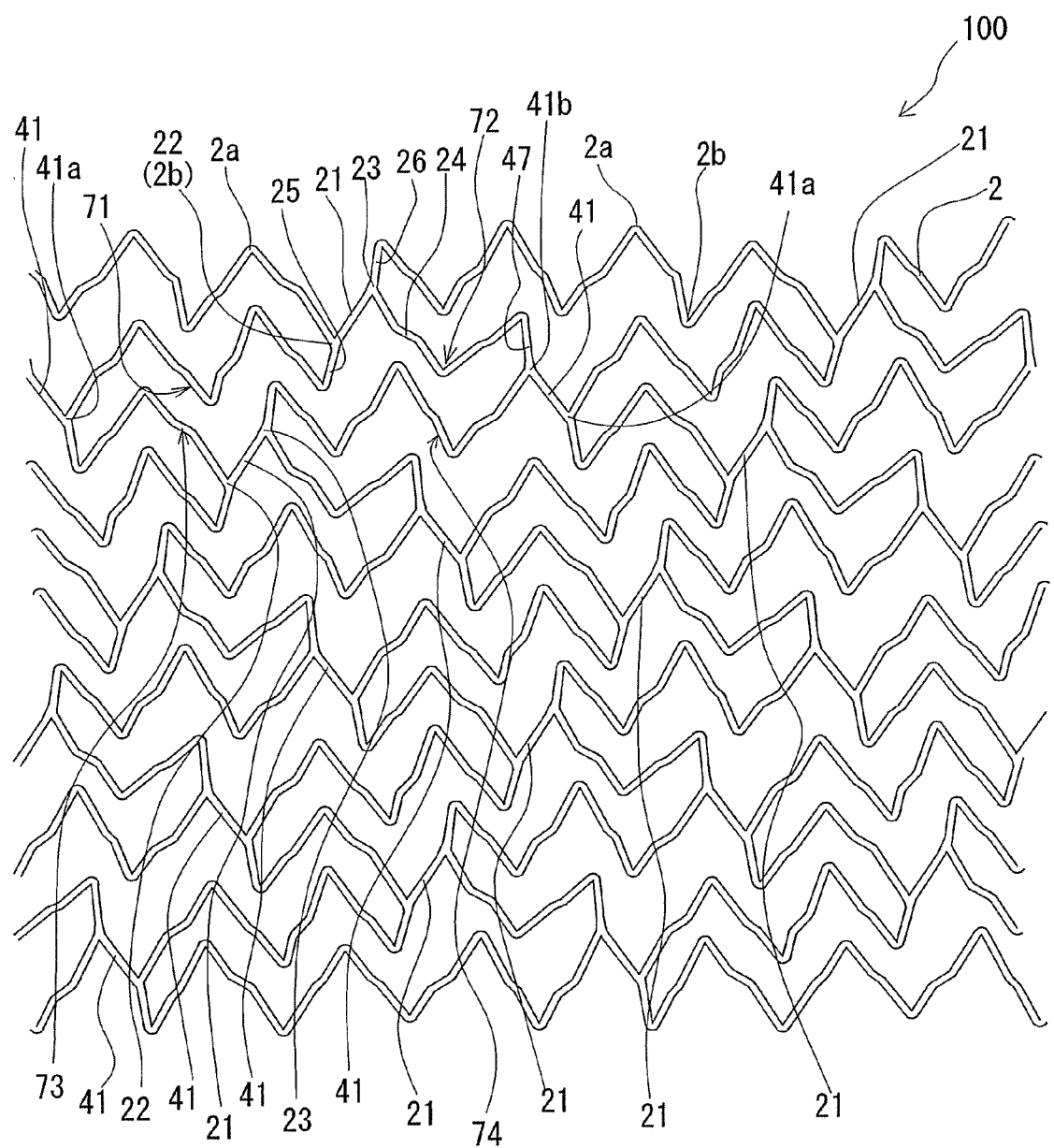
FIG. 23 is a development view showing the stent shown in FIG. 22.
Figure 24:
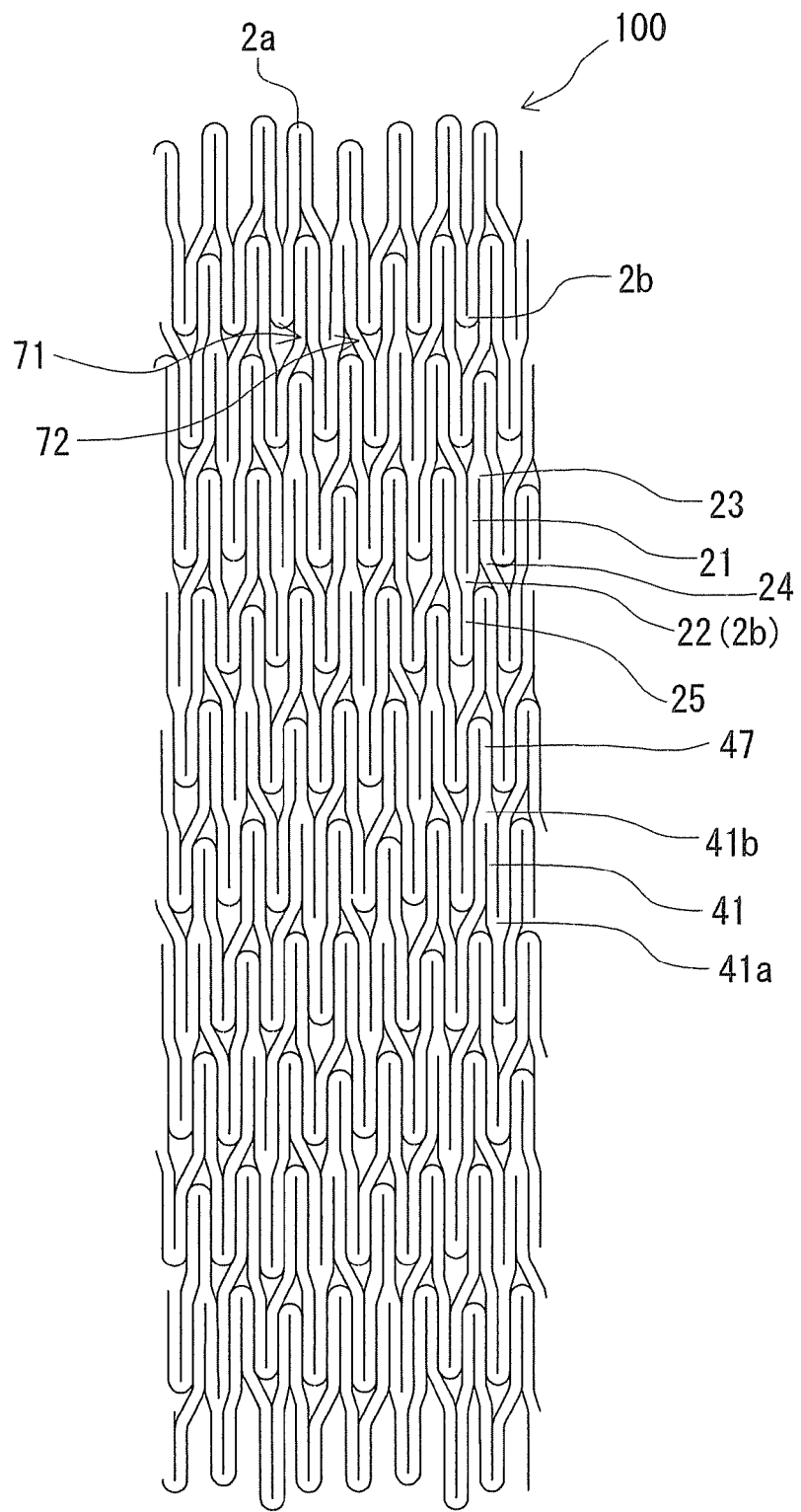
FIG. 24 is a development view showing the stent, shown in FIG. 22, when the stent is contracted.

FIG. 22 is a front view showing a stent of another embodiment of the present invention. FIG. 23 is a development view showing the stent shown in FIG. 22. FIG. 24 is a development view showing the stent, shown in FIG. 22, when the stent is contracted.

The self-expandable stent 100 of the present invention is formed approximately cylindrically and integrally from a metal pipe to which super-elastic property can be imparted, by removing a part of the metal pipe other than a part thereof corresponding to a linear portion constituting the stent. The stent 100 shows the super-elastic property before and after the stent is inserted into the organism. The line width of the linear portion of the stent 100 is set to 100 to 170 μm. The thickness of the linear portion is set to 180 to 230 μm.

A compression load for compressing the axial length of the stent by 20% is 10 to 20 gf. In other words, the stent of the present invention can be axially compressed by 20% by applying the compression load of 10 to 20 gf thereto.

It is preferable that the stent of the present invention can be axially compressed by 20% by applying the compression load of 12 to 14 gf thereto. It is also preferable that the stent of the present invention can be axially compressed by not less than 20% by applying the compression load of 10 to 20 gf thereto.

As shown in FIGS. 22, 23, and 24, the self-expandable stent 100 of this embodiment has a plurality of wavy annular members 2 arranged in an axial direction thereof. Each of the wavy annular members 2 has a plurality of one-end side bent portions each having an apex 2a at a one-end side of the stent 100 in the axial direction thereof and a plurality of other-end side bent portions each having an apex 2b at an other-end side of the stent 100 in the axial direction thereof. In the wavy annular members disposed adjacently to each other in the axial direction of the stent, the wavy annular member disposed at the one-end side of the stent in the axial direction thereof has a sharing linear portion 21 having a start point 22 at the apex 2b of one of the other-end side bent portions thereof or in the vicinity of the apex 2b and a termination point 23 between the apex 2b of the other-end side bent portion thereof and the apex 2a of one of the one-end side bent portions thereof. The sharing linear portion 21 integrates the adjacent wavy annular members with each other.

The stent of the present invention has the partial sharing portions which integrate adjacent wavy annular members with each other respectively. That is, the stent does not have a portion serving as only a connection portion of connecting the adjacent wavy annular members with each other, but is composed of portions each displaying an expansive force. The stent is composed of only deformable portions when the stent is contracted. Therefore the stent can be compressed at a small load.

The stent 100 is the so-called self-expandable stent which is formed substantially cylindrically, decreased in its diameter when it is inserted into the organism, and is capable of returning to a configuration before its diameter is decreased, when it is implanted in the organism. FIG. 22 shows the outlook of the stent 100 when it is expanded.

The number of the wavy annular members 2 forming the stent 100 shown in FIG. 22 is set to 11. The number of the wavy annular members 2 is favorably in the range of 2 to 150 and more favorably in the range of 5 to 100, although the number thereof is different in dependence on the length of the stent.

Each of the wavy annular members 2 has a plurality of the one-end side bent portions each having the apex at one-end side of the stent 100 in the axial direction thereof and a plurality of the other-end side bent portions each having the apex at the other-end side of the stent 100 in the axial direction thereof. In addition, each of the wavy annular members 2 is composed of an endless wavy line element. The one-end side bent portions and the other-end side bent portions of each of the wavy annular members 2 are formed alternately. The number of the one-end side bent portions and that of the other-end side bent portions are equal to each other. The number of the one-end side bent portions (other-end side bent portions) of each of the wavy annular members 2 shown in FIG. 22 is set to eight.

The number of the one-end side bent portions (other-end side bent portions) thereof is favorably in the range of 4 to 20 and more favorably in the range of 6 to 12. The wavy line element composing the wavy annular member 2 of the stent 100 of this embodiment curves and has only a few straight portions. The wavy line element forming the annular member 2 has a sufficiently large length, thus displaying a high expansive force when the stent 100 expands. The axial length of the wavy annular member 2 is favorably in the range of 1 to 100 mm and more favorably in the range of 1.5 to 5 mm.

The one-end side wavy annular members 2 adjacent to the other-end side wavy annular member 2 in the axial direction of the stent 100 has a sharing linear portion 21 having the start point 22 at the apex 2b of one of the other-end side bent portions thereof or in the vicinity of the apex 2b and the termination point 23 between the apex 2b of the other-end side bent portion thereof and the apex 2a of one of the one-end side bent portions thereof. The sharing linear portion 21 integrates the adjacent wavy annular members with each other.

More specifically, as shown in FIGS. 22 and 23, the sharing linear portion 21 has its start point 22 at the apex 2b of one of the other-end side bent portions of the wavy annular members 2 disposed at the one-end side of the stent 100 in the axial direction thereof. The start point 22 is coincident with the apex 2b. The sharing linear portion 21 has its termination point 23 between the above-described apex 2b and the apex 2a of one of the one-end side bent portions thereof continuous with the apex 2b (coincident with start point 22). In this embodiment the sharing linear portion 21 has its termination point in the vicinity of approximately the midpoint between the apex 2b (coincident with start point 22) of the other end-side bent portion and the apex 2a of the one-end side bent portion continuous with the apex 2b. It is preferable to dispose the termination point 23 at the midpoint between the apexes 2b and 2a. But the termination point 23 may be shifted to the side of the apex 2a or to the side of the apex 2b with respect to the midpoint by 1/100 to 49/100 of the whole length between the apex 2b (or start point 22) and the apex 2a of the one-end side bent portion continuous with the apex 2b. But in this case, it is preferable that the termination point 23 is shifted to the side of the apex 2a with respect to the midpoint.

Because the stent 100 has the above-described construction, the stent 100 has a bifurcating portion (in other words, start point bifurcating portion) formed by a start point of the sharing linear portion 21 and a bifurcating portion (in other words, termination point bifurcating portion) formed by a termination point of the sharing linear portion 21. More specifically, the start point bifurcating portion bifurcates toward the one-end of the stent 100 from the start point 22 serving as a bifurcation point. The termination point bifurcating portion bifurcates toward the other-end of the stent 100 from the termination point 23 serving as a bifurcation point.

As shown in FIG. 23, in the stent 100 of this embodiment each wavy annular member 2 has a short linear portion 26 connecting the termination point 23 of the sharing linear portion 21 thereof and the apex 2a of the one-end side bent portion thereof to each other. As shown in FIG. 23, the wavy annular member 2 integrated with the adjacent wavy annular member 2 having the short linear portion 26 by means of the sharing linear portion 21 has a short linear portion 25 connecting the start point 22 of the sharing linear portion 21 and the apex 2b of the other-end side bent portion thereof to each other and a long linear portion 24 connecting the termination point 23 of the sharing linear portion 21 and the other apex 2b of the other-end side bent portion thereof to each other.

The stent 100 does not have any connection portions. Thus the stent does not have interruptions of curvature or deterioration in the expansive force caused by the formation of the connection portion. Thereby the stent displays a uniform expanded state retention force.

The stent 100 of this embodiment has a plurality of sharing linear portions 21 between the wavy annular members 2 adjacent to each other in the axial direction thereof. More specifically, two sharing linear portions 21 are formed between the adjacent wavy annular members 2. The two sharing linear portions 21 are substantially opposed to each other with respect to the axis of the stent 100.

As shown in FIG. 23, the apex 2a of each of the one-end side bent portions of each wavy annular member 2 penetrates into a space formed between the apexes 2b of the adjacent other-end side bent portions of one of the adjacent wavy annular members 2. The apex 2b of each of the other-end side bent portions of each wavy annular member 2 penetrates into a space formed between the apexes 2a of the adjacent one-end side bent portions of the other of the adjacent wavy annular members 2.

When the stent 100 of this embodiment contracts, as shown in FIG. 24, wavy line elements are arranged, with gaps very little present in the circumferential direction of the stent 100. Therefore the stent 100 has a high coverage.

It is preferable to provide the stent shown in FIGS. 31, 32, 33 and 35 with a contrast marker 11. It is favorable to dispose the contrast marker 11 at an end of the stent. It is more favorable to dispose the marker 11 at both ends of the stent. More specifically, as shown in FIG. 5, it is preferable to dispose a plurality of the markers 11 at both ends of the stent.

In this stent 100, the adjacent two wavy annular members 2 are integrated with each other by two sharing linear portions 21 (first pattern sharing linear portion 21) or two sharing linear portions 41 (second pattern sharing linear portion 41). The two sharing linear portions 21 are opposed to each other with respect to the axis of the stent 100. Similarly the two sharing linear portions 41 are opposed to each other with respect to the axis of the stent 100.

In the stent 100, the first pattern sharing linear portion 21 and the second pattern sharing linear portion 41 are disposed alternately with respect to the axial direction thereof. Further, the first pattern sharing linear portion 21 and the second pattern sharing linear portion 41 are disposed uncontinuously with each other in the axial direction of the stent 100. More specifically, the second pattern sharing linear portion 41 is shifted from the first pattern sharing linear portion 21 in the circumferential direction of the stent 100.

In the stent 100, the first pattern sharing linear portion 21 and the second pattern sharing linear portion 41 extend obliquely with respect to the axial direction of the stent and are different from each other in the orientation thereof.

More specifically, in the stent 100, one annular member 2 has two big wavy portions formed at positions opposed to each other with respect to the axis thereof. The adjacent two wavy annular members 2 are integrated with each other by two sharing linear portions. In the stent 100, the termination point of the first pattern sharing linear portion 21 of one wavy annular member 2 is connected to the other-end side bent portion thereof by a linear portion 24. Similarly the termination point of the second pattern sharing linear portion 41 of one wavy annular member 2 is connected to the other-end side bent portion thereof by the linear portion 24. The linear portion 24 of the stent 100 is a little longer than other linear portions.

In the stent 100, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent and two second pattern sharing linear portions 41 adjacent to each other in the axial direction of the stent (in other words, four sharing linear portions) are substantially equiangularly disposed with respect to the axis of the stent 100. Thereby the stent 100 is capable of entirely displaying a substantially uniform expansive force.

As shown in FIG. 23, in the stent 100, the first pattern sharing linear portions 21 are spirally disposed in the axial direction thereof. Similarly the second pattern sharing linear portions 41 are spirally disposed in the axial direction thereof.

As shown in FIG. 23, the stent 100 has 11 wavy annular members arranged in the axial direction thereof. The first pattern sharing linear portions 21 are spirally disposed in the axial direction thereof. Similarly the second pattern sharing linear portions 41 are spirally disposed in the axial direction thereof.

More specifically, the alternate adjacent wavy annular members are connected with each other by two first pattern sharing linear portions 21. The first pattern sharing linear portions 21 are spirally disposed in the axial direction of the stent 100 to form two spirals. Each of the two spirals is composed of five first pattern sharing linear portions 21. Similarly the alternate adjacent wavy annular members (not connected by first pattern sharing linear portion 21) are connected with each other by two second pattern sharing linear portions 41. The second pattern sharing linear portions 41 are spirally disposed in the axial direction of the stent 100 to form two spirals. Each of the two spirals is constructed of five second pattern sharing linear portions 41.

As described above, the first pattern sharing linear portions 21 and the second pattern sharing linear portions 41 extend obliquely with respect to the axial direction of the stent 100 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 100 is capable of entirely displaying a substantially uniform expansive force.

As shown in FIG. 23, one wavy annular member 2 of the stent 100 has a short linear portion 26 connecting the termination point 23 of the first pattern sharing linear portion 21 thereof and the apex 2*a* of the one-end side bent portion thereof to each other. The wavy annular member adjacent to the wavy annular member 2 having the short linear portion 26 has a short linear portion 25 connecting the start point 22 of the first pattern sharing linear portion 21 thereof and the apex 2*b* of the other-end side bent portion thereof to each other and a short linear portion 47 connecting a termination point 42 of the second pattern sharing linear portion 41 thereof and the apex of the one-end side bent portion thereof to each other.

As shown in FIGS. 22 and 24, the stent 100 has a bent linear portion, one end of which is disposed at a start point or a termination point of a sharing linear portion of the wavy annular member 2 and other end of which is disposed at a start point or a termination point of a sharing linear portion of a wavy annular member adjacent to the above-described wavy annular member at a proximal side of the stent in the axial direction thereof. The bent linear portion has a one-end side bent portion or/and an other-end side bent portion.

The construction of the stent 100 of this embodiment has a small resistance to an axial expansion and contraction thereof and favorable follow-up performance for deformation of blood vessels.

More specifically, as shown in FIGS. 22 and 24, the stent 100 of this embodiment has a bent linear portion (first pattern bent linear portion) 71, one end of which is disposed at a start point 22 of a sharing linear portion (first pattern sharing linear portion 21) of the wavy annular member 2 and other end of which is disposed at a start point 41*a* of a sharing linear portion (second pattern sharing linear portion 41) of the wavy annular member adjacent to the above-described wavy annular member having the above-described sharing linear portion at the proximal side of the stent 100 in the axial direction thereof. The bent linear portion 71 has a plurality of bent portions (more specifically, four bent portion. Exactly, two one-side bent portions and two other-side bent portions).

As shown in FIGS. 22 and 24, the stent 100 of this embodiment has a bent linear portion (second pattern bent linear portion) 72, one end of which is disposed at a termination point 23 of a sharing linear portion (first pattern sharing linear portion 21) of the wavy annular member 2 and other end of which is disposed at a termination point 41*b* of a sharing linear portion (second pattern sharing linear portion 41) of the wavy annular member adjacent to the wavy annular member having the above-described sharing linear portion at the proximal side of the stent 100 in the axial direction thereof. The bent linear portion 72 has a plurality of bent portions (more specifically, one one-side bent portion and one other-side bent portion).

Therefore the wavy annular member 2 adjacent to the wavy annular member 2 disposed at the one end of the stent in the axial direction thereof has the bent linear portions 71 and 72.

As shown in FIGS. 22 and 24, at the one-end portion of the stent 100, the bent linear portions 71 and 72 are alternately disposed in the circumferential direction thereof.

The wavy annular member 2 adjacent to the wavy annular member 2 having the bent linear portions 71 and 72 at the proximal side of the stent in the axial direction thereof has a bent linear portion (third pattern bent linear portion) 73, one end of which is disposed at the start point 41*a* of the sharing linear-portion (second pattern sharing linear portion 41) of the wavy annular member 2 and other end of which is disposed at the start point 22 of the sharing linear portion (first pattern sharing linear portion 21) of the wavy annular member adjacent to the above-described wavy annular member 2 having the above-described sharing linear portion at the proximal side of the stent 100 in the axial direction thereof. The wavy annular member 2 further has a bent linear portion (fourth pattern bent linear portion) 74, one end of which is disposed at the termination point 41*b* of a sharing linear portion (second pattern sharing linear portion 41) of the wavy annular member 2 and other end of which is disposed at the termination point 23 of the sharing linear portion (first pattern sharing linear portion 21) of the wavy annular member adjacent to the above-described wavy annular member having the above-described sharing linear portion at the proximal side of the stent 100 in the axial direction thereof. Thus the wavy annular member 2 adjacent to the wavy annular member 2 having the bent linear portions 71 and 72 at the proximal side of the stent in the axial direction thereof has the bent linear portions 73 and 74.

The bent linear portion 73 (third pattern bent linear portion) has a plurality of bent portions (more specifically, one one-side bent portion and one other-side bent portion). The bent linear portion 74 (fourth pattern bent linear portion) has a plurality of bent portions (more specifically, four one-side bent portions. Exactly, two one-side bent portions and two other-side bent portions).

As shown in FIGS. 22 and 24, in the stent 100, the bent linear portions 73 and 74 are alternately disposed in the circumferential direction thereof.

The wavy annular member 2 adjacent to the wavy annular member 2 having the bent linear portions 73 and 74 at the proximal side of the stent in the axial direction thereof has the bent linear portions 71 and 72. In the wavy annular members disposed at the proximal side of the stent in the axial direction thereof with respect to the above-described wavy annular member, the above-described pattern is repeated.

Figure 25:
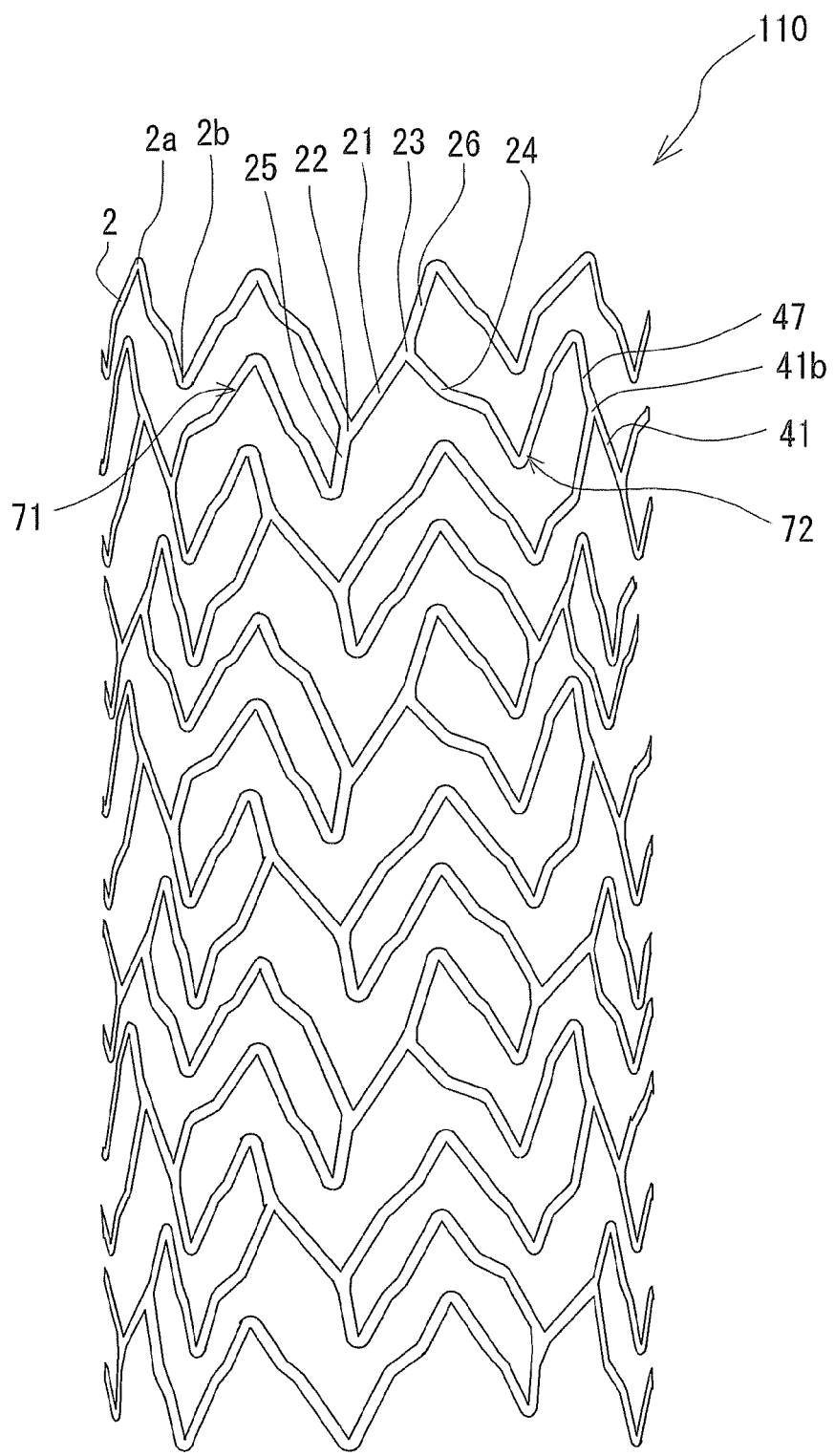
FIG. 25 is a front view showing a stent of another embodiment of the present invention.
Figure 26:
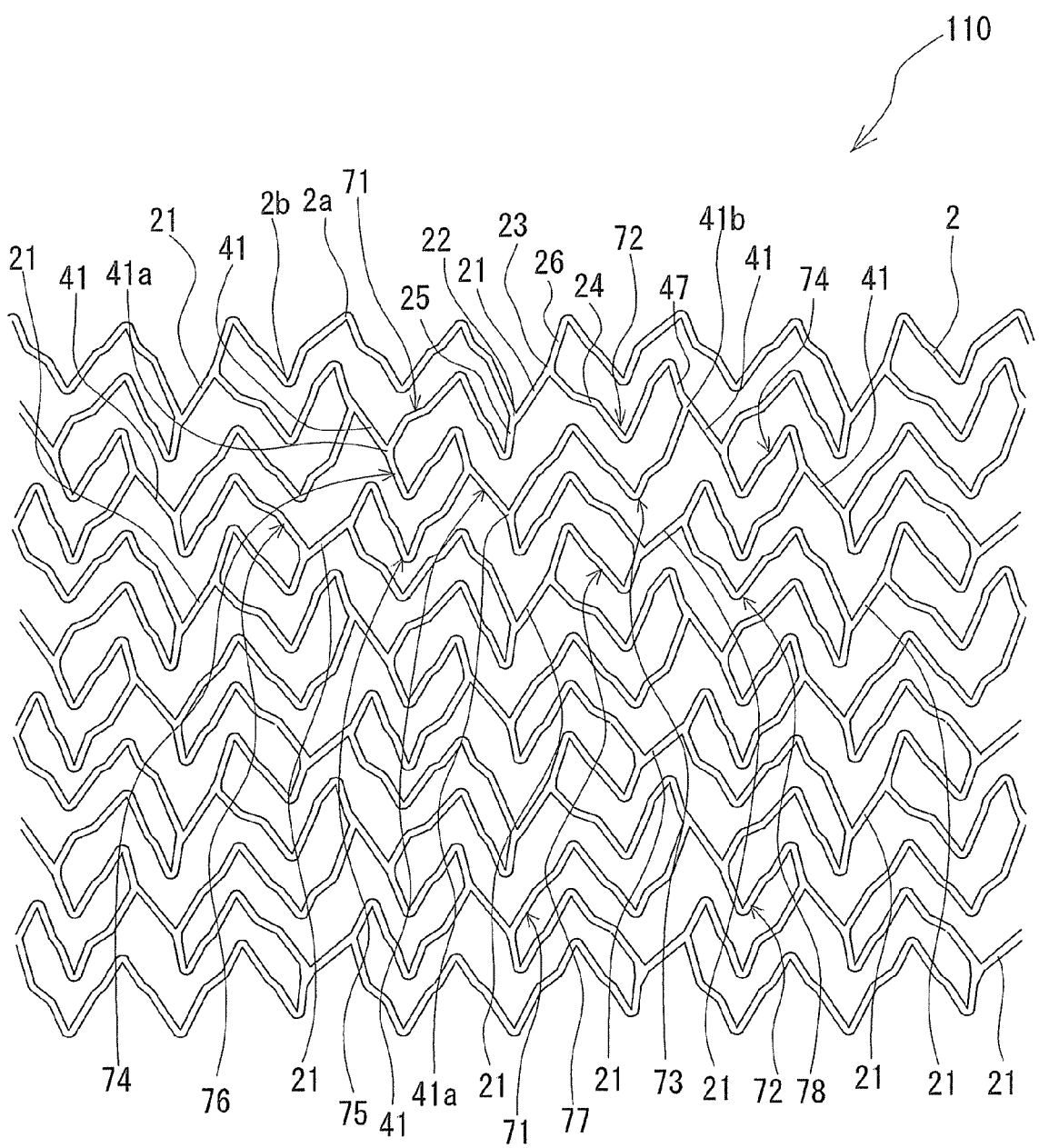
FIG. 26 is a development view showing the stent shown in FIG. 25.
Figure 27:
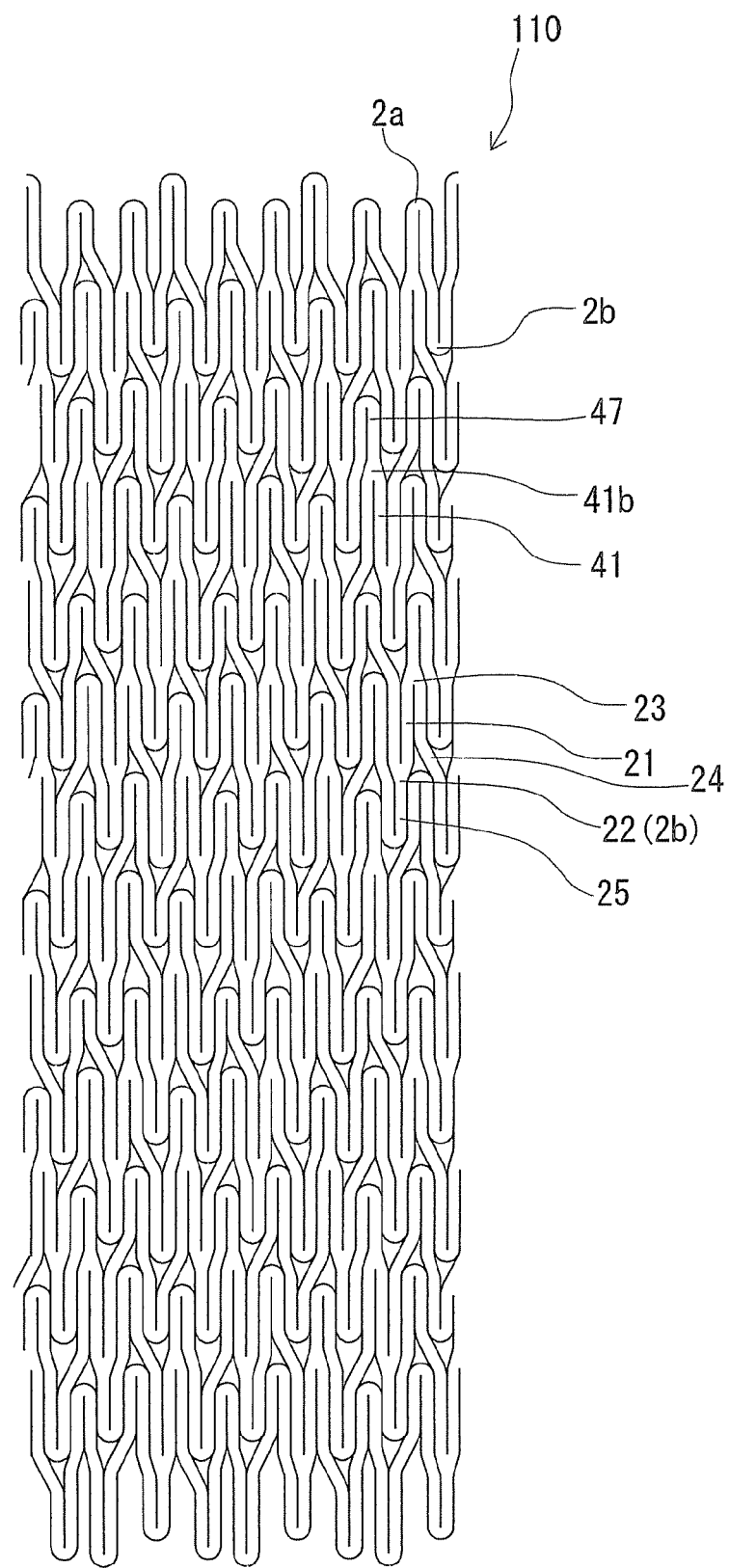
FIG. 27 is a development view showing the stent shown in FIG. 25, when the stent is contracted.

The stent of the present invention may be formed as a stent 110 having a construction as shown in FIGS. 25 through 27. FIG. 25 is a front view showing another embodiment of the stent of the present invention. FIG. 26 is a development view of the stent shown in FIG. 25. FIG. 27 is a development view of the stent, shown in FIG. 25, when the stent is contracted.

The stent 110 has the same basic construction as that of the stent 100. In the stent 110, the sharing linear portions 21 (first pattern sharing linear portion) are arranged almost straight with respect to the axial direction of the stent. Similarly the sharing linear portions 41 (second pattern sharing linear portion) are arranged almost straight with respect to the axial direction of the stent.

In the stent 110, the number of the one-end side bent portions of one wavy annular member 2 thereof and that of the other-end side bent portions thereof are equal to that of the wavy annular member 2 of the stent 100. More specifically, the number of the one-end side bent portions of the wavy annular member 2 and that of the other-end side bent portions are nine respectively. Thirteen wavy annular members 2 are arranged in the axial direction of the stent 110. The adjacent two wavy annular members 2 are integrated with each other by three sharing linear portions 21 (first pattern sharing linear portion 21) or by three sharing linear portions 41 (second pattern sharing linear portion 41). The three sharing linear portions 21 are substantially equiangularly disposed in the axial direction of the stent 110. Similarly the three sharing linear portions 41 are substantially equiangularly disposed in the axial direction of the stent 110.

In this stent 110, the sharing linear portions (first pattern sharing linear portion) 21 and the sharing linear portions (second pattern sharing linear portion 41) extend obliquely with respect to the axial direction of the stent 110 and are different from each other in the orientation thereof.

More specifically, in the stent 110, the termination point of the first pattern sharing linear portion 21 of one wavy annular member 2 is connected to the other-end side bent portion (not sharing linear portion) thereof by the linear portion 24. Similarly the termination point of the second pattern sharing linear portion 41 of one wavy annular member 2 is connected to the other-end side bent portion (not sharing linear portion) thereof by the linear portion 24. The linear portion 24 connected with the sharing linear portion is not formed as clearly as the long linear portion 24 of the stent 100. The linear portion 24 of the stent 110 is a little longer than other linear portions but may be formed as a long linear portion.

In the stent 110, one one-end side bent portion and one other-end side bent portion are disposed between the first pattern sharing linear portion 21 and the second pattern sharing linear portion 41 adjacent to the first pattern sharing linear portion 21 in the axial direction thereof.

Two first pattern sharing linear portions 21 adjacent to each other in the axial direction of the stent and the two second pattern sharing linear portions 41 adjacent to each other in the axial direction of the stent (in other words, four pattern sharing linear portions) are substantially equiangularly disposed with respect to the axis of the stent 110. Therefore the stent 110 is capable of entirely displaying a substantially uniform expansive force.

As shown in FIG. 26, the stent 110 has 13 wavy annular members arranged in the axial direction thereof. The first pattern sharing linear portions 21 are spirally disposed in the axial direction thereof. Similarly the second pattern sharing linear portions 41 are spirally disposed in the axial direction thereof.

More specifically, the one-end side wavy annular member (first wavy annular member) and the wavy annular member (second wavy annular member) adjacent thereto are connected to each other with three first pattern sharing linear portions 21. The other-end side wavy annular member and the wavy annular member adjacent thereto at the axial one-end side are connected to each other with three second pattern sharing linear portions 41. In the adjacent wavy annular members except the one-end side wavy annular member and the other-end side wavy annular member, from the axial one-end side of the stent toward the axial other-end side thereof, the two same states in which the adjacent wavy annular members are connected to each other with three second pattern sharing linear portions 41 are continuous and these states are followed by the two same states in which the adjacent wavy annular members are connected to each other with three first pattern sharing linear portions 21 are continuous. This pattern is repeated from the one-end side of the stent toward the other-end side thereof.

More specifically, the second wavy annular member and the wavy annular member (third wavy annular member) adjacent thereto, and the third wavy annular member and the wavy annular member (fourth wavy annular member) adjacent thereto are connected to each other respectively with three second pattern sharing linear portions 41. The fourth wavy annular member and the wavy annular member (fifth wavy annular member) adjacent thereto, and the fifth wavy annular member and the wavy annular member (sixth wavy annular member) adjacent thereto are connected to each other respectively with three first pattern sharing linear portions 21. The above-described patterns are repeated toward the axial proximal end of the stent.

In the stent 110, six rows each consisting of a plurality (three) of the first pattern sharing linear portions 21 disposed almost axially straight are formed. The six rows each consisting of the first pattern sharing linear portions 21 are almost equiangularly disposed with respect to the axis of the stent. Similarly in the stent 110, six rows each consisting of a plurality (three) of the second pattern sharing linear portions 41 disposed almost axially straight are formed. The six rows each consisting of the second pattern sharing linear portions 41 are almost equiangularly disposed with respect to the axis of the stent.

As described above, the first pattern sharing linear portions 21 and the second pattern sharing linear portions 41 extend obliquely with respect to the axial direction of the stent 110 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent is capable of entirely displaying a substantially uniform expansive force.

Describing the arrangement manner of the sharing linear portions in the axial direction of the stent three first pattern sharing linear portions 21 are formed at uniform intervals in the circumferential direction of the stent. Three second pattern sharing linear portions 41 are formed adjacently to the first pattern sharing linear portions 21 at uniform intervals in the circumferential direction of the stent. Three second pattern sharing linear portions 41 are formed adjacently to the above-described second pattern sharing linear portions 41 at uniform intervals in the circumferential direction of the stent.

Three first pattern sharing linear portions 21 are formed adjacently to the above-described second pattern sharing linear portions 41 at uniform intervals in the circumferential direction of the stent. In this manner, the first pattern sharing linear portion 21 and the second pattern sharing linear portion 41 are arranged in the order of 21, 41, 41, 21, 21, 41, 41 . . . .

The construction of the stent 110 makes a resistance to an axial expansion and contraction of the wavy annular member smaller. Thereby the stent 110 has more favorable follow-up performance for deformation of blood vessels.

As shown in FIG. 25 through 27, in the stent 110, the wavy annular member 2 adjacent to the one-end side wavy annular member 2 at the proximal side of the stent in the axial direction thereof has the bent linear portion (first pattern bent linear portion) 71, one end of which is disposed at the start point 22 of the sharing linear portion (first pattern sharing linear portion 21) of the wavy annular member 2 and other end of which is disposed at the start point 41a of the sharing linear portion (second pattern sharing linear portion 41) of the wavy annular member adjacent to the above-described wavy annular member having the above-described sharing linear portion at the proximal side of the stent 110 in the axial direction thereof and the bent linear portion (second pattern bent linear portion) 72, one end of which is disposed at the termination point 23 of the sharing linear portion (first pattern sharing linear portion 21) of the wavy annular member 2 and other end of which is disposed at the termination point 41b of the sharing linear portion (second pattern sharing linear portion 41) of the wavy annular member adjacent to the wavy annular member having the above-described sharing linear portion at the proximal side of the stent 110 in the axial direction thereof. Therefore the wavy annular member 2 adjacent to the one-end side wavy annular member 2 at the proximal side of the stent 110 in the axial direction thereof has the bent linear portions 71 and 72.

In the stent 110 of this embodiment, the bent linear portion 71 has a plurality of bent portions (more specifically, one one-side bent portion and one other-side bent portion). The bent linear portion 72 has also a plurality of bent portions (more specifically, one one-side bent portion and one other-side bent portion). The bent linear portions 71 and 72 are alternately disposed in the circumferential direction of the stent.

The wavy annular member 2 adjacent to the wavy annular member 2 having the bent linear portions 71 and 72 at the proximal side of the stent in the axial direction thereof has a bent linear portion (third pattern bent linear portion) 73, one end of which is disposed at the termination point 41b of the sharing linear portion (second pattern sharing linear portion 41) of the wavy annular member 2 and other end of which is disposed at the start point 41a of the sharing linear portion (second pattern sharing linear portion 41) of the wavy annular member adjacent to the above-described wavy annular member having the above-described sharing linear portion at the proximal side of the stent in the axial direction thereof 110. The wavy annular member 2 further has the bent linear portion (fourth pattern bent linear portion) 74, one end of which is disposed at the start point 41a of the sharing linear portion (second pattern sharing linear portion 41) of the wavy annular member 2 and other end of which is disposed at the termination point 41b of the sharing linear portion (second pattern sharing linear portion 41) of the wavy annular member adjacent to the above-described wavy annular member having the above-described sharing linear portion at the proximal side of the stent 110 in the axial direction thereof. Thus the wavy annular member 2 adjacent to the wavy annular member 2 having the bent linear portions 71 and 72 at the proximal side of the stent in the axial direction thereof has the bent linear portions 73 and 74.

Each of the bent linear portions 73 and 74 has a plurality of bent portions (more specifically, one one-side bent portion and one other-side bent portion).

As shown in FIG. 25 through 27, in the stent 110, the bent linear portions 73 and 74 are alternately disposed in the circumferential direction thereof.

The wavy annular member 2 adjacent to the wavy annular member 2 having the bent linear portions 73 and 74 at the proximal side of the stent in the axial direction thereof has a bent linear portion (fifth pattern bent linear portion) 75, one end of which is disposed at the termination point 41b of the sharing linear portion (second pattern sharing linear portion 41) of the wavy annular member 2 and other end of which is disposed at the termination point 23 of the sharing linear portion (first pattern sharing linear portion 21) of the wavy annular member adjacent to the above-described wavy annular member having the above-described sharing linear portion at the proximal side of the stent in the axial direction thereof 110. The wavy annular member 2 further has a bent linear portion (sixth pattern bent linear portion) 76, one end of which is disposed at the start point 41a of the sharing linear portion (second pattern sharing linear portion 41) of the wavy annular member 2 and other end of which is disposed at the start point 22 of the sharing linear portion (first pattern sharing linear portion 21) of the wavy annular member adjacent to the above-described wavy annular member having the above-described sharing linear portion at the proximal side of the stent 110 in the axial direction thereof. Thus the wavy annular member 2 adjacent to the wavy annular member 2 having the bent linear portions 73 and 74 at the proximal side of the stent in the axial direction thereof has the bent linear portions 75 and 76.

Each of the bent linear portions 75 and 76 has a plurality of bent portions (more specifically, one one-side bent portion and one other-side bent portion).

As shown in FIG. 25 through 27, in the stent 110, the bent linear portions 75 and 76 are alternately disposed in the circumferential direction thereof.

The wavy annular member 2 adjacent to the wavy annular member 2 having the bent linear portions 75 and 76 at the proximal side of the stent in the axial direction thereof has a bent linear portion (seventh pattern bent linear portion) 77, one end of which is disposed at the start point 22 of the sharing linear portion (first pattern sharing linear portion 21) of the wavy annular member 2 and other end of which is disposed at the termination point 23 of the sharing linear portion (first pattern sharing linear portion 21) of the wavy annular member adjacent to the above-described wavy annular member having the above-described sharing linear portion at the proximal side of the stent 110 in the axial direction thereof, and a bent linear portion (eighth pattern bent linear portion) 78, one end of which is disposed at the termination point 23 of the sharing linear portion (first pattern sharing linear portion 21) of the wavy annular member 2 and other end of which is disposed at the start point 22 of the sharing linear portion (first pattern sharing linear portion 21) of the wavy annular member adjacent to the wavy annular member having the above-described sharing linear portion at the proximal side of the stent 110 in the axial direction thereof. Thus the wavy annular member 2 adjacent to the wavy annular member 2 having the bent linear portions 75 and 76 at the proximal side of the stent in the axial direction thereof has the bent linear portions 77 and 78.

Each of the bent linear portions 77 and 78 has a plurality of bent portions (more specifically, one one-side bent portion and one other-side bent portion). As shown in FIG. 25 through 27, in the stent 110, the bent linear portions 77 and 78 are alternately disposed in the circumferential direction thereof.

The wavy annular member 2 adjacent to the wavy annular member 2 having the bent linear portions 77 and 78 at the proximal side of the stent in the axial direction thereof has the bent linear portions 71 and 72 having the above-described pattern.

Figure 28:
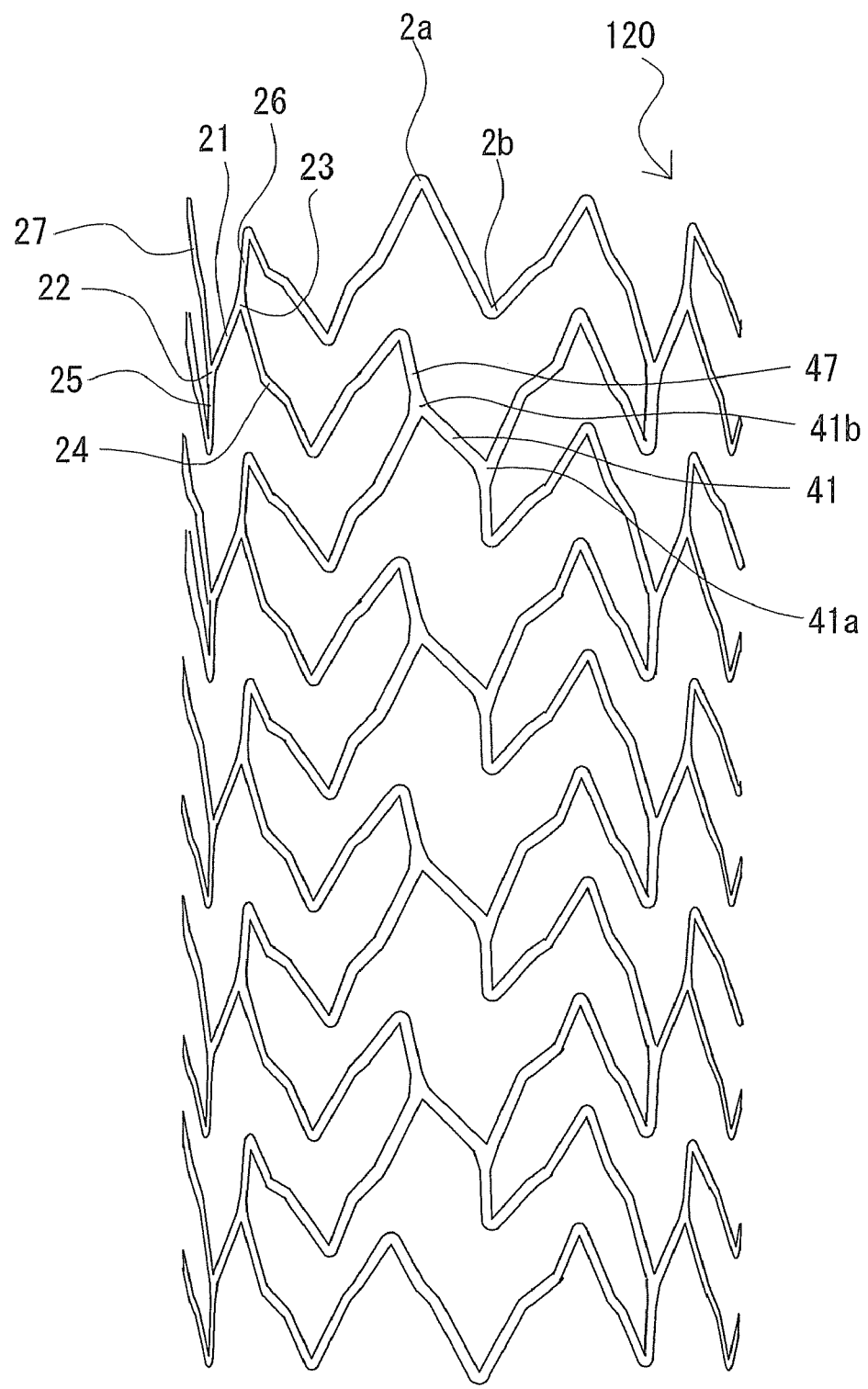
FIG. 28 is a front view, showing a stent of another embodiment of the present invention.
Figure 29:
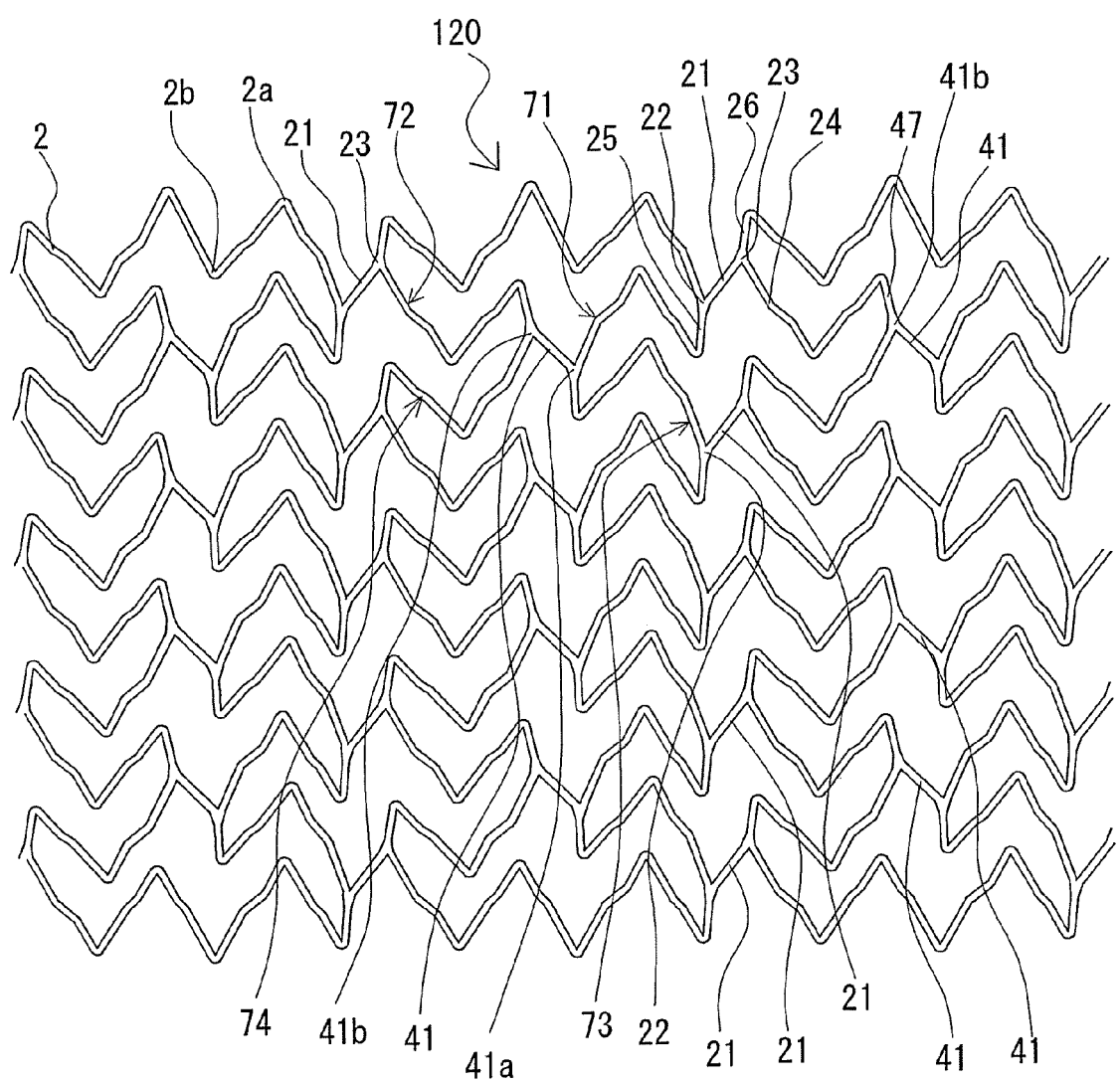
FIG. 29 is a development view showing the stent shown in FIG. 28.
Figure 30:
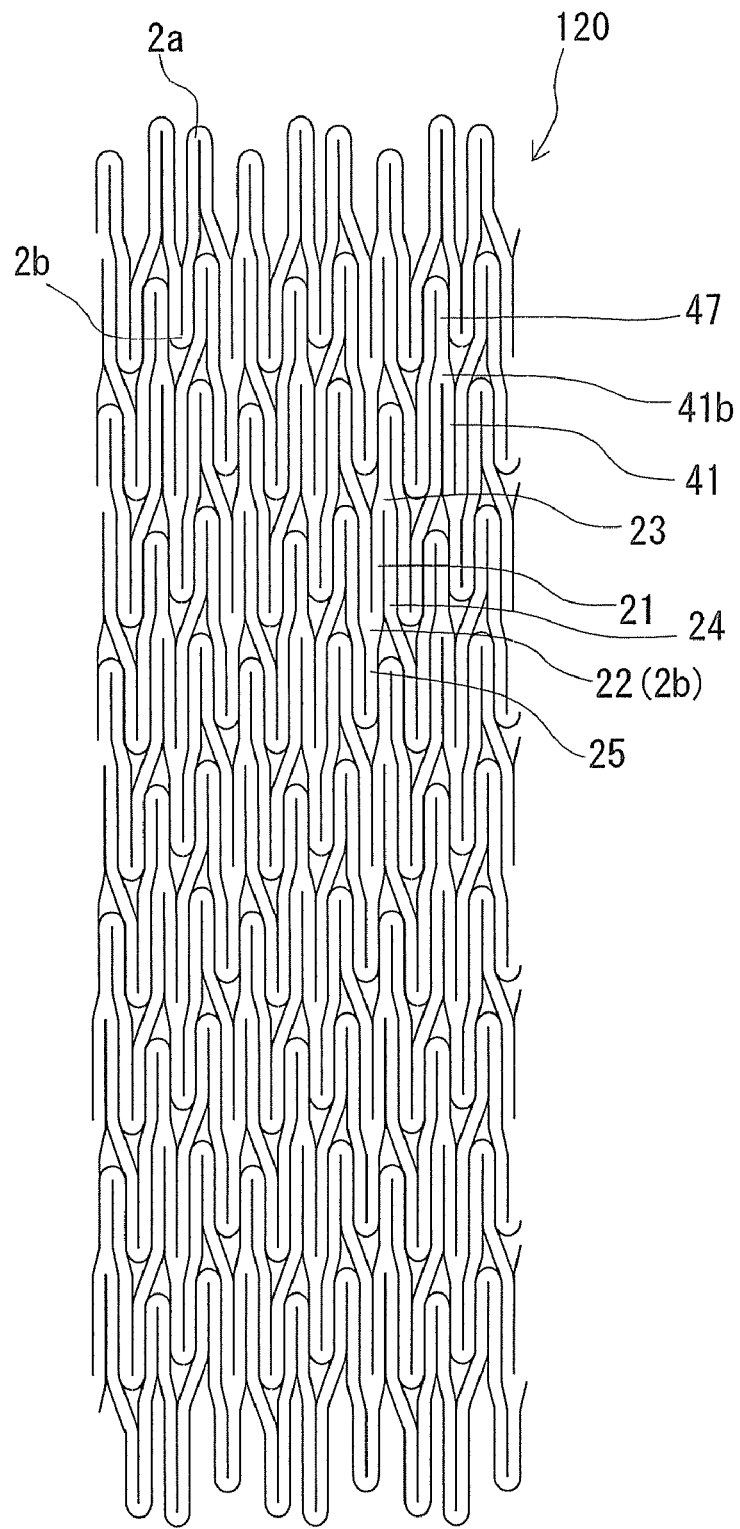
FIG. 30 is a development view showing the stent shown in FIG. 28, when the stent is contracted.

The stent of the present invention may be formed as a stent 120 having a construction as shown in FIGS. 28 through 30. FIG. 28 is a front view showing still another embodiment of the stent of the present invention. FIG. 29 is a development view showing the stent shown in FIG. 28. FIG. 30 is a development view showing the stent shown in FIG. 28, whose diameter is decreased.

In the stent 120, the number of the one-end side bent portions of one wavy annular member 2 and that of the other-end side bent portions thereof are equal to than that of the wavy annular member 2 of the stent. More specifically, the number of the one-end side bent portions of the wavy annular member 2 and that of the other-end side bent portions thereof are nine respectively. Ten wavy annular members 2 are disposed in the axial direction of the stent 120. The adjacent two wavy annular members 2 are integrated with each other by three sharing linear portions 21 (first pattern sharing linear portion 21) or three sharing linear portions 41 (second pattern sharing linear portion 41). The three sharing linear portions 21 are substantially equiangularly disposed in the axial direction of the stent 120. Similarly the three sharing linear portions 41 are substantially equiangularly disposed in the axial direction thereof.

In the stent 120, the sharing linear portions (first pattern sharing linear portion) 21 and the sharing linear portions (second pattern sharing linear portion) 41 are disposed alternately in the axial direction of the stent 120. Further, the first pattern sharing linear portions (first pattern sharing linear portion) 21 and the sharing linear portions (second pattern sharing linear portion) 41 are disposed uncontinuously with each other in the axial direction of the stent 120. More specifically, the sharing linear portion (second pattern sharing linear portion) 41 is shifted from the sharing linear portion (first pattern sharing linear portion) 21 in the circumferential direction of the stent 120. The sharing linear portions (first pattern sharing linear portion) 21 are formed substantially straight in the axial direction of the stent 120. Similarly the sharing linear portions (second pattern sharing linear portion) 41 are formed substantially straight in the axial direction of the stent 120.

In the stent 120, the first pattern sharing linear portion 21 and the second pattern sharing linear portion 41 extend obliquely with respect to the axial direction of the stent and are different from each other in the orientation thereof.

More specifically, in the stent 120, the termination point of the first pattern sharing linear portion 21 of one wavy annular member 2 is connected to the other-end side bent portion thereof by the linear portion 24. Similarly the termination point of the second pattern sharing linear portion 41 of one wavy annular member 2 is connected to the other-end side bent portion thereof by the linear portion 24. The linear portion 24 of the stent 120 is a little longer than other linear portions but may be formed as a long linear portion.

In the stent 120, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent and two second pattern sharing linear portions 41 adjacent to each other in the axial direction of the stent (in other words, four sharing linear portions) are substantially equiangularly disposed with respect to the axis of the stent 120. Therefore the stent 120 is capable of entirely displaying a substantially uniform expansive force.

As described above, the first pattern sharing linear portions 21 and the second pattern sharing linear portions 41 extend obliquely with respect to the axial direction of the stent and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent is capable of entirely displaying a substantially uniform expansive force. Describing the arrangement manner of the sharing linear portions in the axial direction of the stent, three first pattern sharing linear portions 21 are formed at uniform intervals in the circumferential direction of the stent. Three second pattern sharing linear portions 41 are formed adjacently to the first pattern sharing linear portions 21 at uniform intervals in the circumferential direction of the stent. Three first pattern sharing linear portions 21 are formed adjacently to the above-described second pattern sharing linear portions 41 at uniform intervals in the circumferential direction of the stent.

Three second pattern sharing linear portions 41 are formed adjacently to the above-described first pattern sharing linear portions 21 at uniform intervals in the circumferential direction of the stent. In this manner, the first pattern sharing linear portion 21 and the second pattern sharing linear portion 41 are arranged in the order of 21, 41, 21, 41, 21, 41, 21 . . .

The construction of the stent 120 makes a resistance to an axial expansion and contraction small. Thereby the stent 120 has more favorable follow-up performance for deformation of blood vessels.

As shown in FIG. 29, the wavy annular member 2 of the stent 120 has a short linear portion 26 connecting the termination point 23 of the first pattern sharing linear portion 21 thereof and the apex 2a of the one-end side bent portion thereof to each other. As shown in FIG. 29, the wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 41b of the second pattern sharing linear portion 41 thereof and the apex of the one end side bent portion thereof to each other.

Similarly to the stent 100, as shown in FIGS. 28 and 29, the stent 120 of this embodiment has the bent linear portion (first pattern bent linear portion) 71, one end of which is disposed at the start point 22 of the sharing linear portion (first pattern sharing linear portion 21) of the wavy annular member 2 and other end of which is disposed at the start point 41*a* of the sharing linear portion (second pattern sharing linear portion 41) of the wavy annular member adjacent to the above-described wavy annular member having the above-described sharing linear portion at the proximal side of the stent 120 in the axial direction thereof; and the bent linear portion (second pattern bent linear portion) 72, one end of which is disposed at the termination point 23 of the sharing linear portion (first pattern sharing linear portion 21) of the wavy annular member 2 and other end of which is disposed at the termination point 41*b* of the sharing linear portion (second pattern sharing linear portion 41) of the wavy annular member adjacent to the wavy annular member having the above-described sharing linear portion at the proximal side of the stent 120 in the axial direction thereof. Therefore the wavy annular member 2 adjacent to the one-end side wavy annular member 2 at the proximal side of the stent in the axial direction thereof has the bent linear portions 71 and 72. The bent linear portions 71 and 72 are alternately disposed in the circumferential direction thereof.

The wavy annular member 2 adjacent to the wavy annular member 2 having the bent linear portions 71 and 72 at the proximal side of the stent in the axial direction thereof has the bent linear portion (third pattern bent linear portion) 73, one end of which is disposed at the start point 41*a* of the sharing linear portion (second pattern sharing linear portion 41) of the wavy annular member 2 and other end of which is disposed at the start point 22 of the sharing linear portion (first pattern sharing linear portion 21) of the wavy annular member adjacent to the above-described wavy annular member having the above-described sharing linear portion at the proximal side of the stent 120 in the axial direction thereof. The wavy annular member 2 further has the bent linear portion (fourth pattern bent linear portion) 74, one end of which is disposed at the termination point 41*b* of the sharing linear portion (second pattern sharing linear portion 41) of the wavy annular member 2 and other end of which is disposed at the termination point 23 of the sharing linear portion (first pattern sharing linear portion 21) of the wavy annular member adjacent to the above-described wavy annular member having the above-described sharing linear portion at the proximal side of the stent 120 in the axial direction thereof. Thus the wavy annular member 2 adjacent to the wavy annular member 2 having the bent linear portions 71 and 72 at the proximal side of the stent in the axial direction thereof has the bent linear portions 73 and 74. The bent linear portions 73 and 74 are alternately disposed in the circumferential direction thereof.

Each of the bent linear portions 71, 72, 73, and 74 has a plurality of bent portions (more specifically, one one-side bent portion and one other-side bent portion).

The wavy annular member 2 adjacent to the wavy annular member 2 having the bent linear portions 73 and 74 at the proximal side of the stent in the axial direction thereof has the bent linear portions 71 and 72.

Figure 31:
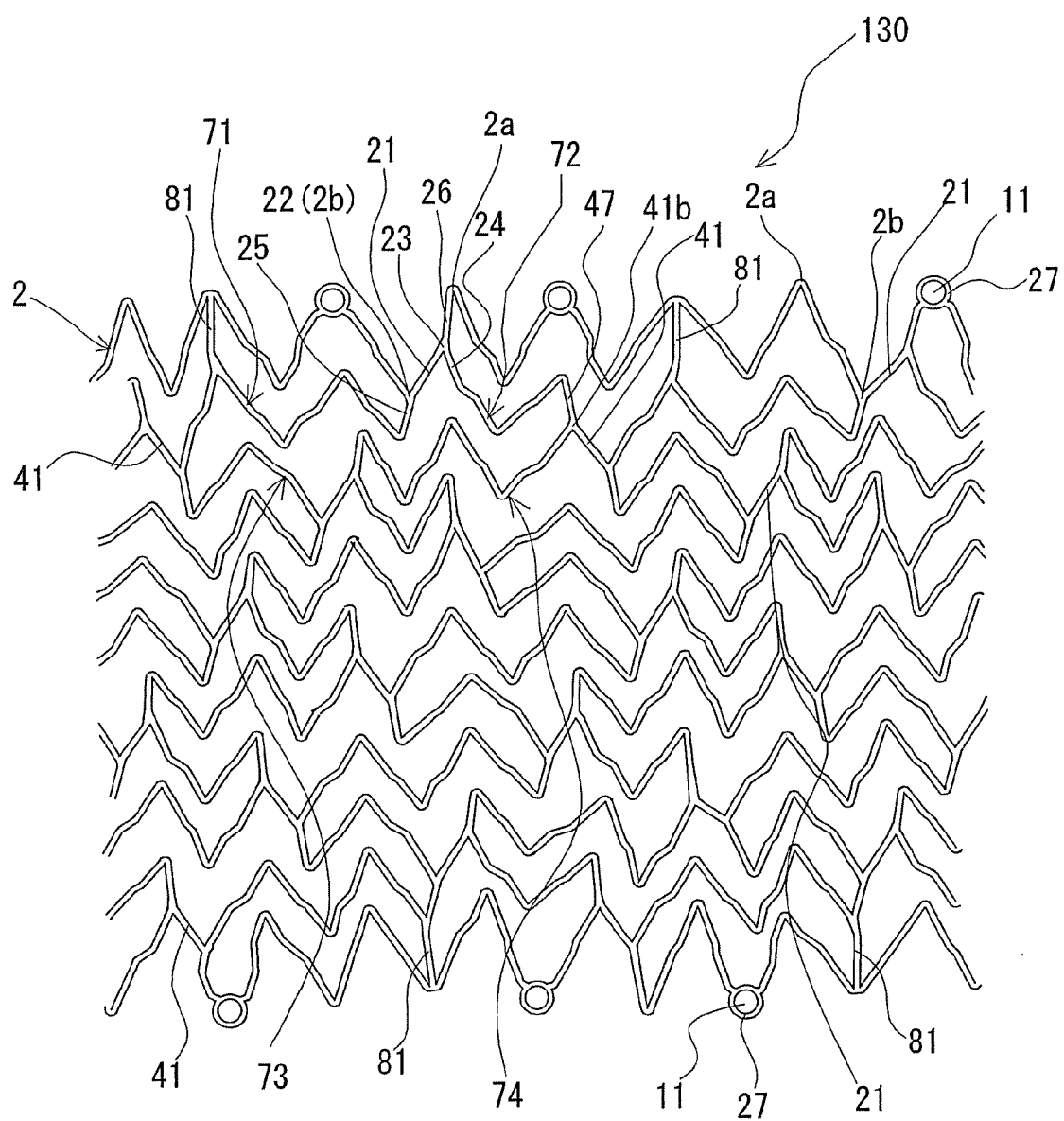
FIG. 31 is a development view showing a stent of another embodiment of the present invention.
Figure 32:
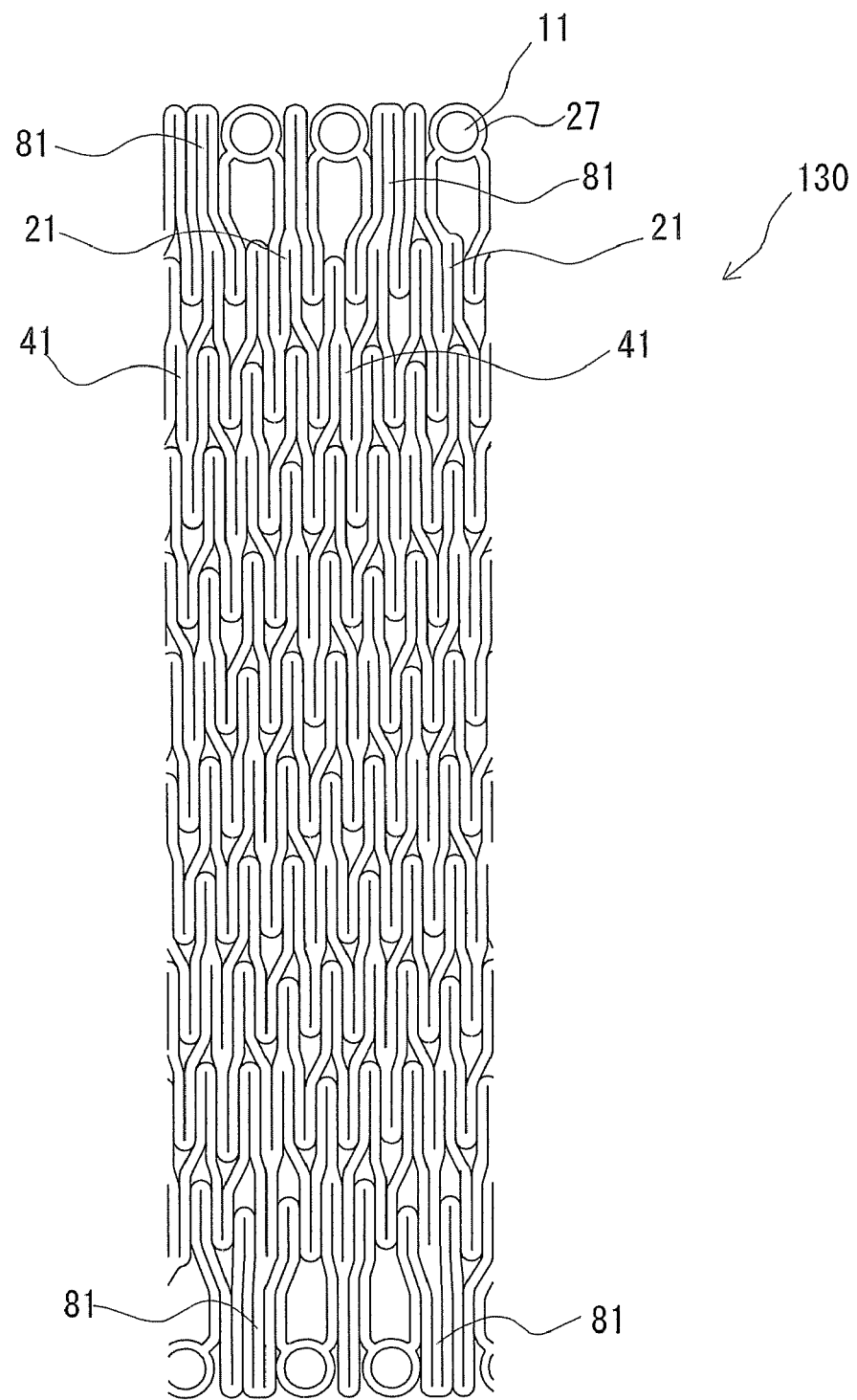
FIG. 32 is a development view showing the stent, shown in FIG. 31, when the stent is contracted.

The stent of the present invention may be formed as a stent 130 having a construction as shown in FIGS. 31 and 32. FIG. 31 is a development view showing still another embodiment of the stent of the present invention. FIG. 32 is a development view showing the stent shown in FIG. 31, when the stent contracted.

The stent 130 is different from the stent 100 in that the stent 130 has markers formed at both axial ends thereof and connection portions formed on wavy annular members disposed at both axial ends thereof. The basic construction of the stent 130 is the same as that of the above-described stent 100. Thus the construction of the stent 130 different from the stent 100 is mainly described below.

In the stent 130, the number of the one-end side bent portions of one wavy annular member 2 of the stent 130 and that of the other-end side bent portions of one wavy annular member 2 thereof are eight respectively. Eleven wavy annular members 2 are disposed in the axial direction of the stent 130. The adjacent two wavy annular members 2 are integrated with each other by two sharing linear portions 21 (first pattern sharing linear portion 21) or two sharing linear portions 41 (second pattern sharing linear portion 41). The two sharing linear portions 21 are opposed to each other with respect to the axis of the stent 130. Similarly the two sharing linear portions 41 are opposed to each other with respect to the axis of the stent 130.

In the stent 130, the first pattern sharing linear portion 21 and the second pattern sharing linear portion 41 are disposed alternately with respect to the axial direction thereof. Further, the first pattern sharing linear portion 21 and the second pattern sharing linear portion 41 are disposed uncontinuously with each other in the axial direction of the stent 130. More specifically, the second pattern sharing linear portion 41 is shifted from the first pattern sharing linear portion 21 in the circumferential direction of the stent 130.

As shown in FIGS. 31 and 32, the stent 130 has a contrast marker 11. It is favorable to dispose the contrast marker 11 at an end of the stent 130. It is more favorable to dispose the contrast marker 11 at both ends of the stent. More specifically, as shown in FIGS. 31 and 32, it is preferable to dispose a plurality of the markers 11 at both ends of the stent. The stent 130 of this embodiment has an opening 27 formed at an apex disposed at both ends thereof. The marker 11 closing the opening 27 is fixed to the ends of the stent.

It is preferable to mount the marker 11 on a small opening formed on the stent by pressing a disk-shaped member disposed on a small opening. The disk-shaped member is made of an X-ray contrast material having a portion a little smaller than the small opening and a portion a little larger than the small opening. Thereafter the disk-shaped member is pressed in a direction from both surfaces thereof to caulk it to the small opening like a rivet.

It is possible to use an X-ray contrast marker, an ultrasonic wave contrast marker, and the like. The marker is made of contrast substances such as an X-ray contrast substance, an ultrasonic wave contrast substance, and the like. As materials of the marker, it is preferable to use gold, platinum, tungsten, tantalum, iridium, palladium alloys of these metals, a gold-palladium alloy, a platinum-iridium alloy, NiTiPd, and NiTiAu.

As shown in FIGS. 31 and 32, an outer edge of the opening 27 is coincident with outer edges of other apexes disposed at the end (upper and lower ends) of the stent in the axial direction thereof. That is, in the stent 130, the outer edge of the opening 27 to which the marker is fixed is not projected outward from the outer edges of the other apexes disposed at the end of the stent. By making the outer edges of the stent coincident with one another in the axial direction of the stent, the stent can be securely pressed out even though the stent is curved.

The stent has two leg portions extended toward the axial center of the stent from each marker-located position with the leg portions spaced from each other at a certain interval. As shown in FIG. 32, in a contracted (mounted) state of the stent the two leg portions are spaced from each other and almost parallel with a linear portion of the stent close thereto.

More specifically, the two leg portions are extended toward the axial center of the stent from two positions of the marker-disposed opening 27 formed at the bent portion of the stent. These two positions are located at an inner side of the stent and spaced at a predetermined interval. Therefore the neighborhood of the marker-formed portion (opening 27) is stable. The two leg portions extended from the opening 27 are spaced from each other in the vicinity of the start position thereof.

The two leg portions extended from the opening 27 are spaced from each other. By spacing the two leg portions from each other at the predetermined interval, the configuration of the region in the vicinity of the marker-formed portion (opening 27) is stable. Therefore even though a strong force is applied to the region in the vicinity of the marker-formed portion (opening 27), the stent is prevented from deforming and can be reliably pressed out.

In the stent 130, the two leg portions are extended toward the center of the stent in the axial direction thereof from two positions of the opening 27 formed at the bent portion of the stent. These two positions are spaced at a predetermined interval. The stent 130 has three openings 27 at both ends thereof. Ends of the two leg portions extended from each of two of the three openings 27 are spaced from each other at a certain interval. Ends of the leg portion extended from the remaining one opening 27 are dose to each other.

As shown in FIGS. 31 and 32, in the stent 130, the wavy annular member 2 disposed at both ends (upper and lower ends) of the stent is provided with a coupling portion 81 for coupling the wavy annular member 2 and the adjacent wavy annular member 2 to each other. In the stent 130, two coupling portions 81 are provided between the wavy annular member 2 disposed at both ends (upper and lower ends) of the stent and the adjacent wavy annular member. In the stent 130, coupling portion 81 is provided only between two wavy annular members 2 disposed at both ends (upper and lower ends) of the stent and the adjacent wavy annular member 2. The two coupling portions 81 are formed at positions opposed to each other with respect to the axis of the stent.

As shown in FIGS. 31 and 32, at one end portion (upper end portion) of the stent 130, the two sharing linear portions 21 and the above-described two coupling portions 81 are disposed substantially equiangularly with respect to the axis of the stent. Similarly at the other end portion (lower end portion) of the stent 130, the two sharing linear portions 41 and the above-described two coupling portions 81 are disposed substantially equiangularly with respect to the axis of the stent.

Because the stent 130 has the sharing linear portions and the coupling portions at both end portions thereof, the form or the configuration of both end portions of the stent is stable after the stent expands. The above-described stent has two coupling portions at both end portions thereof. But the stent may have one or three coupling portions at both end portions thereof.

Because the stent 130 of this embodiment has a construction different from that of the stent 100, it has a comparatively low resistance to axial expansion and contraction thereof. Thereby the stent 130 has favorable follow-up performance for deformation of blood vessels.

Figure 33:
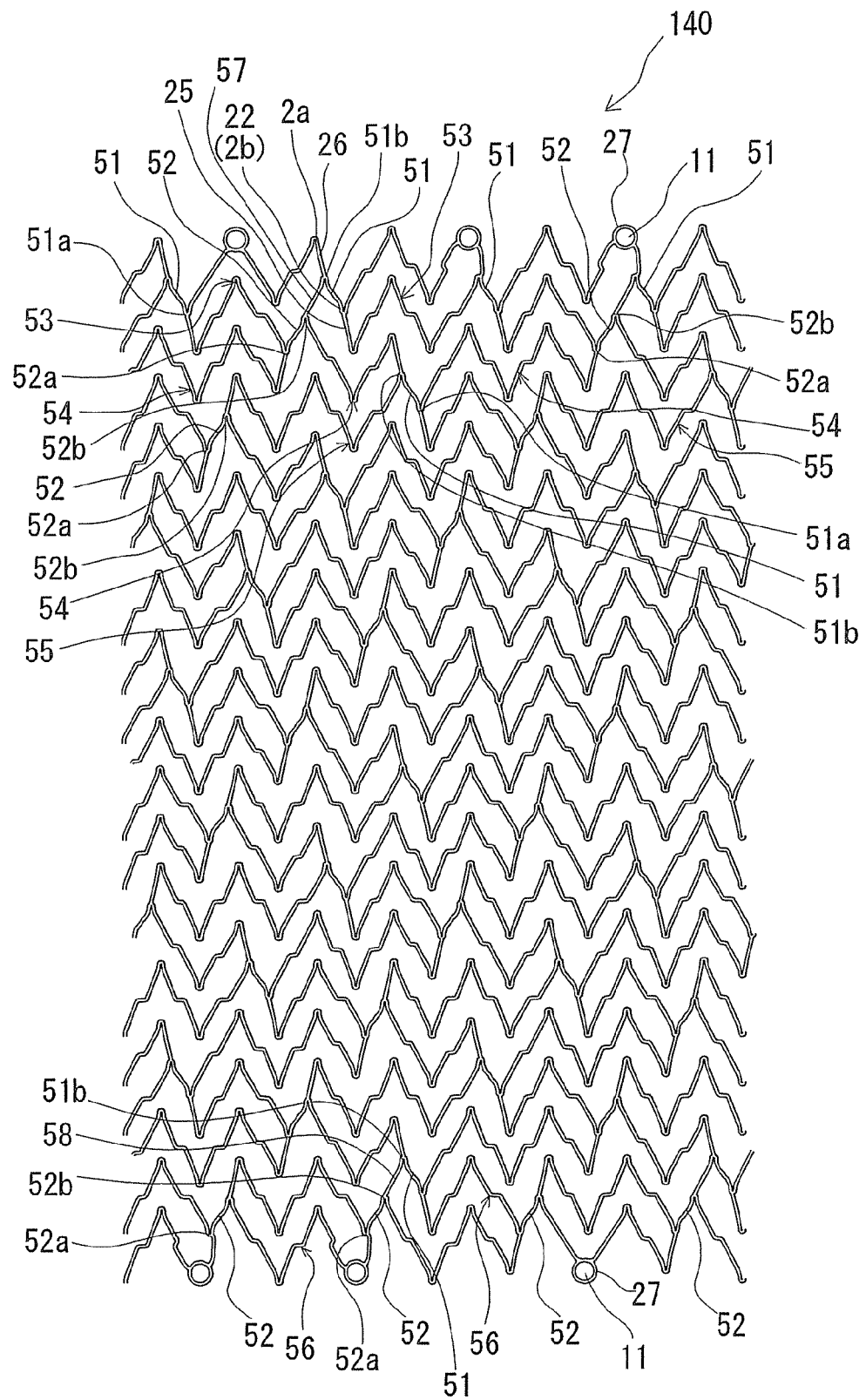
FIG. 33 is a development view showing a stent of another embodiment of the present invention.
Figure 34:
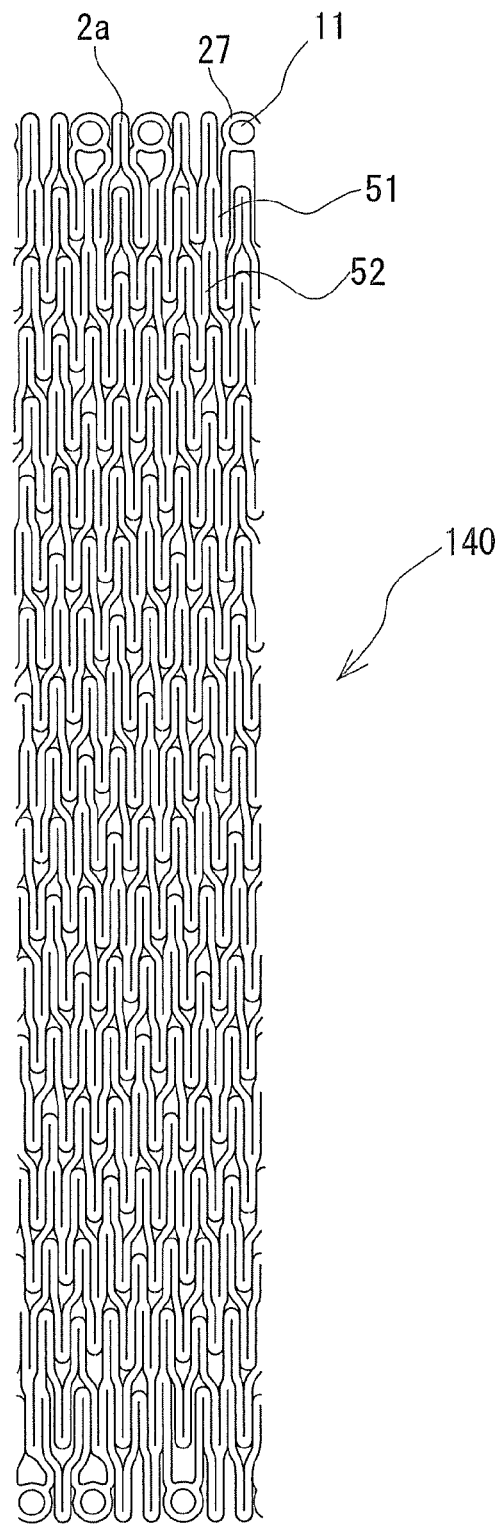
FIG. 34 is a development view showing the stent, shown in FIG. 33, when the stent is contracted.

The stent of the present invention may be formed as a stent 140 having a pattern as shown in FIGS. 33 and 34. FIG. 33 is a development view showing still another embodiment of the stent of the present invention FIG. 34 is a development view showing the stent shown in FIG. 33, when the stent contracted.

The stent 140 has the same construction as that of the stent 100 except the number of the one-end side bent portions of one wavy annular member, the number of the other-end side bent portions thereof the number of the sharing linear portions integrating the adjacent wavy annular members with each other, the arrangement form of the sharing linear portions, the orientation thereof, and the marker disposed at both ends of the stent.

The number of the one-end side bent portions of one wavy annular member 2 of the stent 140 and that of the other-end side bent portions thereof are smaller than that of one wavy annular member 2 of the stent 100. More specifically, the number of the one-end side bent portions of one wavy annular member 2 of the stent 140 and that of the other-end side bent portions of one wavy annular member 2 thereof are eight respectively. In the axial direction of the stent 140, twenty-one wavy annular members 2 are disposed. In the stent 140, the adjacent two wavy annular members 2 are integrated with each other by two sharing linear portions 51 (first pattern sharing linear portion) or two sharing linear portions 52 (second pattern sharing linear portion). In the stent 140, the adjacent two wavy annular members 2 are integrated with each other by at least two sharing linear portions. The two sharing linear portions 51 are opposed to each other with respect to the axis of the stent 140. Similarly the two sharing linear portions 52 are opposed to each other with respect to the axis of the stent 140.

As shown in FIGS. 33 and 34, in the stent 140, the wavy annular member 2 disposed at both ends (upper and lower ends) of the stent and the adjacent wavy annular member 2 are integrated with each other with four sharing linear portions. At one end portion (upper end portion) of the stent 140, the above-described four sharing linear portions 51 are disposed substantially equiangularly with respect to the axis of the stent. Similarly, at the other end portion (lower end portion) of the stent 140, the above-described four sharing linear portions 52 are disposed substantially equiangularly with respect to the axis of the stent.

Because in the stent 140, a larger number of sharing linear portions are formed at both end portions of the stent than at other portions, the form or the configuration of both end portions of the stent is stable after the stent expands.

In the stent 140, the first pattern sharing linear portion 51 and the second pattern sharing linear portion 52 are disposed alternately with respect to the axial direction thereof. Further, the first pattern sharing linear portion 51 and the second pattern sharing linear portion 52 are disposed uncontinuously with each other in the axial direction of the stent 140. More specifically, the second pattern sharing linear portion 52 is shifted from the first pattern sharing linear portion 51 in the circumferential direction of the stent 140.

In the stent 140, the first pattern sharing linear portion 51 and the second pattern sharing linear portion 52 extend obliquely with respect to the axial direction of the stent and are different from each other in the orientation thereof.

In the stent 140, except both end portions thereof, one one-end side bent portion and one other-end side bent portion are disposed between the first pattern sharing linear portion 51 and the second pattern sharing linear portion 52 adjacent to the first pattern sharing linear portion 51 in the axial direction thereof. Two first pattern sharing linear portions 51 adjacent to each other in the axial direction of the stent and two second pattern sharing linear portions 52 adjacent to each other in the axial direction thereof are substantially equiangularly disposed with respect to the axis thereof. Thereby the stent 140 is capable of entirely displaying a substantially uniform expansive force.

As shown in FIG. 33, in the stent 140, the first pattern sharing linear portions 51 are spirally disposed in the axial direction thereof. Similarly the second pattern sharing linear portions 52 are spirally disposed in the axial direction thereof.

As shown in FIG. 33, the stent 140 has twenty-one wavy annular members arranged in the axial direction thereof. The first pattern sharing linear portions 51 are spirally disposed in the axial direction thereof. Similarly the second pattern sharing linear portions 52 are spirally disposed in the axial direction thereof.

More specifically, the alternate wavy annular members are connected with each other by two first pattern sharing linear portions 51. The first pattern sharing linear portions 51 are spirally disposed in the axial direction of the stent 140 to form two spirals. Each of the two spirals is composed of first pattern sharing linear portions 51.

Similarly, the alternate wavy annular members (not connected by first pattern sharing linear portion 51) are connected with each other by two second pattern sharing linear portions 52. The second pattern sharing linear portions 52 are spirally disposed in the axial direction of the stent 140 to form two spirals.

As described above, the first pattern sharing linear portions 51 and the second pattern sharing linear portions 51 extend obliquely with respect to the axial direction of the stent 140 and are different from each other in the orientation thereof. It is preferable that the orientation of the first pattern sharing linear portion 51 and that of the second pattern sharing linear portion 52 are substantially symmetrical to each other with respect to the axis of the stent. Thereby the stent 140 is capable of entirely displaying a substantially uniform expansive force.

As shown in FIG. 33, one wavy annular member 2 of the stent 140 has a short linear portion 26 connecting the termination point 51*b* of the first pattern sharing linear portion 51 thereof and the apex 2*a* of the one-end side bent portion thereof to each other. The wavy annular member adjacent to the wavy annular member 2 having the short linear portion 26 has a short linear portion 25 connecting the start point 22 of the first pattern sharing linear portion 51 thereof and the apex 2*b* of the other-end side bent portion thereof to each other and a short linear portion connecting a termination point 52*b* of the second pattern sharing linear portion 52 thereof and the apex of the one-end side bent portion thereof to each other.

As shown in FIGS. 33 and 34, the stent 140 has a contrast marker 11. It is favorable to dispose the contrast marker 11 at an end of the stent 140. It is more favorable to dispose the contrast marker 11 at both ends of the stent. More specifically, as shown in FIGS. 33 and 34, it is preferable to dispose a plurality of the markers 11 at both ends of the stent. The stent 140 of this embodiment has an opening 27 formed at an apex disposed at both ends of the stent. The marker 11 closing the opening 27 is fixed to the ends of the stent. The contrast marker is the same as that of the above-described stent 130.

As shown in FIGS. 33 and 34, an outer edge of the opening 27 is coincident with outer edges of other apexes disposed at the end (upper and lower ends) of the stent in the axial direction thereof. That is, in the stent 140, the outer edge of the opening 27 to which the marker is fixed is not projected outward from the outer edges of the other apexes disposed at the end of the stent. By making the outer edges of the stent coincident with one another in the axial direction of the stent, the stent can be securely pressed out even though the stent is curved.

In the stent 140, the two leg portions are extended toward the axial center of the stent from two positions of the opening 27 formed at the bent portion. These two positions are spaced at a predetermined interval.

Therefore the neighborhood of the marker-formed portion (opening 27) is stable. Three openings 27 are formed at both ends of the stent 140. Ends of the two leg portions extended from one of the three openings 27 are spaced from each other at a certain interval. Ends of the leg portion extended from the remaining two opening 27 are dose to each other respectively.

As shown in FIG. 33, in the stent 140, the wavy annular member 2 adjacent to the wavy annular member 2 disposed at the one end of the stent at the proximal side in the axial direction thereof has a bent linear portion (first pattern bent linear portion) 53, one end of which is disposed at a start point 51*a* of a sharing linear portion (first pattern sharing linear portion) 51 of the wavy annular member 2 and the other end of which is disposed at a termination point 51*b* of other sharing linear portion 51 of the same wavy annular member 2. A plurality of the bent linear portions 53 is arranged in the circumferential direction of the stent. The stent 140 has four sharing linear portions 51 at one end of the stent 140 in its axial direction. In correspondence to this construction, the wavy annular member 2 adjacent to the one-end side wavy annular member 2 at the proximal side of the stent in the axial direction thereof has four bent linear portions 53. The four bent linear portions 53 are disposed substantially equiangularly with respect to said axis of said stent.

As shown in FIG. 33, the stent 140 has a linear portion 57 (more specifically, short connection portion) directly connecting the termination point 51*b* of the sharing linear portion 51 of the one-end side wavy annular member 2 to a termination point 52*b* of a sharing linear portion 52 (dose to the above-described sharing linear portion) of the wavy annular member 2 adjacent to the one-end side wavy annular member 2. Therefore the one-end side wavy annular member (first wavy annular member) and the third wavy annular member (third wavy annular member) from the one-end of the stent are connected to each other with the linear portion 57 and are also connected to the second wavy annular member (second wavy annular member) from the one-end of the stent with the sharing linear portions. Thereby the stent 140 has a high expanded state retention force at the one-end side thereof.

Similarly as shown in FIG. 33, the stent 140 has a linear portion 58 (more specifically, short connection portion) directly connecting the termination point 52*b* of the sharing linear portion 52 of the other-end side wavy annular member 2 to the termination point 51*b* of the sharing linear portion 51 (close to the above-described sharing linear portion) of the wavy annular member 2 adjacent to the other-end side wavy annular member 2. Therefore the other-end side wavy annular member (other-end side first wavy annular member) and the third wavy annular member (other-end side third wavy annular member) from the other-end of the stent are connected to each other with the linear portion 58 and are also connected to the second wavy annular member (other-end side second wavy annular member) from the other-end of the stent with the sharing linear portions. Thereby the stent 140 has a high expanded state retention force at the other-end side thereof.

The wavy annular member 2 adjacent to the wavy annular member 2 having the bent linear portion 53 at the proximal side of the stent in the axial direction thereof has a bent linear portion (second pattern bent linear portion) 54, one end of which is disposed at the termination point 52*b* of the sharing linear portion (second pattern sharing linear portion) 51 of the wavy annular member 2 and the other end of which is disposed at a start point 52*a* of other sharing linear portion 52 of the same wavy annular member 2. A plurality of the bent linear portions 54 is arranged in the circumferential direction of the stent. In the stent 140, two sharing linear portions 52 are formed between the adjacent wavy annular members. In correspondence to this construction, the wavy annular member 2 adjacent to the wavy annular member 2 having the bent linear portion 53 at the proximal side of the stent in the axial direction thereof has two bent linear portions 54. The two bent linear portions 54 are disposed substantially opposed to each other with respect to said axis of said stent.

The wavy annular member 2 adjacent to the wavy annular member 2 having the bent linear portion 54 at the proximal side of the stent in the axial direction thereof has a bent linear portion (third pattern bent linear portion) 55, one end of which is disposed at the start point 51a of the sharing linear portion (first pattern sharing linear portion) 51 of the wavy annular member 2 and the other end of which is disposed at the termination point 51b of the other sharing linear portion 51 of the same wavy annular member 2. A plurality of the bent linear portions 55 is arranged in the circumferential direction of the stent. The stent 140 has two sharing linear portions 51 between the adjacent wavy annular members. In correspondence to this construction, the wavy annular member 2 adjacent to the wavy annular member 2 having the bent linear portion 54 at the proximal side of the stent in the axial direction thereof has two bent linear portions 55. The two bent linear portions 55 are disposed substantially opposed to each other with respect to said axis of said stent.

The wavy annular member 2 adjacent to the wavy annular member 2 having the bent linear portion 55 at the proximal side of the stent in the axial direction thereof has two bent linear portions 54. This pattern is repeatedly formed to the wavy annular member adjacent to the proximal-end wavy annular member.

The proximal-end wavy annular member 2 has four sharing linear portions (second pattern sharing linear portion 52) between proximal-end wavy annular member 2 and the wavy annular member disposed adjacently thereto. The proximal-end wavy annular member 2 has a bent linear portion (fourth pattern bent linear portion) 56, one end of which is disposed at the termination point 52b of the sharing linear portion (second pattern sharing linear portion) 52 of the wavy annular member 2 adjacent to the proximal-end wavy annular member at the distal side of the stent in the axial direction thereof and the other end of which is disposed at the start point 52a of other sharing linear portion 52 of the same wavy annular member 2. A plurality of the bent linear portions 56 is arranged in the circumferential direction of the stent. As described above, the stent 140 has four sharing linear portions 52 at the proximal end thereof and in correspondence to this construction, has four bent linear portions 56. The four bent linear portions 56 are disposed substantially equiangularly with respect to said axis of said stent.

The outer diameter, thickness, and length of the stent are different respectively in dependence on a portion where the stent is implanted. When the stent is expanded (when it is not contracted in its diameter and when it is restored to its original state), the outer diameter thereof is favorably in the range of 2.0 to 30 mm and more favorably in the range of 2.5 to 20 mm; the thickness (thickness of linear member) thereof is favorably in the range of 180 to 230 μm and more favorably in the range of 190 to 210 μm; and the length thereof is favorably in the range of 10-150 mm and more favorably in the range of 15 to 100 mm. In the case of the stent to be implanted in the blood vessel, the outer diameter thereof is favorably in the range of 20 to 14 mm and more favorably in the range of 25 to 12 mm; the thickness thereof is favorably in the range of 180 to 230 mm and more favorably in the range of 190 to 210 μm; and the length thereof is favorably in the range of 5-100 mm and more favorably in the range of 10 to 80 mm.

The stents of all of the above-described embodiments are formed approximately cylindrically and integrally from a metal pipe to which super elastic property can be imparted, by removing a part of the metal pipe other than a part thereof corresponding to a linear portion constituting the stent.

As a metal to which the super-elastic property can be imparted, a so-called super-elastic alloy can be preferably used.

The following super-elastic metals can be favorably used: A Ti—Ni alloy of 49-54 atomic percent of Ni, a Cu—Zn alloy of 38.5-41.5 wt % of Zr, a Cu—Zn—X alloy of 1-10 wt % of X (X=Be, Si, Sn, Al, Ga), and a Ni—Al alloy of 36-38 atomic percent of Al. The Ti—Ni alloy is most favorable. The mechanical characteristic of the Ti—Ni alloy can be appropriately changed by replacing a part of the Ti—Ni alloy with 0.01-10.0% of X to obtain a Ti—Ni—X alloy (X=Co, Fe, Mn, Cr, V, Al, Nb, W, B, Au, and Pd) or by replacing a part of the Ti—Ni alloy with 0.01-30.0 atomic percent of X to obtain a Ti—NiX alloy (X=Cu, Pb, Zr). Further the mechanical characteristic of the super-elastic alloy can be appropriately changed by selectively adopting a cold working ratio or/and the condition of final heat treatment.

In the case where the Ti—Ni—X alloy is used, it is also possible to change the mechanical characteristic of the super-elastic alloy appropriately by selectively adopting the cold working ratio or/and the condition of the final heat treatment The buckling strength (yield stress when load is applied to stent) of the super-elastic alloy to be used is favorably in the range of 5-200 kg/mm$^2$ (22 degree C.) and more favorably in the range of 8-150 kg/mm$^2$. The restoring stress (yield stress when load is eliminated from stent) of the super-elastic alloy is favorably in the range of 3-180 kg/mm$^2$ (22 degree C.) and more favorably in the range of 5-1.30 kg/mm$^2$. The super-elasticity means that when a metal is deformed (bent, stretched, compressed) to a region in which it deforms plastically at a service temperature, it returns to its original configuration substantially without heating it after an applied load is eliminated.

The stent is formed by removing (for example, cutting, dissolving) a part of the pipe made of the super-elastic metal not constituting the stent. Thereby the stent is obtained as an integral product. The pipe made of the super-elastic metal to be used to form the stent of the present invention can be produced by dissolving the super-elastic alloy such as the Ti—Ni alloy in an inactive gas atmosphere or a vacuum atmosphere to form an ingot thereof, polishing the ingot mechanically, forming a pipe having a large diameter by hot press and extrusion repeating a drawing step from a dies and a heat treatment step to adjust the diameter and thickness of the pipe to a predetermined thickness and reduced diameter, and finally polishing the surface of the pipe chemically or physically. The pipe made of the super-elastic metal can be processed into the base material for the stent by a cutting work such as laser processing (for example, YAG laser), electrical discharge machining, chemical etching cutting processing or in combination thereof.

By approximately heat-treating the stent formed in the above-described manner, the stent shows the super-elastic property before and after the stent is inserted into an organism. The line width of the linear portion of the stent is set to 100 to 170 μm and favorably 100 to 140 μm. The thickness of the linear portion (in other words, thickness of metal pipe) is set to 180 to 230 μm and favorably 190 to 210 μm.

In all of the above-described embodiments, a compression load for compressing the axial length of the stent by 20% is set to 10 to 20 gf. In other words, the stent of the present invention can be axially compressed by 20% by applying the compression load of 10 to 20 gf thereto. It is favorable that the stent of the present invention can be axially compressed by 20% by applying the compression load of 12 to 18 gf thereto. It is more favorable that the stent of the present invention can be axially compressed by 20% by applying the compression load of 12 to 14 gf thereto.

The stent of the present invention may be coated with a material suitable for the organism on its inner surface, outer surface or inner and outer surfaces. As the material suitable for the organism, synthetic resin and metal suitable for the organism can be used. The following inactive metals are used to coat the surface of the stent gold by an electroplating method, stainless steel by an evaporation method, silicon carbide, diamond-like carbon, plated titanium nitride, and plated gold by a sputtering method. As the synthetic resin, the following thermoplastic resins or thermosetting resins can be used polyolefin (for example, polyethylene, polypropylene, ethylene-propylene copolymer), polyvinyl chloride, ethylene-vinyl acetate copolymer, polyamide elastomer, polyurethane, polyester, fluoro resin, silicone resin. It is preferable to use polyolefin, polyamide elastomer, polyester, polyurethane, silicone resin. A resin decomposable in the organism (polylactic acid, polyglycolic acid, polylactic add-polyglycolic add copolymer) is also favorable. It is preferable that a film of the synthetic resin is soft such an extent as not to prevent a frame constituting the stent from being curved. The thickness of the film of the synthetic resin is favorably in the range of 3 to 300 µm and more favorably in the range of 5 to 100 µm.

As the method of thinly coating the surface of the stent with the synthetic resin, it is possible to use a method of inserting the stent into the melted synthetic resin or into the synthetic resin dissolved in a solution. It is also possible to use a chemical evaporation method of polymerizing a monomer over the surface of the pipe made of the superelastic metal. In the case where the surface of the stent is coated very thinly with the synthetic resin, the use of a dilute solution or the chemical evaporation method is preferable. To improve the quality of the material suitable for the organism to a higher extent the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, a copolymer of hydroxyethyl methacrylate and styrene (for example, HEMA-St-HEMA block copolymer) can be preferably used.

It is preferable to provide the stents of the above-described embodiments with a marker 11 as shown in FIGS. 31 through 34. It is favorable to dispose the marker 11 at an end of each stent. It is more favorable to dispose the marker 11 at both ends of the stent. More specifically, it is preferable to dispose a plurality of the markers 11 at both ends of the stent. The marker is as described above.

Example 5

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 23 was inputted to a design software of the personal computer. The X table and the rotary motor were driven in accordance with design data outputted from the personal computer.

The metal pipe was irradiated with laser beams to machine the metal pipe into a base material for the stent having a configuration whose development view is as shown in FIG. 23.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remaining inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550 degree C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 22 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 200 µm. The width of the linear portion of each wavy linear member was about 113 µm. The axial length of the wavy annular member was about 3 mm. The length of the sharing linear portion was about 1.6 mm.

The stent had a sufficient expansive force. Further a strain did not concentrate on a connection portion.

Example 6

Except that a development drawing of the stent having the structure shown in FIG. 26 was inputted to a personal computer, a material of the stent as shown in FIG. 25 was prepared in a manner similar to that of the example 1. After the material of the stent shaped in a manner similar to that of the example 1 underwent blast treatment process, chemical polishing process, and electropolishing process, the process of smoothening the surface of the material of the stent and the process of imparting metallic luster to the surface thereof was conducted.

The stent prepared in this manner had an outer diameter of about 8 mm, an entire length of about 45 mm, and a thickness of about 200 µm, a line width of 113 µm in the linear portion of each wavy annular member, a length of about 3 mm in the wavy annular member in the axial length of the stent, and a length of about 1.6 mm in the sharing linear portion.

The stent had a sufficient expansive force and little concentration of strain on the connection portion thereof.

Example 7

Except that a development drawing of the stent having the structure shown in FIG. 29 was inputted to the personal computer, a material of the stent as shown in FIG. 28 was prepared in a manner similar to that of the example 1. After the material of the stent shaped in a manner similar to that of the example 1 underwent blast treatment process, chemical polishing process, and electropolishing process, the process of smoothening the surface of the material of the stent and the process of imparting metallic luster to the surface thereof was conducted.

The stent prepared in this manner had an outer diameter of about 8 mm, an entire length of about 45 mm, and a thickness of about 200 μm, a line width of 113 μm in the linear portion of each wavy annular member, a length of about 3 mm in the wavy annular member in the axial length of the stent and a length of about 1.6 mm in the sharing linear portion.

The stent had a sufficient expansive force and little concentration of strain on the connection portion thereof.

Example 8

Except that a development drawing of the stent having the structure shown in FIG. 31 was inputted to the personal computer, a material of the stent was prepared in a manner similar to that of the example 1. After the material of the stent shaped in a manner similar to that of the example 1 underwent blast treatment process, chemical polishing process, and electropolishing process, the process of smoothening the surface of the material of the stent and the process of imparting metallic luster to the surface thereof was conducted.

The stent prepared in this manner had an outer diameter of about 8 mm, an entire length of about 45 mm, and a thickness of about 200 μm, a line width of 113 μm in the linear portion of each wavy annular member, a length of about 3 mm in the wavy annular member in the axial length of the stent and a length of about 1.4 mm in the sharing linear portion.

The stent had a sufficient expansive force and little concentration of strain on the connection portion thereof.

Example 9

Except that a development drawing of the stent having the structure shown in FIG. 33 was inputted to the personal computer, a material of the stent was prepared in a manner similar to that of the example 1. After the material of the stent shaped in a manner similar to that of the example 1 underwent blast treatment process, chemical polishing process, and electropolishing process, the process of smoothening the surface of the material of the stent and the process of imparting metallic luster to the surface thereof was conducted.

The stent prepared in this manner had an outer diameter of about 8 mm, an entire length of about 45 mm, and a thickness of about 200 μm, a line width of 113 μm in the linear portion of each wavy annular member, a length of about 3 mm in the wavy annular member in the axial length of the stent and a length of about 1.4 mm in the sharing linear portion.

The stent had a sufficient expansive force and little concentration of strain on the connection portion thereof.

Comparison Example

Figure 35:
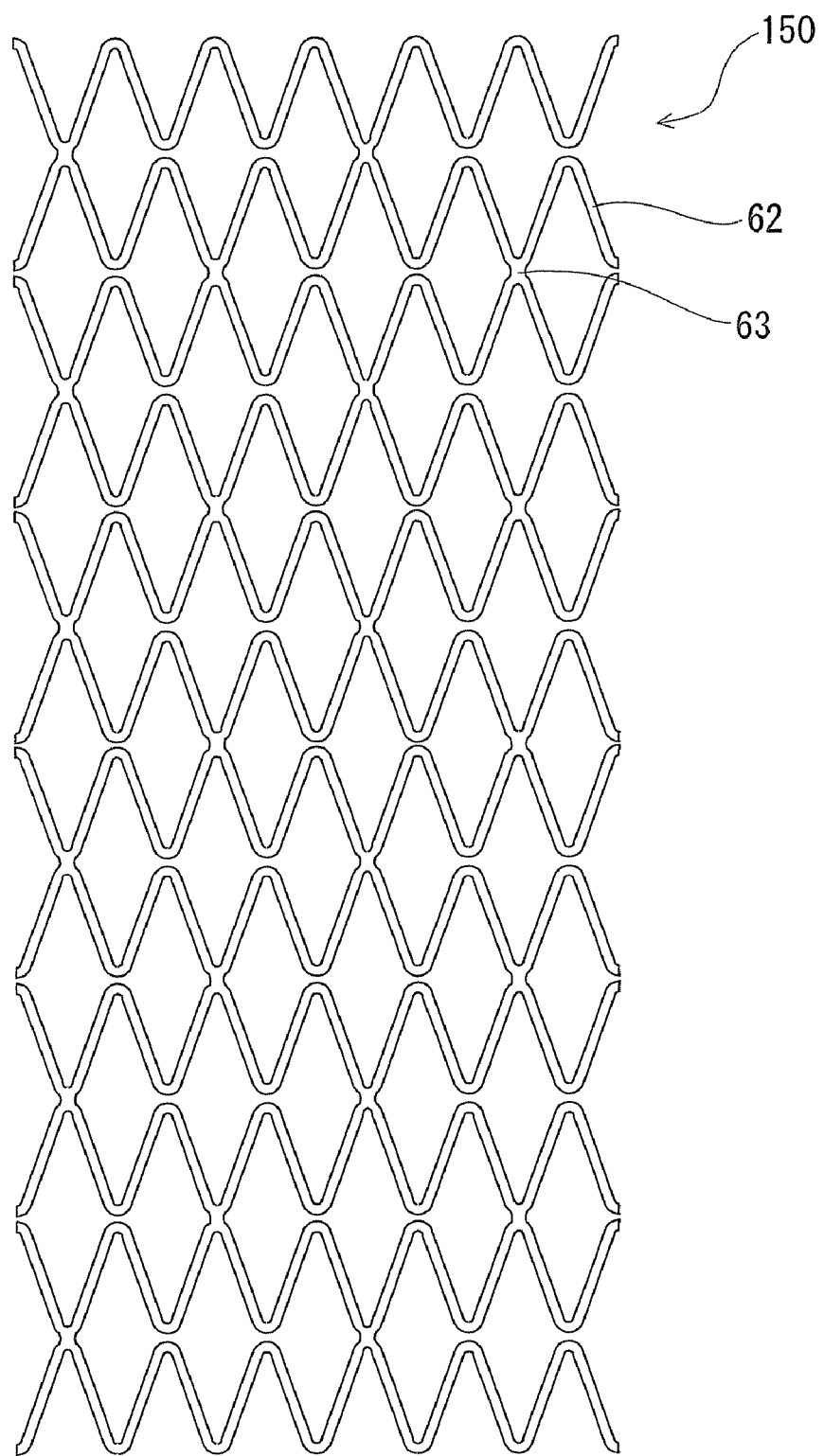
FIG. 35 is a development view showing a stent of comparative embodiment.

Except that a development drawing of the stent 150 having the structure shown in FIG. 35 was inputted to the personal computer, a material of the stent was prepared in a manner similar to that of the example 1. After the material of the stent shaped in a manner similar to that of the example 1 underwent blast treatment process, chemical polishing process, and electropolishing process, the process of smoothening the surface of the material of the stent and the process of imparting metallic luster to the surface thereof was conducted.

The stent prepared in this manner had an outer diameter of about 8 mm, an entire length of about 45 mm, and a thickness of about 200 μm, a line width of 113 μm in the linear portion of each wavy annular member 62, a length of about 2 mm in the wavy annular member 62 in the axial length of the stent and a length of about 0.2 mm in the connection portion.

The stent had a sufficient expansive force and little concentration of strain on the connection portion thereof.

The stent is implanted at various portions of lumens of an organism. Thus demanded functions of the stent are different from one another in dependence on portions of the lumens. It is preferable that the stent has a comparatively high resistance to axial expansion and contraction thereof and is strong when the stent is implanted in the carotid artery and the renal artery. This is because these blood vessels expand and contract to a low extent for a movement of the organism. Therefore it is preferable to use the stent which expands and contracts to a low extent and holds the blood vessels firmly.

The iliac artery expands and contracts to a low extent for the movement of the organism and has a comparatively large diameter. Therefore it is preferable to use the stent which holds the iliac artery. A radial force (radial force resistant to compression load) is necessary for a calcified blood vessel. As indicated in the results of the measurement conducted in the experiment which will be described later, a stent having a high radial force resistant to the compression load is capable of radially expanding the blood vessel and holding it.

The superficial femoral artery and the popliteal artery expand and contract to a high extent for a movement of the organism. Further in many cases, because a lesion in the lower limbs is long, it is necessary to implant a long stent in these blood vessels. In this case, the stent is demanded to have a comparatively low resistance to axial expansion and contraction thereof and be axially flexible. As a result of energetic researches of the present inventors, they have developed stents having approximately the same constructions but different resistances (flexibilities) to the axial expansion and contraction thereof.

Compression loads (axial compression load) for axially compressing the axial length of the stents of the examples and the comparison example by 20% were measured. More specifically, each stent having an effective length of 20 mm, an outer diameter of 8 mm, and a length of 45 mm was compressed in water having a temperature of 37 degree C. at a compression speed of 5 mm/minute, with both ends thereof held. A force at the time when the effective length of the stent became 16 mm was measured. The results are as shown in table 2.

The radial compression load of the stent of each of the examples and the comparison examples was measured. More specifically, with each stent disposed between two flat plates in water, the flat plates were pressed. A force applied thereto when the outer diameter of each stent became 4 mm was measured. The results are as shown in table 2.

TABLE 2

| Stent | Axial compression load(gf) | Radial compression load(gf) |
| --- | --- | --- |
| Example 5 | 11.5 | 70.0 |
| Example 6 | 18.3 | 50.5 |
| Example 7 | 17.3 | 53.6 |
| Example 8 | 17.2 | 63.6 |
| Example 9 | 13.0 | 72.5 |
| Comparison example | 124.1 | 75.0 |

The stent of the present invention to be implanted in the organism is a self-expandable stent formed approximately cylindrically and integrally from a metal pipe to which super-elastic property can be imparted, by removing a part of the metal pipe other than a part thereof corresponding to the linear portion constituting the stent. The stent shows the super-elastic property before and after the stent is inserted into the organism. The line width of the linear portion of the stent is set to 100 to 170 μm. The thickness of the linear portion is set to 180 to 230 μm. A compression load for compressing the axial length of the stent by 20% is 10 to 20 gf.

Therefore the stent has a sufficiently high expansive force and axially deforms at a small load. Thereby the stent easily expands and contracts in its axial direction and has favorable follow-up performance for deformation of blood vessels. For example, the stent is preferable for being embedded in very expandable and contractible blood vessels such the artery of the inferior limb including the superficial femoral artery, the popliteal artery.

What is claimed is:

1. A stent comprising: a plurality of wavy annular members arranged in an axial direction thereof, wherein each of said wavy annular members has a plurality of one-end side bent portions each having an apex at a one-end side of said stent in said axial direction thereof and a plurality of other-end side bent portions each having an apex at an other-end side of said stent in said axial direction thereof; and in said wavy annular members disposed adjacently to each other in said axial direction of said stent, said wavy annular member disposed at said one-end side of said stent in said axial direction thereof has a sharing linear portion having a start point at or in the vicinity of said apex of one of said other-end side bent of said wavy annular member disposed at said one-end side of said stent, and a termination point between said apex of said other-end side bent portion of said wavy annular member disposed at said one-end side of said stent and said apex of one of said one-end side bent portions of said wavy annular member disposed at said one-end side of said stent, wherein said wavy annular member disposed at said one-end side of said stent comprises both the start point and the termination point of said sharing linear portion; and said stent having a plurality of said sharing linear portions integrating said adjacent wavy annular members with each other;

wherein said wavy annular member has a short linear portion connecting said termination point of said sharing linear portion thereof and the apex of said one-end side bent portion thereof to each other; and wherein said short linear portions each connecting said start point of said sharing linear portion and said apex of said other-end side bent portion to each other are formed not continuously in said axial direction of said stent, but said short linear portions are formed substantially straight.

2. A stent according to claim 1, wherein said stent has a bifurcating portion formed by said start point of said sharing linear portion and a bifurcating portion formed by said termination point of said sharing linear portion.

3. A stent according to claim 1, wherein said wavy annular member has a short linear portion connecting said start point of said sharing linear portion thereof the apex of said other-end side bent portion thereof to each other.

4. A stent according to claim 1, wherein each of said wavy annular members has a big wavy portion forming a projected one-end side apex projected closer to said one-end of said stent than said apexes of other one-end side bent portions and a projected other-end side apex projected closer to said other-end of said stent than said apexes of other other-end side bent portions.

5. A stent according to claim 4, wherein a linear portion disposed between said projected one-end side apex of said big wavy portion and said projected other-end side apex thereof form a long linear portion.

6. A stent according to claim 1, wherein said wavy annular member has a long linear portion connecting a termination point of said sharing linear portion thereof and an apex of said other-end side bent portion thereof to each other.

7. A stent according to claim 1, wherein a plurality of sharing linear portions is formed between said wavy annular members adjacent to each other in said axial direction of said stent.

8. A stent according to claim 1, wherein a plurality of sharing linear portions is formed between said wavy annular members adjacent to each other in said axial direction of said stent; and a plurality of said sharing linear portions is formed oppositely to each other or substantially equiangularly with respect to said axis of said stent.

9. A stent according to claim 1, wherein said wavy annular member has a plurality of big wavy portions.

10. A stent according to claim 1, wherein said wavy annular member has a plurality of big wavy portions; and a plurality of said big wavy portions is formed oppositely to each other or substantially equiangularly with respect to said axis of said stent.

11. A stent according to claim 1, wherein said apex of each of said one-end side bent portions of each wavy annular member penetrates into a space formed between said apexes of said adjacent other-end side bent portions of one of said adjacent wavy annular members; and said apex of each of said other-end side bent portions of each wavy annular member penetrates into a space formed between said apexes of said adjacent one-end side bent portions of said other of said adjacent wavy annular members.

12. A stent according to claim 1, wherein said stent is a self-expandable stent which is formed substantially cylindrically, decreased in a diameter thereof when said stent is inserted into an organism, and is capable of returning to a configuration before said diameter of said stent is decreased when said stent is implanted in said organism.

13. A stent according to claim 1, wherein said stent is formed as a tube, has a diameter whose dimension is so set that said stent can be inserted into a lumen inside an organism, and can be expanded when a force spreading radially outwardly from an inside of said tube is applied thereto.

14. A stent according to claim 1, having first pattern sharing linear portions extended obliquely with respect to said axis of said stent and second pattern sharing linear portions extended obliquely with respect to said axis of said stent in a direction from a direction in which said first pattern sharing linear portions are extended.

15. A stent according to claim 14, wherein said first pattern sharing linear portions and said second pattern sharing linear portions are disposed alternately in said axial direction of said stent.

16. A stent according to claim 14, wherein said second pattern sharing linear portion is shifted from said first pattern sharing linear portion in a circumferential direction of said stent.

17. A stent according to claim 1, wherein a coupling portion for coupling a wavy annular member disposed at both ends of said stent and a wavy annular member adjacent thereto to each other.

18. A stent according to claim 1, wherein a larger number of sharing linear portions are formed between a wavy annular member disposed at both ends of said stent and a wavy annular member adjacent thereto than between adjacent wavy annular members disposed at other portions of said stent.

19. A stent according to claim 1, comprising a contrast marker provided at an end of said stent, wherein an end of said contrast marker is not projected beyond said end of said stent.

20. A stent according to claim 1, comprising an opening formed at an apex disposed at one end of the stent and for fixing said contrast maker has two leg portions extending toward an other end of the stent, and said the two leg portions are spaced from each other and substantially parallel.

21. A self-expandable stent to be implanted in an organism formed approximately cylindrically and integrally from a metal pipe to which super-elastic property can be imparted, by removing a part of said metal pipe other than a part thereof corresponding to a linear portion constituting said stent, wherein said stent shows super-elastic property before and after said stent is inserted into an organism; a line width of a linear portion of said stent is set to 100 to 170 µm; a thickness of said linear portion is set to 180 to 230 µm; and a compression load for compressing an axial length of said stent by 20% is set to 10 to 20 gf, wherein said stent comprises:

a plurality of wavy annular members composing said linear portion and arranged in an axial direction thereof, wherein each of said wavy annular members has a plurality of one-end side bent portions each having an apex at a one-end side of said stent in said axial direction thereof and a plurality of other-end side bent portions each having an apex at an other-end side of said stent in said axial direction thereof; and in said wavy annular members disposed adjacently to each other in said axial direction of said stent, said wavy annular member disposed at said one-end side of said stent in said axial direction thereof has a sharing linear portion having a start point at or in the vicinity of said apex of one of said other-end side bent portions of said wavy annular member disposed at said one-end side of said stent, and a termination point between said apex of said other-end side bent portion of said wavy annular member disposed at said one-end side of said stent and said apex of one of said one-end side bent portions of said wavy annular member disposed at said one-end side of said stent, wherein said wavy annular member disposed at said one-end side of said stent comprises both the start point and the termination point of said sharing linear portion; and said stent having a plurality of said sharing linear portions integrating said adjacent wavy annular members with each other;

wherein said wavy annular member has a short linear portion connecting said Termination point of said sharing linear portion thereof and the arpex of said one-end side bent portion thereof to each other; and wherein said short linear portions each connecting said start point of said sharing linear portion and said apex of said other-end side bent portion to each other are formed not continuously in said axial direction of said stent, but said short linear portions are formed substantially straight.

22. A stent according to claim 21, wherein said stent has a bifurcating portion formed by said start point of said sharing linear portion and a bifurcating portion formed by said termination point of said sharing linear portion.

23. A stent according to claim 21, wherein a plurality of sharing linear portions is formed between said wavy annular members adjacent to each other in said axial direction of said stent.

24. A stent according to claim 21, wherein a plurality of sharing linear portions is formed between said wavy annular members adjacent to each other in said axial direction of said stent; and a plurality of said sharing linear portions is formed oppositely to each other or substantially equiangularly with respect to said axial direction of said stent.

25. A stent according to claim 21, wherein said apex of each of said one-end side bent portions of each wavy annular member penetrates into a space formed between said apexes of said adjacent other-end side bent portions of one of said adjacent wavy annular members; and said apex of each of said other-end side bent portions of each wavy annular member penetrates into a space formed between said apexes of said adjacent one-end side bent portions of said other of said adjacent wavy annular members.

26. A stent according to claim 21, having first pattern sharing linear portions extending obliquely with respect to said axial direction of said stent and second pattern sharing linear portions extending obliquely with respect to said axial direction of said stent in a direction different from a direction in which said first pattern sharing linear portions extend.

27. A stent according to claim 26, wherein said first pattern sharing linear portions and said second pattern sharing linear portions are disposed alternately in said axial direction of said stent.

28. A stent according to claim 26, wherein said second pattern sharing linear portion is shifted from said first pattern sharing linear portion in a circumferential direction of said stent.

29. A stent according to claim 21, comprising a bent linear portion, one end of which is disposed at a start point or a termination point of a sharing linear portion of said wavy annular member and other end of which is disposed at a start point or a termination point of a sharing linear portion of a wavy annular member adjacent to said wavy annular member at a proximal side of said stent in said axial direction thereof, wherein said bent linear portion has a one-end side bent portion or/and an other-end side bent portion.

30. A stent according to claim 21, wherein a coupling portion for coupling a wavy annular member disposed at both ends of said stent and a wavy annular member adjacent thereto to each other.

31. A stent according to claim 21, wherein a larger number of sharing linear portions are formed between a wavy annular member disposed at both ends of said stent and a wavy annular member adjacent thereto than between adjacent wavy annular members disposed at other portions of said stent.

32. A stent according to claim 21, comprising a contrast marker provided at an end of said stent, wherein an end of said contrast marker is not projected beyond said end of said stent.

33. A stent according to claim 21, comprising a plurality of contrast markers provided at an end thereof; and two leg portions extended toward an axial center of said stent from each marker-located position with said leg portions spaced from each other at a certain interval, wherein in a contracted state of said stent, said two leg portions are spaced from each other and almost parallel with a linear portion of said stent dose thereto.

34. A stent according to claim 1, wherein all of the wavy annular members except a wavy annular member located at the other end of the stent have a short linear portion connecting said termination point of said sharing linear portion thereof and the apex of said one-end side bent portion thereof to each other.

35. A stent according to claim 21, wherein all of the wavy annular members except a wavy annular member located at the other end of the stent have a short linear portion connecting said termination point of said sharing linear portion thereof and the apex of said one-end side bent portion thereof to each other.

* * * * *

UNITED STATES PATENT AND TRADEMARK OFFICE
CERTIFICATE OF CORRECTION

| | | |
|---|---|---|
| PATENT NO. | : 7,651,524 B2 | |
| APPLICATION NO. | : 11/905289 | |
| DATED | : January 26, 2010 | |
| INVENTOR(S) | : Yousuke Moriuchi et al. | |

It is certified that error appears in the above-identified patent and that said Letters Patent is hereby corrected as shown below:

On the Title Page Item (57)
In the Abstract, line 9, insert --,-- after "stent".
In column 4, line 1, insert --,-- after "stent".
In column 5, line 13, insert --,-- after "embodiment".
In column 5, line 38, insert --,-- after "embodiment".
In column 5, line 45, insert --,-- after "embodiment".
In column 6, line 27, change "gong" to --(long--.
In column 6, line 46, insert --,-- after "embodiment"; change "dosed" to --closed--.
In column 6, line 61, change "dosed" to --closed--.
In column 8, line 24, insert --,-- after "2".
In column 15, line 27, change "power" to --(lower--.
In column 16, line 20, insert --,-- after "stent".
In column 17, line 37, change "for." to --form--.
In column 19, line 8, insert --.-- after "treatment".
In column 19, line 43, insert --:-- after "stent".
In column 20, line 21, insert --,-- after "steel".
In column 20, line 34, insert --,-- after "stent".
In column 20, line 57, insert --,-- after "polishing".
In column 21, line 12, insert --,-- after "jig".
In column 21, line 55, insert --,-- after "treatment".
In column 22, line 51, insert --,-- after "treatment".
In column 23, line 47, insert --,-- after "treatment".
In column 23, line 53, change "0.22" to --0.2--.
In column 24, line 43, insert --,-- after "treatment".
In column 27, line 23, change "100" to --10--.
In column 33, line 8, insert --,-- after "stent".
In column 35, line 31, insert --,-- after "stent".
In column 38, line 49, insert --,-- after "palladium".
In column 38, line 60, insert --,-- after "out".

Signed and Sealed this
Fifteenth Day of February, 2011

David J. Kappos
*Director of the United States Patent and Trademark Office*

In column 40, line 2, insert --,-- after "thereof".
In column 41, line 62, insert --,-- after "out".
In column 42, line 6, change "dose" to --close--.
In column 42, line 29, change "dose" to --close--.
In column 43, line 63, change "20" to --2.0--.
In column 43, line 63, change "25" to --2.5--.
In column 43, line 65, change "mm" to --μm--.
In column 44, line 6, change "Zr" to --Zn--.
In column 44, line 19, change "NiX" to --Ni-X--.
In column 44, line 48, insert --,-- after "extrusion".
In column 44, line 55, insert --,-- after "etching".
In column 45, line 12, insert --:-- after "stent".
In column 45, line 17, insert --;-- after "used".
In column 45, line 23, change "add" to --acid--.
In column 45, line 24, change "add" to --acid--.
In column 45, line 40, insert --,-- after "extent".
In column 46, line 38, insert --,-- after "treatment".
In column 47, line 23, insert --,-- after "stent".
In column 47, line 43, insert --,-- after "stent".
In column 47, line 64, insert --,-- after "stent".
In column 48, line 17, insert --,-- after "stent".
In claim 21, line 2, change "Termination" to --termination--.